US008658155B2

(12) United States Patent
Wiles et al.

(10) Patent No.: US 8,658,155 B2
(45) Date of Patent: Feb. 25, 2014

(54) COMPOSITIONS AND METHODS RELATING TO NON-HUMAN ANIMALS MODIFIED TO PROMOTE PRODUCTION OF SELECTED GAMETES

(75) Inventors: Michael V. Wiles, Mount Desert, ME (US); Robert Taft, Southwest Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 0 days.

(21) Appl. No.: 13/337,892

(22) Filed: Dec. 27, 2011

(65) Prior Publication Data

US 2012/0167242 A1 Jun. 28, 2012

Related U.S. Application Data

(60) Provisional application No. 61/427,337, filed on Dec. 27, 2010.

(51) Int. Cl.

*A01N 63/00* (2006.01)
*C12N 15/00* (2006.01)
*C12N 15/63* (2006.01)
*C12N 15/87* (2006.01)
*C07H 21/04* (2006.01)

(52) U.S. Cl.

USPC ..................... 424/93.21; 435/320.1; 435/455; 435/463; 536/23.7; 536/24.1

(58) Field of Classification Search

USPC .................... 435/320.1, 455, 463; 424/93.21; 536/23.7, 24.1

See application file for complete search history.

(56) References Cited

U.S. PATENT DOCUMENTS 7,294,754 B2 11/2007 Poueymirou et al.
7,576,259 B2 8/2009 Poueymirou et al.
7,659,442 B2 2/2010 Poueymirou et al.
2009/0271884 A1 10/2009 Poueymirou et al.
2010/0229254 A1 9/2010 Kmita et al.

FOREIGN PATENT DOCUMENTS

WO WO-2009/053982 4/2009
WO WO-2009/114400 9/2009

OTHER PUBLICATIONS

Bartell et al., 2000, Biology of Reproduction, vol. 63, p. 409-416.*
Beck et al., Structure, tissue distribution and genomic organization of the murine RRM-type RNA binding proteins TIA-1 and TIAR, *Nucleic Acids Res*,. 24, 3829-3835, 1996.
Bennet et al., Refined structure of dimeric diphtheria toxin at 2.0 A resolution, *Protein Science*, 3: 1444-1463, 1994.
Bergqvist et al., Transgenic Cre recombinase expression in germ cells and early embryogenesis directs homogeneous and ubiquitous deletion of loxP-flanked gene segments, *FEBS Lett*, 438:76-80, 1998.
Bhattacharya et al., The mouse dead-end gene isoform alpha is necessary for germ cell and embryonic viability, *Biochem Biophys Res Commun*., 355 194-9, 2007.
Borrelli et al., Targeting of an inducible toxic phenotype in animal cells, *PNAS USA*, 85 (20), 7572-7576, 1988.
Braun et al, Hepatocyte transplantation in a model of toxin-induced liver disease: variable therapeutic effect during replacement of damaged parenchyma by donor cells, *Nature Medicine*, 6: 320-326, 2000.
Buehr et al., Rapid Loss of Oct-4 and Pluripotency in Cultured Rodent Blastocysts and Derivative Cell Lines, *Biol. Reprod*., 68: 222-229, 2003.
Castigli et al., CD40-deficient mice generated by recombination-activating gene-2-deficient blastocyst complementation, *PNAS USA* 91, 12135-12139, 1994.
Chen et al., RAG-2-deficient blastocyst complementation: An assay of gene function in lymphocyte Development, *PNAS USA*, 90: 4528-4532, 1993.
Chen et al., Bigenic Cre/loxP, puDeltatk conditional genetic ablation, *Nucl Acids Res*, 32(20): e161, 2004.
Clark, Human STELLAR, NANOG, and GDF3 genes are expressed in pluripotent cells and map to chromosome 12p13, a hotspot for teratocarcinoma, *Stem Cells*, 22(2): 169-79, 2004.
Collignon et al., A comparison of the properties of Sox-3 with Sry and two related genes, Sox-1 and Sox-2, *Development* 122 (2), 509-520, 1996.
Crackower et al., Essential role of Fkbp6 in male fertility and homologous chromosome pairing in meiosis, *Science* 300: 1291-1295, 2003.
Fujiwara et al., Isolation of a DEAD-family protein gene that encodes a murine homolog of Drosophila vasa and its specific expression in germ cell lineage, *PNAS* 91: 12258-12262, 1994.
Gallardo et al., Generation of a germ cell-specific mouse transgenic Cre line, Vasa-Cre, *Genesis*, 45: 413-417, 2007.
Hirota, T et al., Drug-inducible gene recombination by the Dppa3-MER Cre MER transgene in the developmental cycle of the germ cell lineage in mice, *Biol Reproduction*, 85(2): 367-377, 2011.
Ivanova et al., In vivo genetic ablation by Cre-mediated expression of diphtheria toxin fragment A, *Genesis* 43(3): 129-135, 2005.
Izquierdo, Control of the ATP synthase beta subunit expression by RNA-binding proteins TIA-1, TIAR, and HuR, *Biochem Biophys Res Commun*, 348(2): 703-711, 2006.
Jansson et al., W41/W41 blastocyst complementation: a system for genetic modeling of hematopoiesis, *Blood*, 115(1): 47-50, 2010.
Kee et al., Human DAZL, DAZ and BOULE genes modulate primordial germ-cell and haploid gamete formation, *Nature*, 462: 222-225, 2009.
Kmita et al., Targeted inversion of a polar silencer within the HoxD complex re-allocates domains of enhancer sharing, *Nat Genet*, 26:451-454, 2000.

(Continued)

*Primary Examiner* — Shin-Lin Chen
(74) *Attorney, Agent, or Firm* — Gifford, Krass, Sprinkle, Anderson & Citkowski, P.C.

(57) ABSTRACT

Methods and compositions for producing selected non-human mammalian germ cells and gametes and for making non-human animals using the produced germ cells and gametes are provided by the present invention. Methods of generating a non-human embryo and/or animal derived from donor stem cells, methods of generating chimeric non-human animals having substantially all gametes and/or germ cells derived from the donor stem cells, methods of producing a non-human host embryo lacking functional endogenous germ cells and non-human host embryos incapable of developing endogenous gametes of the present invention are described herein.

1 Claim, 6 Drawing Sheets

(56) References Cited

OTHER PUBLICATIONS

Kobayashi, T. et al., Generation of Rat Pancreas in Mouse by Interspecific Blastocyst Injection of Pluripotent Stem Cells, *Cell*, 142: 787-99, Sep. 3, 2010.
Lange et al., The fragilis interferon-inducible gene family of transmembrane proteins is associated with germ cell specification in mice, *BMC Dev Biol*, 3: 1, 2003.
Linhera K. et al., An epigenetic mechanism regulates germ cell-specific expression of the porcine Deleted in Azoospermia-Like (DAZL) gene, *Differentiation*, 77(4): 335-349, 2009.
Lomeli H et al., Targeted insertion of Cre recombinase into the TNAP gene: excision in primordial germ cells, *Genesis*, 26:116-117, 2000.
MacGregor et al., Tissue non-specific alkaline phosphatase is expressed in both embryonic and extraembryonic lineages during mouse embryogenesis but is not required for migration of primordial germ cells, *Development*, 121(5): 1487-1496, 1995.
Matsumura, H. et al., Lineage-specific cell disruption in living mice by Cre-mediated expression of diphtheria toxin A chain, *Biochemical and Biophysical Research Communication*, 321:275-9, 2004.
Meng et al., A novel human gene FKBP6 is deleted in Williams syndrome, *Genomics*, 52: 130-137, 1998.
Mizuno et al., Novel variants of Oct-3/4 gene expressed in mouse somatic cells, *J Biol Chem*, 283(45): 30997-31004, 2008.
Nicholas et al., Characterization of a Dazl-GFP germ cell-specific reporter, *Genesis*, 47: 74-84, 2009.
Nordhoff et al., Comparative analysis of human, bovine, and murine Oct-4 upstream promoter sequences, *Mammalian Genome*, 12(4): 309-317, 2001.
Oginuma et al., Identification of presomitic mesoderm (PSM)—specific Mesp1 enhancer and generation of a PSMspecific Mesp1/Mesp2-null mouse using BAC-based rescue technology, *Mech Dev*, 125: 432-440, 2008.
O'Gorman, S. et al., Protamine-Cre recombinase transgenes efficiently recombine target sequences in the male germ line of mice, but not in embryonic stem cells, *Proc Natl Acad Sci USA*, 94: 14602-7, Dec. 1997.
Ohinata et al., Blimp1 is a critical determinant of the germ cell lineage in mice, *Nature*, 436: 207-213, 2005.
Okazawa et al., The oct3 gene, a gene for an embryonic transcription factor, is controlled by a retinoic acid repressible enhancer, *EMBO* 10: 2997-3005, 1991.
Ovitt et al., The molecular biology of Oct-4 in the early mouse embryo, *Mol Hum Reprod*, 4: 1021-31,1998.
Patterson et al., Genomic organization of mouse and human 65 kDa FK506-binding protein genes and evolution of the FKBP multigene family, *Genomics*, 79: 881-889, 2002.
Qiu et al., Primary structure of c-kit: relationship with the CSF-1/PDGF receptor kinase family—oncogenic activation of v-kit involves deletion of extracellular domain and C terminus, *EMBO* 7(4): 1003-1011, 1988.
Reijo, R et al., Mouse autosomal homolog of DAZ, a candidate male sterility gene in humans, is expressed in male germ cells before and after puberty, *Genomics*, 35, 346-352, 1996.
Rosenberg et al., FADD Deficiency Impairs Early Hematopoiesis in the Bone Marrow, *J Immunol*, 186: 203-213, 2011.
Saitou et al., A molecular programme for the specification of germ cell fate in mice, *Nature*, 418: 293-300, 2002.
Salomon, B. et al., A Truncated Herpes Simplex Virus Thymidine Kinase Phosphorylates Thymidine and Nucleoside Analogs and Does Not Cause Sterility in Transgenic Mice, *Molecular and Cellular Biology*, 15(10): 5322-28, Oct. 1995.
Schwenk, F. et al., A cre-transgenic mouse strain for the ubiquitous deletion of loxPflanked gene segments including deletion in germ cells, *Nucleic Acids Research*, 23(24): 5080-81, 1995.
Solter, D., Viable Rat-Mouse Chimeras: Where do we go from here?, *Cell*, 142: 676-8, Sep. 3, 2010.
Suzuki et al., Nanos3 maintains the germ cell lineage in the mouse by suppressing both Bax-dependent and-independent apoptotic pathways, *Dev Biol*, 318: 133-142, 2008.
Suzuki et al., Functional redundancy among Nanos proteins and a distinct role of Nanos2 during male germ cell development, *Development*, 134: 77-83, 2007.
Suzuki et al., The Nanos3-3'UTR is required for germ cell specific NANOS3 expression in mouse embryos, *PLoS One*, 5(2):e9300, 2010.
Sylvester et al., Regulation of the Oct-4 gene by nuclear receptors, *Nucleic Acids Res*, 22: 901-911, 1994.
Tanaka, S. et al., Developmentally regulated expression of mil-1 and mil-2, mouse interferon-induced transmembrane protein like genes, during formation and differentiation of primordial germ cells, *Mech Dev*, 119S: S261-S267, 2002.
Tanaka, S. et al., Regulation of expression of mouse interferon-induced transmembrane protein like gene-3, Ifitm3 (mil-1, fragilis), in germ cells, *Dev Dyn*, 230: 651-659, 2004.
Tanaka et al., The mouse homolog of Drosophila Vasa is required for the development of male germ cells, *Gene Dev*, 14: 841-853, 2000.
Tominaga et al., Characterization of the testis-specific promoter region in the human pituitary adenylate cyclaseactivating polypeptide (PACAP) gene, *Genes to Cells*, 15(6): 595-606, 2010.
Toyooka et al., Expression and intracellular localization of mouse Vasa-homologue protein during germ cell development, *Mech Dev*, 93: 139-49, 2000.
Tsuda et al., Conserved role of nanos proteins in germ cell development, *Science*, 301:1239-1241, 2003.
Turner et al., Blimp-1, a novel zinc finger-containing protein that can drive the maturation of B lymphocytes into immunoglobulin-secreting cells, *Cell*, 77: 297-306, 1994.
Velkey et al., Oct4 RNA interference induces trophectoderm differentiation in mouse embryonic stem cells, *Genesis*, 37: 18-24, 2003.
Wang et al., An abundance of X-linked genes expressed in spermatogonia, *Nat Genet*, 27:422-426, 2001.
Weber, P. et al., Temporally Controlled Site-Specific Mutagenesis in the Germ Cell Lineage of the Mouse Testis, *Biology of Reproduction*, 68: 553-9, 2003.
Wu et al., Isolation and characterization of the murine Nanog gene promoter, *Cell Res*, 15: 317-24, 2005.
Wu et al., Motoneurons and oligodendrocytes are sequentially generated from neural stem cells but do not appear to share common lineage-restricted progenitors in vivo, *Development*, 133: 581-90, 2006.
Xuan et al., Genome-wide promoter extraction and analysis in human, mouse, and rat, *Genome Biol*, 6::R72, 2005.
Yamaguchi et al., Conditional knockdown of Nanog induces apoptotic cell death in mouse migrating primordial germ cells, *Development*, 136: 4011-4020, 2009.
Yamaji, M et al., Critical function of Prdm14 for the establishment of the germ cell lineage in mice, *Nature Genet*, 40: 1016-1022, 2008.
Yasuda, H et al., Cloning and functional analysis of the mouse c-kit promoter, *Biochem Biophys Res Commun*, 191: 893-901, 1993.
Yeom et al., Structure, expression and chromosomal location of the Oct-4 gene, *Mech Dev*, 35: 171-179, 1991.
Youngren et al., The Ter mutation in the dead end gene causes germ cell loss and testicular germ cell tumours, *Nature*, 435: 360-364, 2005.
Zafarana et al., Specific knockdown of OCT4 in human embryonic stem cells by inducible short hairpin RNA interference, *Stem Cells*, 27: 776-782, 2009.
Zhang et al., Development of an HSV-tk transgenic mouse model for study of liver damage *FEBSJ*, 272:2207-15, 2005.
Bartel, J. et al., Elimination of male germ cells in transgenic mice by the diphtheria toxin A chain gene directed by the histone H1t promoter, *Biology of Reproduction*, 63: 409-416, 2000.
Nagy, A. et al., Derivation of completely cell culture-derived mice from early-passage embryonic stem cells, *Proc. Natl. Acad. Sci, USA*, 90: 8424-28, Sep. 1993.

* cited by examiner

COMPOSITIONS AND METHODS RELATING TO NON-HUMAN ANIMALS MODIFIED TO PROMOTE PRODUCTION OF SELECTED GAMETES

REFERENCE TO RELATED APPLICATION

This application claims priority from U.S. Provisional Patent Application Ser. No. 61/427,337, filed Dec. 27, 2010, the entire content of which is incorporated herein by reference.

GOVERNMENT SUPPORT

This invention was made with Government support under Grant No. R21 RR031289 awarded by the National Institutes of Health. The Government has certain rights in the invention.

FIELD OF THE INVENTION

The present invention relates generally to methods and compositions for producing selected non-human mammalian germ cells and gametes and for making non-human animals using the produced germ cells and gametes. According to specific aspects the present invention relates to methods of generating a non-human embryo and/or animal derived from donor stem cells, methods of generating chimeric non-human animals having substantially all gametes and/or germ cells derived from the donor stem cells, methods of producing a non-human host embryo lacking functional endogenous germ cells and a non-human host embryo incapable of developing endogenous gametes.

BACKGROUND OF THE INVENTION

Prior to the present invention, the efficiency of stem cells to populate the germline and to produce non-human animals has been a major challenge, and there has been a continuing need for methods and compositions for the production of non-human animals from stem cells, including production of genetically modified non-human animals from genetically modified stem cells. This invention provides methods and compositions to produce non-human host embryos having a receptive niche for the development of donor stem cells, including genetically modified donor stem cells, into germ cells and gametes.

SUMMARY OF THE INVENTION

Methods of generating a non-human embryo and/or animal derived from donor stem cells, are provided according to embodiments of the present invention which include: a) producing a preimplantation non-human host embryo incapable of developing endogenous gametes; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

The terms "endogenous gametes" and "endogenous germ cells" as used herein refer to gametes and germ cells "originating or produced from within" a host embryo and exclude gametes and germ cells in the host embryo which are derived from donor stem cells.

Methods of generating a non-human embryo and/or animal derived from donor stem cells, are provided according to embodiments of the present invention which include: a) generating a preimplantation non-human host embryo incapable of developing endogenous gametes by expressing a cytotoxic protein in germ cells of the non-human host embryo to ablate endogenous germ cells; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes by expressing an inhibitory RNA in germ cells of the non-human host embryo to ablate endogenous germ cells; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes by expressing a recombinase to excise two inverted recombinase recognition sites placed in a chromosome of a preimplantation non-human host embryo to ablate the endogenous germ cells; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

A preimplantation non-human host embryo produced according to methods described herein is incapable of developing endogenous gametes due to human intervention using methods of the present invention, such as expressing a cytotoxic protein in germ cells of the non-human host embryo to ablate endogenous germ cells; expressing an inhibitory RNA in germ cells of the non-human host embryo to ablate endogenous germ cells; and placing two inverted recombinase recognition sites in a chromosome of a preimplantation non-human host embryo and expressing a recombinase to ablate the endogenous germ cells.

As described herein, donor stem cells are introduced into the preimplantation non-human host embryo. As described herein, the donor stem cells may be introduced before ablation of the endogenous germ cells such that it will be appreciated that the endogenous germ cells in the preimplantation non-human host embryo can be referred to as "lacking, or destined to lack endogenous germ cells."

A preimplantation non-human host embryo can be a 2-cell stage embryo, a 4-cell stage embryo, a 8-cell stage embryo, a 16-cell stage embryo, a 32-cell stage embryo, a 64-cell stage embryo, a morula or a blastocyst. The inner cell mass of preimplantation non-human host embryos is not ablated according to methods of the present invention.

Methods of generating a non-human embryo and/or animal derived from donor stem cells, are provided according to embodiments of the present invention which include: a) generating a preimplantation non-human host embryo incapable of developing endogenous gametes wherein the preimplantation non-human host embryo includes a transgene, the transgene including a nucleic acid sequence encoding a cytotoxic protein operably linked to a developmentally regulated promoter active in germ cells of the embryo during at least a portion of a developmental stage corresponding to embryonic day 6 to embryonic day 14 in mice, to ablate the endogenous germ cells of the embryo; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes wherein the preimplantation non-human host embryo includes a transgene, the transgene including a nucleic acid sequence encoding an inhibitory RNA operably linked to a developmentally regulated promoter active in germ cells of the embryo during at least a portion of a developmental stage corresponding to embryonic day 6 to embryonic day 14 in mice, to ablate the endogenous germ cells of the embryo; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes wherein the preimplantation non-human host embryo includes at least two transgenes, one transgene including a nucleic acid sequence encoding a recombinase linked to a developmentally regulated promoter active in germ cells of the embryo during at least a portion of a developmental stage corresponding to embryonic day 6 to embryonic day 14 in mice, to ablate the endogenous germ cells of the embryo and the second transgene including a nucleic acid sequence encoding a cytotoxic protein or an inhibitory RNA operably linked to recombinase recognition sites; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a rodent embryo and/or rodent derived from donor stem cells, are provided according to embodiments of the present invention which include: a) generating a preimplantation rodent host embryo incapable of developing endogenous gametes wherein the preimplantation rodent host embryo includes a transgene, the transgene including a nucleic acid sequence encoding a cytotoxic protein operably linked to a developmentally regulated promoter active in germ cells of the embryo during at least a portion of a developmental stage corresponding to embryonic day 6 to embryonic day 14 of a mouse embryo, to ablate the endogenous germ cells of the embryo; b) introducing donor stem cells into the preimplantation rodent host embryo; c) gestating the rodent host embryo of b) under conditions suitable for development of the embryo, thereby generating a chimeric rodent having substantially all gametes and/or germ cells derived from the donor stem cells; and d) making a rodent embryo and/or rodent using the gametes and/or germ cells derived from the donor stem cells.

Methods of generating a rodent embryo and/or rodent derived from donor stem cells, are provided according to embodiments of the present invention which include: a) generating a preimplantation rodent host embryo incapable of developing endogenous gametes wherein the preimplantation rodent host embryo includes a transgene, the transgene including a nucleic acid sequence encoding an inhibitory RNA operably linked to a developmentally regulated promoter active in germ cells of the embryo during at least a portion of a developmental stage corresponding to embryonic day 6 to embryonic day 14 of a mouse embryo, to ablate the endogenous germ cells of the embryo; b) introducing donor stem cells into the preimplantation rodent host embryo; c) gestating the rodent host embryo of b) under conditions suitable for development of the embryo, thereby generating a chimeric rodent having substantially all gametes and/or germ cells derived from the donor stem cells; and d) making a rodent embryo and/or rodent using the gametes and/or germ cells derived from the donor stem cells.

Methods of generating a rodent embryo and/or rodent derived from donor stem cells, are provided according to embodiments of the present invention which include: a) generating a preimplantation rodent host embryo incapable of developing endogenous gametes wherein the preimplantation rodent host embryo includes a recombinase operably linked to a developmentally regulated promoter active in germ cells of the embryo during at least a portion of a developmental stage corresponding to embryonic day 6 to embryonic day 14 of a mouse embryo to excise two inverted recombinase recognition sites placed in a chromosome of a preimplantation non-human host embryo to ablate the endogenous germ cells, to ablate the endogenous germ cells of the embryo; b) introducing donor stem cells into the preimplantation rodent host embryo; c) gestating the rodent host embryo of b) under conditions suitable for development of the embryo, thereby generating a chimeric rodent having substantially all gametes and/or germ cells derived from the donor stem cells; and d) making a rodent embryo and/or rodent using the gametes and/or germ cells derived from the donor stem cells.

Methods of generating a mouse embryo and/or mouse derived from donor stem cells, are provided according to embodiments of the present invention which include: a) generating a preimplantation mouse host embryo incapable of developing endogenous gametes wherein the preimplantation mouse host embryo includes a transgene, the transgene including a nucleic acid sequence encoding a cytotoxic protein operably linked to a developmentally regulated promoter active in germ cells of the embryo during a portion of embryonic day 6 to embryonic day 14 of a mouse embryo, to ablate the endogenous germ cells of the embryo; b) introducing donor stem cells into the preimplantation mouse host embryo; c) gestating the mouse host embryo of b) under conditions suitable for development of the embryo, thereby generating a chimeric mouse having substantially all gametes and/or germ cells derived from the donor stem cells; and d) making a mouse embryo and/or mouse using the gametes and/or germ cells derived from the donor stem cells.

Methods of generating a mouse embryo and/or mouse derived from donor stem cells, are provided according to embodiments of the present invention which include: a) generating a preimplantation mouse host embryo incapable of developing endogenous gametes wherein the preimplantation mouse host embryo includes a transgene, the transgene including a nucleic acid sequence encoding an inhibitory RNA operably linked to a developmentally regulated promoter active in germ cells of the embryo during a portion of embryonic day 6 to embryonic day 14 of a mouse embryo, to ablate the endogenous germ cells of the embryo; b) introducing donor stem cells into the preimplantation mouse host embryo; c) gestating the mouse host embryo of b) under conditions suitable for development of the embryo, thereby generating a chimeric mouse having substantially all gametes and/or germ cells derived from the donor stem cells; and d) making a mouse embryo and/or mouse using the gametes and/or germ cells derived from the donor stem cells.

Methods of generating a mouse embryo and/or mouse derived from donor stem cells, are provided according to embodiments of the present invention which include: a) generating a preimplantation mouse host embryo incapable of developing endogenous gametes wherein the preimplantation mouse host embryo includes at least two transgenes, one transgene including a nucleic acid sequence encoding a recombinase operably linked to a developmentally regulated promoter active in germ cells of the embryo during a portion of embryonic day 6 to embryonic day 14 of a mouse embryo, and the second transgene including a nucleic acid sequence encoding a cytotoxic protein or an inhibitory RNA operably linked to recombinase recognition sites to ablate the endogenous germ cells of the embryo; b) introducing donor stem cells into the preimplantation mouse host embryo; c) gestating the mouse host embryo of b) under conditions suitable for development of the embryo, thereby generating a chimeric mouse having substantially all gametes and/or germ cells derived from the donor stem cells; and d) making a mouse embryo and/or mouse using the gametes and/or germ cells derived from the donor stem cells.

Methods of generating a rat embryo and/or rat derived from donor stem cells, are provided according to embodiments of the present invention which include: a) generating a preimplantation rat host embryo incapable of developing endogenous gametes wherein the preimplantation rat host embryo includes a transgene, the transgene including a nucleic acid sequence encoding a cytotoxic protein operably linked to a developmentally regulated promoter active in germ cells of the embryo during a portion of embryonic day 7 to embryonic day 16 of a rat embryo, to ablate the endogenous germ cells of the embryo; b) introducing donor stem cells into the preimplantation rat host embryo; c) gestating the rat host embryo of b) under conditions suitable for development of the embryo, thereby generating a chimeric rat having substantially all gametes and/or germ cells derived from the donor stem cells; and d) making a rat embryo and/or mouse using the gametes and/or germ cells derived from the donor stem cells.

Methods of generating a rat embryo and/or rat derived from donor stem cells, are provided according to embodiments of the present invention which include: a) generating a preimplantation rat host embryo incapable of developing endogenous gametes wherein the preimplantation rat host embryo includes a transgene, the transgene including a nucleic acid sequence encoding an inhibitory RNA operably linked to a developmentally regulated promoter active in germ cells of the embryo during a portion of embryonic day 7 to embryonic day 16 of a rat embryo, to ablate the endogenous germ cells of the embryo; b) introducing donor stem cells into the preimplantation rat host embryo; c) gestating the rat host embryo of b) under conditions suitable for development of the embryo, thereby generating a chimeric rat having substantially all gametes and/or germ cells derived from the donor stem cells; and d) making a rat embryo and/or mouse using the gametes and/or germ cells derived from the donor stem cells.

Methods of generating a rat embryo and/or rat derived from donor stem cells, are provided according to embodiments of the present invention which include: a) generating a preimplantation rat host embryo incapable of developing endogenous gametes wherein the preimplantation rat host embryo includes at least two transgenes, one transgene including a nucleic acid sequence encoding a recombinase operably linked to a developmentally regulated promoter active in germ cells of the embryo during a portion of embryonic day 7 to embryonic day 16 of a rat embryo, and the second transgene including a nucleic acid sequence encoding a cytotoxic protein or an inhibitory RNA operably linked recombinase recognition sites to ablate the endogenous germ cells of the embryo; b) introducing donor stem cells into the preimplantation rat host embryo; c) gestating the rat host embryo of b) under conditions suitable for development of the embryo, thereby generating a chimeric rat having substantially all gametes and/or germ cells derived from the donor stem cells; and d) making a rat embryo and/or mouse using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes by expression of a transgene, the transgene including a nucleic acid sequence encoding a cytotoxic protein operably linked to a developmentally regulated promoter or a ubiquitous promoter, the transgene further including at least one cytotoxic protein inhibitory sequence operably linked to at least two recombinase recognition sites; wherein the non-human host embryo further includes a second transgene including a nucleic acid sequence encoding a recombinase, the nucleic acid sequence encoding the recombinase operably linked to a promoter selected from the group consisting of: a developmentally regulated promoter and a ubiquitous promoter, wherein at least either the first or second transgene is operably linked to a developmentally regulated promoter; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes by expression of a transgene, the transgene including a nucleic acid sequence encoding an inhibitory RNA operably linked to recombinase recognition sites and to a developmentally regulated promoter or a ubiquitous promoter, the transgene further including at least one inhibitory RNA inhibitory sequence operably linked to at least two recombinase recognition sites; wherein the non-human host embryo further includes a second transgene including a nucleic acid sequence encoding a recombinase, the nucleic acid sequence encoding the recombinase operably linked to a promoter selected from the group consisting of: a developmentally regulated promoter and a ubiquitous promoter, wherein at least either the first or second transgene is operably linked to a developmentally regulated promoter; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes wherein the preimplantation non-human host embryo includes a transgene, the transgene including a nucleic acid sequence encoding a cytotoxic protein operably linked to an inducible promoter, an inhibitory RNA operably linked to an inducible promoter or a recombinase operably linked to an inducible promoter, wherein the recombinanse is active to excise two inverted recombinase recognition sites placed in a chromosome of a preimplantation non-human host embryo, to ablate the endogenous germ cells of the embryo; b) introducing donor stem cells into the preimplantation non-human host embryo; c) gestating the non-human host embryo of b) under conditions suitable for development of the embryo, thereby generating a chimeric non-human animal having 80% or more gametes and/or germ cells of the chimeric non-human animal are derived from the donor stem cells; and d) making a non-human embryo or animal using the gametes and/or germ cells derived from the donor stem cells.

Chimeric non-human animals generated according to methods described herein can have substantially all gametes and/or germ cells of the chimeric non-human animal derived from the donor stem cells such as 80%, 81%, 82%, 83%, 84%, 85%, 86%, 87%, 88%, 89%, 90%, 91%, 92%, 93%, 94%, 95%, 96%, 97%, 98%, 99%, or more gametes and/or germ cells of the chimeric non-human animal which are derived from the donor stem cells.

Donor stem cells introduced into a preimplantation non-human host embryo incapable of developing endogenous gametes are embryonic stem cells, epiblast stem cells, embryonic germ cells, induced pluripotent stem cells, genetically modified embryonic stem cells, genetically modified epiblast stem cells, genetically modified embryonic germ cells, genetically modified induced pluripotent stem cells or a combination of any two or more of these.

Methods of generating a non-human embryo and/or animal derived from donor stem cells, are provided according to embodiments of the present invention which include: a) generating a preimplantation non-human host embryo incapable of developing endogenous gametes by expression of a first transgene, the first transgene including a nucleic acid sequence encoding a cytotoxic protein operably linked to a ubiquitous promoter or a developmentally regulated promoter selected from the group consisting of: vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, and Tiar promoter, the transgene further including at least one cytotoxic protein inhibitory sequence operably linked to at least two recombinase recognition sites; wherein the non-human host embryo further includes a second transgene including a nucleic acid sequence encoding a recombinase, the nucleic acid sequence encoding the recombinase operably linked to a ubiquitous promoter or a developmentally regulated promoter selected from the group consisting of: vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, and Tiar promoter, wherein at least either the first or second transgene is operably linked to a developmentally regulated promoter; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes by expression of a first transgene, the first transgene including a nucleic acid sequence encoding an inhibitory RNA operably linked to a ubiquitous promoter or a developmentally regulated promoter selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, the transgene further including at least one cytotoxic protein inhibitory sequence operably linked to at least two recombinase recognition sites; wherein the non-human host embryo further includes a second transgene including a nucleic acid sequence encoding a recombinase, the nucleic acid sequence encoding the recombinase operably linked to a ubiquitous promoter or a developmentally regulated promoter selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, wherein at least either the first or second transgene is operably linked to a developmentally regulated promoter; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes wherein the preimplantation non-human host embryo includes a transgene, the transgene including a nucleic acid sequence encoding a cytotoxic protein operably linked to a developmentally regulated promoter active in germ cells of the embryo during at least a portion of a developmental stage corresponding to embryonic day 6 to embryonic day 14 in mice selected from the group consisting of: vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, and Tiar promoter, to ablate the endogenous germ cells of the embryo; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes wherein the preimplantation non-human host embryo includes a transgene, the transgene including a nucleic acid sequence encoding an inhibitory RNA operably linked to a developmentally regulated promoter active in germ cells of the embryo during at least a portion of a developmental stage corresponding to embryonic day 6 to embryonic day 14 in mice selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, to ablate the endogenous germ cells of the embryo; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes wherein the preimplantation non-human host embryo includes a transgene, the transgene including a nucleic acid sequence encoding a recombinase linked to a developmentally regulated promoter active in germ cells of the embryo during at least a portion of a developmental stage corresponding to embryonic day 6 to embryonic day 14 in mice selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, to ablate the endogenous germ cells of the embryo; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

The preimplantation non-human host embryo is an embryo of any non-human mammal, such as rodent, non-human primate, rabbit, dog, cat, cattle, horse, sheep, goat, endangered mammal and exotic mammal. The preimplantation non-human host embryo is a marmoset embryo, for example. In a further example, the rodent preimplantation host embryo is a mouse or rat embryo.

Optionally, the donor stem cells are derived from a first animal species and the preimplantation non-human host embryo is a different second animal species. In one option, the donor stem cells are rat stem cells and the preimplantation non-human host embryo is a mouse embryo, such that rat gametes and/or rat germ cells are produced in a mouse host animal.

Methods of generating a non-human embryo and/or animal derived from donor stem cells, are provided according to embodiments of the present invention which include: a) generating a preimplantation non-human host embryo incapable of developing endogenous gametes wherein the preimplantation non-human host embryo includes a transgene, the transgene including a nucleic acid sequence encoding Herpes simplex virus thymidine kinase operably linked to a developmentally regulated promoter active in germ cells of the embryo during at least a portion of a developmental stage corresponding to embryonic day 6 to embryonic day 14 in mice and further comprising contacting endogenous germ cells expressing a Herpes simplex virus thymidine kinase with a thymidine analog to ablate the endogenous germ cells of the embryo; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes wherein the preimplantation non-human host embryo includes a transgene, the transgene including a nucleic acid sequence encoding Herpes simplex virus thymidine kinase operably linked to a developmentally regulated promoter active in germ cells of the embryo during at least a portion of a developmental stage corresponding to embryonic day 6 to embryonic day 14 in mice selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, and further comprising contacting endogenous germ cells expressing the Herpes simplex virus thymidine kinase with a thymidine analog to ablate the endogenous germ cells of the embryo; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes wherein the preimplantation non-human host embryo includes a transgene, the transgene including a nucleic acid sequence encoding a functional mutant or truncated Herpes simplex virus thymidine kinase operably linked to a developmentally regulated promoter active in germ cells of the embryo during at least a portion of a developmental stage corresponding to embryonic day 6 to embryonic day 14 in mice selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, and further comprising contacting endogenous germ cells expressing the functional mutant or truncated Herpes simplex virus thymidine kinase with a thymidine analog to ablate the endogenous germ cells of the embryo; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes wherein the preimplantation non-human host embryo includes a transgene, the transgene including a nucleic acid sequence encoding Herpes simplex virus thymidine kinase operably linked to a developmentally regulated promoter active in germ cells of the embryo during at least a portion of a developmental stage corresponding to embryonic day 6 to embryonic day 14 in mice selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, and further comprising contacting endogenous germ cells expressing the Herpes simplex virus thymidine kinase with a thymidine analog selected from the group consisting of: ganciclovir, acyclovir and fialuridine, to ablate the endogenous germ cells of the embryo; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes by expressing diphtheria toxin A fragment, attenuated diphtheria toxin A fragment, tox-176; or a cytotoxic homologue, fragment or variant thereof, in germ cells of the non-human host embryo to ablate endogenous germ cells; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a non-human embryo and/or animal derived from donor stem cells, are provided according to embodiments of the present invention which include: a) generating a preimplantation non-human host embryo incapable of developing endogenous gametes by expression of a first transgene, the first transgene including a nucleic acid sequence encoding diphtheria toxin A fragment, attenuated DTA, tox-176; or a cytotoxic homologue, fragment or variant thereof, operably linked to a ubiquitous promoter or a developmentally regulated promoter selected from the group consisting of: vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, and Tiar promoter, the transgene further including at least one inhibitory sequence for diphtheria toxin A fragment, attenuated DTA, tox-176; or a cytotoxic homologue, fragment or variant thereof, and operably linked to least two recombinase recognition sites; wherein the non-human host embryo further includes a second transgene including a nucleic acid sequence encoding a recombinase, the nucleic acid sequence encoding the recombinase operably linked to a ubiquitous promoter or a developmentally regulated promoter selected from the group consisting of: vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, and Tiar promoter, wherein at least either the first or second transgene is operably linked to a developmentally regulated promoter; b) introducing donor stem cells into the preimplantation non-human host embryo; c) gestating the non-human host embryo of b) under conditions suitable for development of the embryo, thereby generating a chimeric non-human animal having substantially all gametes and/or germ cells derived from the donor stem cells; and d) making a non-human embryo or animal using the gametes and/or germ cells derived from the donor stem cells.

Methods of generating a chimeric non-human animal are provided according to embodiments of the present invention which include: a) producing a preimplantation non-human host embryo incapable of developing endogenous gametes; b) introducing donor stem cells into the preimplantation non-human host embryo; and c) gestating the preimplantation non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes by expressing a cytotoxic protein in germ cells of the non-human host embryo to ablate endogenous germ cells; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes by expressing an inhibitory RNA in germ cells of the non-human host embryo to ablate endogenous germ cells; b) introducing donor stem cells into the preimplantation non-human host embryo; and c) gestating the non-human host embryo of b)

under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes by expressing a recombinase to excise two inverted recombinase recognition sites placed in a chromosome of a preimplantation non-human host embryo and expressing a recombinase to ablate the endogenous germ cells; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes wherein the preimplantation non-human host embryo includes a transgene, the transgene including a nucleic acid sequence encoding a cytotoxic protein operably linked to a developmentally regulated promoter active in germ cells of the embryo during at least a portion of a developmental stage corresponding to embryonic day 6 to embryonic day 14 in mice, to ablate the endogenous germ cells of the embryo; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes wherein the preimplantation non-human host embryo includes a transgene, the transgene including a nucleic acid sequence encoding an inhibitory RNA operably linked to a developmentally regulated promoter active in germ cells of the embryo during at least a portion of a developmental stage corresponding to embryonic day 6 to embryonic day 14 in mice, to ablate the endogenous germ cells of the embryo; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes wherein the preimplantation non-human host embryo includes a transgene, the transgene including a nucleic acid sequence encoding a recombinase linked to a developmentally regulated promoter active in germ cells of the embryo during at least a portion of a developmental stage corresponding to embryonic day 6 to embryonic day 14 in mice, to ablate the endogenous germ cells of the embryo; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation rodent host embryo incapable of developing endogenous gametes wherein the preimplantation rodent host embryo includes a transgene, the transgene including a nucleic acid sequence encoding a cytotoxic protein operably linked to a developmentally regulated promoter active in germ cells of the embryo during at least a portion of a developmental stage corresponding to embryonic day 6 to embryonic day 14 of a mouse embryo, to ablate the endogenous germ cells of the embryo; b) introducing donor stem cells into the preimplantation rodent host embryo; and c) gestating the rodent host embryo of b) under conditions suitable for development of the embryo, thereby generating a chimeric rodent having substantially all gametes and/or germ cells derived from the donor stem cells.

Methods of generating a chimeric non-human animal are provided according to embodiments of the present invention which include: a) generating a preimplantation rodent host embryo incapable of developing endogenous gametes wherein the preimplantation rodent host embryo includes a transgene, the transgene including a nucleic acid sequence encoding an inhibitory RNA operably linked to a developmentally regulated promoter active in germ cells of the embryo during at least a portion of a developmental stage corresponding to embryonic day 6 to embryonic day 14 of a mouse embryo, to ablate the endogenous germ cells of the embryo; b) introducing donor stem cells into the preimplantation rodent host embryo; and c) gestating the rodent host embryo of b) under conditions suitable for development of the embryo, thereby generating a chimeric rodent having substantially all gametes and/or germ cells derived from the donor stem cells.

Methods of generating a chimeric non-human animal are provided according to embodiments of the present invention which include: a) generating a preimplantation rodent host embryo incapable of developing endogenous gametes wherein the preimplantation rodent host embryo includes a recombinase operably linked to a developmentally regulated promoter active in germ cells of the embryo during at least a portion of a developmental stage corresponding to embryonic day 6 to embryonic day 14 of a mouse embryo, to ablate the endogenous germ cells of the embryo; b) introducing donor stem cells into the preimplantation rodent host embryo; and c) gestating the rodent host embryo of b) under conditions suitable for development of the embryo, thereby generating a chimeric rodent having substantially all gametes and/or germ cells derived from the donor stem cells.

Methods of generating a chimeric non-human animal are provided according to embodiments of the present invention which include: a) generating a preimplantation mouse host embryo incapable of developing endogenous gametes wherein the preimplantation mouse host embryo includes a transgene, the transgene including a nucleic acid sequence encoding a cytotoxic protein operably linked to a developmentally regulated promoter active in germ cells of the embryo during a portion of embryonic day 6 to embryonic day 14 of a mouse embryo, to ablate the endogenous germ cells of the embryo; b) introducing donor stem cells into the preimplantation mouse host embryo; and c) gestating the mouse host embryo of b) under conditions suitable for development of the embryo, thereby generating a chimeric mouse having substantially all gametes and/or germ cells derived from the donor stem cells.

Methods of generating a chimeric non-human animal are provided according to embodiments of the present invention which include: a) generating a preimplantation mouse host embryo incapable of developing endogenous gametes wherein the preimplantation mouse host embryo includes a transgene, the transgene including a nucleic acid sequence encoding an inhibitory RNA operably linked to a developmentally regulated promoter active in germ cells of the embryo during a portion of embryonic day 6 to embryonic day 14 of a mouse embryo, to ablate the endogenous germ cells of the embryo; b) introducing donor stem cells into the preimplantation mouse host embryo; and c) gestating the mouse host embryo of b) under conditions suitable for development of the embryo, thereby generating a chimeric mouse having substantially all gametes and/or germ cells derived from the donor stem cells.

Methods of generating a chimeric non-human animal are provided according to embodiments of the present invention which include: a) generating a preimplantation mouse host embryo incapable of developing endogenous gametes wherein the preimplantation mouse host embryo includes a recombinase operably linked to a developmentally regulated promoter active in germ cells of the embryo during a portion of embryonic day 6 to embryonic day 14 of a mouse embryo, to ablate the endogenous germ cells of the embryo; b) introducing donor stem cells into the preimplantation mouse host embryo; and c) gestating the mouse host embryo of b) under conditions suitable for development of the embryo, thereby generating a chimeric mouse having substantially all gametes and/or germ cells derived from the donor stem cells.

Methods of generating a chimeric non-human animal are provided according to embodiments of the present invention which include: a) generating a preimplantation rat host embryo incapable of developing endogenous gametes wherein the preimplantation rat host embryo includes a transgene, the transgene including a nucleic acid sequence encoding a cytotoxic protein operably linked to a developmentally regulated promoter active in germ cells of the embryo during a portion of embryonic day 7 to embryonic day 16 of a rat embryo, to ablate the endogenous germ cells of the embryo; b) introducing donor stem cells into the preimplantation rat host embryo; and c) gestating the rat host embryo of b) under conditions suitable for development of the embryo, thereby generating a chimeric rat having substantially all gametes and/or germ cells derived from the donor stem cells.

Methods of generating a chimeric non-human animal are provided according to embodiments of the present invention which include: a) generating a preimplantation rat host embryo incapable of developing endogenous gametes wherein the preimplantation rat host embryo includes a transgene, the transgene including a nucleic acid sequence encoding an inhibitory RNA operably linked to a developmentally regulated promoter active in germ cells of the embryo during a portion of embryonic day 7 to embryonic day 16 of a rat embryo, to ablate the endogenous germ cells of the embryo; b) introducing donor stem cells into the preimplantation rat host embryo; and c) gestating the rat host embryo of b) under conditions suitable for development of the embryo, thereby generating a chimeric rat having substantially all gametes and/or germ cells derived from the donor stem cells.

Methods of generating a chimeric non-human animal are provided according to embodiments of the present invention which include: a) generating a preimplantation rat host embryo incapable of developing endogenous gametes wherein the preimplantation rat host embryo includes a recombinase operably linked to a developmentally regulated promoter active in germ cells of the embryo during a portion of embryonic day 7 to embryonic day 16 of a rat embryo, to ablate the endogenous germ cells of the embryo; b) introducing donor stem cells into the preimplantation rat host embryo; and c) gestating the rat host embryo of b) under conditions suitable for development of the embryo, thereby generating a chimeric rat having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes by expression of a transgene, the transgene including a nucleic acid sequence encoding a cytotoxic protein operably linked to a developmentally regulated promoter or a ubiquitous promoter, the transgene further including at least one cytotoxic protein inhibitory sequence operably linked to at least two recombinase recognition sites; wherein the non-human host embryo further includes a second transgene including a nucleic acid sequence encoding a recombinase, the nucleic acid sequence encoding the recombinase operably linked to a promoter selected from the group consisting of: a developmentally regulated promoter and a ubiquitous promoter, wherein at least either the first or second transgene is operably linked to a developmentally regulated promoter; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes by expression of a transgene, the transgene including a nucleic acid sequence encoding an inhibitory RNA operably linked to a developmentally regulated promoter or a ubiquitous promoter, the transgene further including at least one inhibitory RNA inhibitory sequence and operably linked to at least two recombinase recognition sites; wherein the non-human host embryo further includes a second transgene including a nucleic acid sequence encoding a recombinase, the nucleic acid sequence encoding the recombinase operably linked to a promoter selected from the group consisting of: a developmentally regulated promoter and a ubiquitous promoter, wherein at least either the first or second transgene is operably linked to a developmentally regulated promoter; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes wherein the preimplantation non-human host embryo includes a transgene, the transgene including a nucleic acid sequence encoding a cytotoxic protein, an inhibitory RNA or a recombinase, wherein the nucleic acid sequence encodes a cytotoxic protein, an inhibitory RNA or a recombinase operably linked to an inducible promoter, to ablate the endogenous germ cells of the embryo; b) introducing donor stem cells into the preimplantation non-human host embryo; and c) gestating the non-human host embryo of b) under conditions suitable for development of the embryo, thereby generating a chimeric non-human animal having 80% or more gametes and/or germ cells of the chimeric non-human animal are derived from the donor stem cells.

Methods of generating a chimeric non-human animal are provided according to embodiments of the present invention which include: a) generating a preimplantation non-human host embryo incapable of developing endogenous gametes by expression of a first transgene, the first transgene including a nucleic acid sequence encoding a cytotoxic protein operably linked to a ubiquitous promoter or a developmentally regulated promoter selected from the group consisting of: vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, and Tiar promoter, the transgene further including at least one cytotoxic protein inhibitory sequence and operably linked to at least two recombinase recognition sites; wherein the non-human host embryo further includes a second transgene including a nucleic acid sequence encoding a recombinase, the nucleic acid sequence encoding the recombinase operably linked to a ubiquitous promoter or a developmentally regulated promoter selected from the group consisting of: vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, and Tiar promoter, wherein at least either the first or second transgene is operably linked to a developmentally regulated promoter; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes by expression of a first transgene, the first transgene including a nucleic acid sequence encoding an inhibitory RNA operably linked to a ubiquitous promoter or a developmentally regulated promoter selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, the transgene further including at least one cytotoxic protein inhibitory sequence and operably linked to at least two recombinase recognition sites; wherein the non-human host embryo further includes a second transgene including a nucleic acid sequence encoding a recombinase, the nucleic acid sequence encoding the recombinase operably linked to a ubiquitous promoter or a developmentally regulated promoter selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, wherein at least either the first or second transgene is operably linked to a developmentally regulated promoter; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes wherein the preimplantation non-human host embryo includes a transgene, the transgene including a nucleic acid sequence encoding a cytotoxic protein operably linked to a developmentally regulated promoter active in germ cells of the embryo during at least a portion of a developmental stage corresponding to embryonic day 6 to embryonic day 14 in mice selected from the group consisting of: vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, and Tiar promoter, to ablate the endogenous germ cells of the embryo; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes wherein the preimplantation non-human host embryo includes a transgene, the transgene including a nucleic acid sequence encoding an inhibitory RNA operably linked to a developmentally regulated promoter active in germ cells of the embryo during at least a portion of a developmental stage corresponding to embryonic day 6 to embryonic day 14 in mice selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, to ablate the endogenous germ cells of the embryo; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes wherein the preimplantation non-human host embryo includes a recombinase linked to a developmentally regulated promoter active in germ cells of the embryo during at least a portion of a developmental stage corresponding to embryonic day 6 to embryonic day 14 in mice selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, to ablate the endogenous germ cells of the embryo; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include, optionally, donor stem cells derived from a first animal species and a preimplantation non-human host embryo of a different second animal species. In one option, the donor stem cells are rat stem cells and the preimplantation non-human host embryo is a mouse embryo, such that rat gametes and/or rat germ cells are produced in a mouse host animal.

Methods of generating a chimeric non-human animal are provided according to embodiments of the present invention which include: a) generating a preimplantation non-human host embryo incapable of developing endogenous gametes wherein the preimplantation non-human host embryo includes a transgene, the transgene including a nucleic acid sequence encoding Herpes simplex virus thymidine kinase operably linked to a developmentally regulated promoter active in germ cells of the embryo during at least a portion of a developmental stage corresponding to embryonic day 6 to embryonic day 14 in mice and further comprising contacting endogenous germ cells expressing the Herpes simplex virus thymidine kinase with a thymidine analog to ablate the endogenous germ cells of the embryo; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of endogenous gametes wherein the preimplantation non-human host embryo includes a transgene, the transgene including a nucleic acid sequence encoding a functional mutant or truncated Herpes simplex virus thymidine kinase operably linked to a developmentally regulated promoter active in germ cells of the embryo during at least a portion of a developmental stage corresponding to embryonic day 6 to embryonic day 14 in mice and further comprising contacting endogenous germ cells expressing the a functional mutant or truncated Herpes simplex virus thymidine kinase with a thymidine analog to ablate the endogenous germ cells of the embryo; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of producing a chimeric non-human animal are provided according to embodiments of the present invention which include: a) generating a preimplantation non-human host embryo incapable of developing endogenous gametes wherein the preimplantation non-human host embryo includes a transgene, the transgene including a nucleic acid sequence encoding Herpes simplex virus thymidine kinase operably linked to a developmentally regulated promoter active in germ cells of the embryo during at least a portion of a developmental stage corresponding to embryonic day 6 to embryonic day 14 in mice selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, and further comprising contacting endogenous germ cells expressing the Herpes simplex virus thymidine kinase with a thymidine analog to ablate the endogenous germ cells of the embryo; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes wherein the preimplantation non-human host embryo includes a transgene, the transgene including a nucleic acid sequence encoding Herpes simplex virus thymidine kinase operably linked to a developmentally regulated promoter active in germ cells of the embryo during at least a portion of a developmental stage corresponding to embryonic day 6 to embryonic day 14 in mice selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, and further comprising contacting endogenous germ cells expressing the Herpes simplex virus thymidine kinase with a thymidine analog selected from the group consisting of: ganciclovir, acyclovir and fialuridine, to ablate the endogenous germ cells of the embryo; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes by expressing diphtheria toxin A fragment, attenuated diphtheria toxin A fragment, tox-176; or a cytotoxic homologue, fragment or variant thereof, in germ cells of the non-human host embryo to ablate endogenous germ cells; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Methods of generating a chimeric non-human animal are provided according to embodiments of the present invention which include: a) generating a preimplantation non-human host embryo incapable of developing endogenous gametes by expression of a first transgene, the first transgene including a nucleic acid sequence encoding diphtheria toxin A fragment, attenuated DTA or tox-176; or a cytotoxic homologue, fragment or variant thereof, operably linked to a ubiquitous promoter or a developmentally regulated promoter selected from the group consisting of: vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, and Tiar promoter, the transgene further including at least one inhibitory sequence for diphtheria toxin A fragment, attenuated DTA, tox-176 or a cytotoxic homologue, fragment or variant thereof, and operably linked to at least two recombinase recognition sites; wherein the non-human host embryo further includes a second transgene including a nucleic acid sequence encoding a recombinase, the nucleic acid sequence encoding the recombinase operably linked to a ubiquitous promoter or a developmentally regulated promoter selected from the group consisting of: vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, and Tiar promoter, wherein at least either the first or second transgene is operably linked to a developmentally regulated promoter; b) introducing donor stem cells into the preimplantation non-human host embryo; and c) gestating the non-human host embryo of b) under conditions suitable for development of the embryo, thereby generating a chimeric non-human animal having substantially all gametes and/or germ cells derived from the donor stem cells.

Non-human host embryos are provided according to embodiments of the present invention which include a transgene encoding a deleter gene, the transgene configured to express a cytotoxic protein or inhibitory RNA in endogenous germ cells of the embryo.

Non-human host embryos are provided according to embodiments of the present invention which include a nucleic acid sequence encoding a cytotoxic protein operably linked to a developmentally regulated promoter active in germ cells of the embryo during at least a portion of a developmental stage corresponding to embryonic day 6 to embryonic day 14 of a mouse embryo.

Non-human host embryos are provided according to embodiments of the present invention which include a nucleic acid sequence encoding an inhibitory RNA operably linked to a developmentally regulated promoter active in germ cells of the embryo during at least a portion of a developmental stage corresponding to embryonic day 6 to embryonic day 14 of a mouse embryo.

Host rodent embryos are provided according to embodiments of the present invention which include a nucleic acid sequence encoding a cytotoxic protein operably linked to a developmentally regulated promoter active in germ cells of the embryo during at least a portion of a developmental stage corresponding to embryonic day 6 to embryonic day 14 of a mouse embryo.

Host rodent embryos are provided according to embodiments of the present invention which include a nucleic acid sequence encoding an inhibitory RNA operably linked to a developmentally regulated promoter active in germ cells of the embryo during at least a portion of a developmental stage corresponding to embryonic day 6 to embryonic day 14 of a mouse embryo.

Host mouse embryos are provided according to embodiments of the present invention which include a nucleic acid sequence encoding a cytotoxic protein operably linked to a developmentally regulated promoter active in germ cells of the embryo during at least a portion of a developmental stage corresponding to embryonic day 6 to embryonic day 14 of a mouse embryo.

Host mouse embryos are provided according to embodiments of the present invention which include a nucleic acid sequence encoding an inhibitory RNA operably linked to a developmentally regulated promoter active in germ cells of the embryo during at least a portion of a developmental stage corresponding to embryonic day 6 to embryonic day 14 of a mouse embryo.

Host rat embryos are provided according to embodiments of the present invention which include a nucleic acid sequence encoding a cytotoxic protein operably linked to a developmentally regulated promoter active in germ cells of the embryo during at least a portion of embryonic day 7 to embryonic day 16 of the rat embryo.

Host rat embryos are provided according to embodiments of the present invention which include a nucleic acid sequence encoding an inhibitory RNA operably linked to a developmentally regulated promoter active in germ cells of the embryo during at least a portion of embryonic day 7 to embryonic day 16 of the rat embryo.

Non-human host embryos are provided according to embodiments of the present invention which include a transgene including a nucleic acid sequence encoding a cytotoxic protein operably linked to a developmentally regulated promoter or a ubiquitous promoter, the transgene further including at least one cytotoxic protein inhibitory sequence and operably linked to at least two recombinase recognition sites; wherein the non-human host embryo further includes a second transgene including a nucleic acid sequence encoding a recombinase, the nucleic acid sequence encoding the recombinase operably linked to a promoter selected from the group consisting of: a developmentally regulated promoter and a ubiquitous promoter, wherein at least either the first or second transgene is operably linked to a developmentally regulated promoter.

Non-human host embryos are provided according to embodiments of the present invention which include a first transgene including a nucleic acid sequence encoding a cytotoxic protein operably linked to a developmentally regulated promoter selected from the group consisting of: vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, and Tiar promoter, or a ubiquitous promoter, the first transgene further including at least one cytotoxic protein inhibitory sequence and operably linked to at least two recombinase recognition sites; wherein the non-human host embryo further includes a second transgene including a nucleic acid sequence encoding a recombinase, the nucleic acid sequence encoding the recombinase operably linked to a developmentally regulated promoter selected from the group consisting of: vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, and Tiar promoter, or a ubiquitous promoter, wherein at least either the first or second transgene is operably linked to a developmentally regulated promoter.

Non-human host embryos are provided according to embodiments of the present invention which include a first transgene including a nucleic acid sequence encoding an inhibitory RNA operably linked to a developmentally regulated promoter selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, or a ubiquitous promoter, the first transgene further including at least one inhibitory RNA inhibitory sequence and operably linked to at least two recombinase recognition sites; wherein the non-human host embryo further includes a second transgene including a nucleic acid sequence encoding a recombinase, the nucleic acid sequence encoding the recombinase operably linked to a developmentally regulated promoter selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, or a ubiquitous promoter, wherein at least either the first or second transgene is operably linked to a developmentally regulated promoter.

Non-human host embryos are provided according to embodiments of the present invention which include a transgene including a nucleic acid sequence encoding a cytotoxic protein operably linked to an inducible promoter or a ubiquitous promoter, the transgene further including at least one cytotoxic protein inhibitory sequence and operably linked to at least two recombinase recognition sites; wherein the non-human host embryo further includes a second transgene including a nucleic acid sequence encoding a recombinase, the nucleic acid sequence encoding the recombinase operably linked to a promoter selected from the group consisting of: an inducible promoter and a ubiquitous promoter, wherein at least either the first or second transgene is operably linked to an inducible promoter.

Non-human host embryos are provided according to embodiments of the present invention which include a nucleic acid sequence encoding a cytotoxic protein operably linked to a developmentally regulated promoter active in germ cells of the embryo during at least a portion of a developmental stage corresponding to embryonic day 6 to embryonic day 14 of a mouse embryo selected from vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, or Tiar promoter.

Non-human host embryos are provided according to embodiments of the present invention which are incapable of developing endogenous gametes due to ablation of germ cells as described herein. The non-human host incapable of developing endogenous gametes due to ablation of germ cells can be embryos of any non-human mammal including, but not limited to, any rodent, mouse, rat non-human primate, marmoset, rabbit, dog, cat, cattle, horse, sheep, goat, an endangered mammal or an exotic mammal.

Non-human host embryos are provided according to embodiments of the present invention which include a transgene which includes a nucleic acid sequence encoding a Herpes simplex virus thymidine kinase operably linked to a developmentally regulated promoter active in germ cells of the embryo during at least a portion of a developmental stage corresponding to embryonic day 6 to embryonic day 14 of a mouse embryo. The endogenous germ cells expressing the Herpes simplex virus thymidine kinase are contacted with a thymidine analog to ablate the endogenous germ cells.

Non-human host embryos are provided according to embodiments of the present invention which include a transgene which includes a nucleic acid sequence encoding a diphtheria toxin A fragment, attenuated DTA, tox-176 or a cytotoxic homologue, fragment or variant thereof, operably linked to vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, or Tiar promoter. The endogenous germ cells expressing the Herpes simplex virus thymidine kinase are contacted with a thymidine analog to ablate the endogenous germ cells.

Non-human host embryos are provided according to embodiments of the present invention which include a transgene which includes a nucleic acid sequence encoding a Herpes simplex virus thymidine kinase operably linked to vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter or TNAP promoter. The endogenous germ cells expressing the Herpes simplex virus thymidine kinase are contacted with a thymidine analog to ablate the endogenous germ cells.

Methods of producing a non-human host embryo incapable of developing endogenous gametes are provided according to embodiments of the present invention which include introducing a transgene encoding a cytotoxic protein or RNA interference molecule into the embryo; and expressing the transgene in endogenous germ cells of the embryo, thereby producing a non-human embryo lacking functional endogenous germ cells.

Methods of producing a non-human host embryo incapable of developing endogenous gametes are provided according to embodiments of the present invention which include introducing a transgene including a nucleic acid sequence encoding a cytotoxic protein operably linked to a developmentally regulated promoter active in germ cells of the embryo during at least a portion of a developmental stage corresponding to embryonic day 6 to embryonic day 14 in mice. The transgene is expressed in endogenous germ cells of the embryo, thereby producing a non-human embryo lacking functional endogenous germ cells.

Methods of producing a non-human host embryo incapable of developing endogenous gametes are provided according to embodiments of the present invention which include introducing a transgene including a nucleic acid sequence encoding an inhibitory RNA operably linked to a developmentally regulated promoter active in germ cells of the embryo during at least a portion of a developmental stage corresponding to embryonic day 6 to embryonic day 14 in mice. The transgene is expressed in endogenous germ cells of the embryo, thereby producing a non-human embryo lacking functional endogenous germ cells.

Methods of producing a host rodent embryo incapable of developing endogenous gametes are provided according to embodiments of the present invention which include introducing a transgene including a nucleic acid sequence encoding a cytotoxic protein operably linked to a developmentally regulated promoter active in germ cells of the rodent embryo during at least a portion of a developmental stage corresponding to embryonic day 6 to embryonic day 14 in mice. The transgene is expressed in endogenous germ cells of the rodent embryo, thereby producing a rodent embryo lacking functional endogenous germ cells.

Methods of producing a host rodent embryo incapable of developing endogenous gametes are provided according to embodiments of the present invention which include introducing a transgene including a nucleic acid sequence encoding an inhibitory RNA operably linked to a developmentally regulated promoter active in germ cells of the rodent embryo during at least a portion of a developmental stage corresponding to embryonic day 6 to embryonic day 14 in mice. The transgene is expressed in endogenous germ cells of the rodent embryo, thereby producing a rodent embryo lacking functional endogenous germ cells.

Methods of producing a mouse embryo incapable of developing endogenous gametes are provided according to embodiments of the present invention which include introducing a transgene including a nucleic acid sequence encoding a cytotoxic protein operably linked to a developmentally regulated promoter active in germ cells of the mouse embryo during at least a portion of a developmental stage corresponding to embryonic day 6 to embryonic day 14 in mice. The transgene is expressed in endogenous germ cells of the mouse embryo, thereby producing a mouse embryo lacking functional endogenous germ cells.

Methods of producing a host mouse embryo incapable of developing endogenous gametes are provided according to embodiments of the present invention which include introducing a transgene including a nucleic acid sequence encoding an inhibitory RNA operably linked to a developmentally regulated promoter active in germ cells of the mouse embryo during at least a portion of a developmental stage corresponding to embryonic day 6 to embryonic day 14 in mice. The transgene is expressed in endogenous germ cells of the mouse embryo, thereby producing a mouse embryo lacking functional endogenous germ cells.

Methods of producing a rat rodent embryo incapable of developing endogenous gametes are provided according to embodiments of the present invention which include introducing a transgene including a nucleic acid sequence encoding a cytotoxic protein operably linked to a developmentally regulated promoter active in germ cells of the rat embryo during at least a portion of embryonic day 7 to embryonic day 16 of the rat embryo. The transgene is expressed in endogenous germ cells of the rat embryo, thereby producing a rat embryo lacking functional endogenous germ cells.

Methods of producing a host rat embryo incapable of developing endogenous gametes are provided according to embodiments of the present invention which include introducing a transgene including a nucleic acid sequence encoding an inhibitory RNA operably linked to a developmentally regulated promoter active in germ cells of the rat embryo during at least a portion of embryonic day 7 to embryonic day 16 of the rat embryo. The transgene is expressed in endogenous germ cells of the rat embryo, thereby producing a rat embryo lacking functional endogenous germ cells.

Methods of producing a mouse embryo incapable of developing endogenous gametes are provided according to embodiments of the present invention which include introducing a first transgene including a nucleic acid sequence encoding a cytotoxic protein operably linked to a developmentally regulated promoter or a ubiquitous promoter, the transgene further including at least one cytotoxic protein inhibitory sequence and operably linked to at least two recombinase recognition sites; wherein the non-human host embryo further comprises a second transgene comprising a nucleic acid sequence encoding a recombinase, the nucleic acid sequence encoding the recombinase operably linked to a promoter selected from the group consisting of: a developmentally regulated promoter and a ubiquitous promoter, wherein at least either the first or second transgene is operably linked to a developmentally regulated promoter.

Methods of producing a mouse embryo incapable of developing endogenous gametes are provided according to embodiments of the present invention which include introducing a first transgene including a nucleic acid sequence encoding a cytotoxic protein operably linked to a developmentally regulated promoter selected from vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, and Tiar promoter, or a ubiquitous promoter, the transgene further including at least one cytotoxic protein inhibitory sequence and operably linked to at least two recombinase recognition sites; wherein the non-human host embryo further comprises a second transgene comprising a nucleic acid sequence encoding a recombinase, the nucleic acid sequence encoding the recombinase operably linked to a developmentally regulated promoter selected from vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, and Tiar promoter, and a ubiquitous promoter, wherein at least either the first or second transgene is operably linked to a developmentally regulated promoter.

Methods of producing a mouse embryo incapable of developing endogenous gametes are provided according to embodiments of the present invention which include introducing a first transgene including a nucleic acid sequence encoding an inhibitory RNA operably linked to a developmentally regulated promoter or a ubiquitous promoter, the transgene further including at least one inhibitory RNA inhibitory sequence and operably linked to at least two recombinase recognition sites; wherein the non-human host embryo further comprises a second transgene comprising a nucleic acid sequence encoding a recombinase, the nucleic acid sequence encoding the recombinase operably linked to a promoter selected from the group consisting of: a developmentally regulated promoter and a ubiquitous promoter, wherein at least either the first or second transgene is operably linked to a developmentally regulated promoter.

Methods of producing a mouse embryo incapable of developing endogenous gametes are provided according to embodiments of the present invention which include introducing a first transgene including a nucleic acid sequence encoding an inhibitory RNA operably linked to a developmentally regulated promoter selected from vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct314 promoter, Prdm1 promoter, Prdm14 promoter, Tex13 promoter, Tiar promoter and TNAP promoter, or a ubiquitous promoter, the transgene further including at least one inhibitory RNA inhibitory sequence and operably linked to at least two recombinase recognition sites; wherein the non-human host embryo further comprises a second transgene comprising a nucleic acid sequence encoding a recombinase, the nucleic acid sequence encoding the recombinase operably linked to a developmentally regulated promoter selected from vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter, or a ubiquitous promoter, wherein at least either the first or second transgene is operably linked to a developmentally regulated promoter.

Methods of producing a non-human host embryo incapable of developing endogenous gametes are provided according to embodiments of the present invention which include introducing a transgene including a nucleic acid sequence encoding a cytotoxic protein or RNA interference molecule into the embryo, the nucleic acid sequence operably linked to an inducible promoter; and expressing, the transgene in endogenous germ cells of the embryo, thereby producing a non-human embryo lacking functional endogenous germ cells.

Methods of producing a non-human host embryo incapable of developing endogenous gametes are provided according to embodiments of the present invention which include introducing a transgene including a nucleic acid sequence encoding a cytotoxic protein or an inhibitory RNA, the nucleic acid sequence encoding the cytotoxic protein or the inhibitory RNA operably linked to a developmentally regulated promoter active in germ cells of the embryo during at least a portion of a developmental stage corresponding to embryonic day 6 to embryonic day 14 in mice selected from the group consisting of: vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter and TNAP promoter.

Methods of producing a non-human host embryo lacking endogenous germ cells are provided according to embodiments of the present invention which include introducing a transgene encoding Herpes simplex virus thymidine kinase into the embryo; expressing the transgene in endogenous germ cells of the embryo, thereby producing a non-human embryo lacking functional endogenous germ cells; contacting endogenous germ cells expressing the Herpes simplex virus thymidine kinase with a thymidine analog to ablate the endogenous germ cells.

Methods of producing a non-human host embryo lacking endogenous germ cells are provided according to embodiments of the present invention which include introducing a transgene encoding Herpes simplex virus thymidine kinase operably linked to a developmentally regulated promoter into the embryo; expressing the transgene in endogenous germ cells of the embryo, thereby producing a non-human embryo lacking functional endogenous germ cells; contacting endogenous germ cells expressing the Herpes simplex virus thymidine kinase with ganciclovir, acyclovir or fialuridine to ablate the endogenous germ cells.

A combination of any two or more thymidine analogs, such as a combination of any two or more of ganciclovir, acyclovir and fialuridine, can be used.

Methods of producing a non-human host embryo lacking endogenous germ cells are provided according to embodiments of the present invention which include introducing a transgene encoding Herpes simplex virus thymidine kinase operably linked vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter or TNAP promoter, into the embryo; expressing the transgene in endogenous germ cells of the embryo, thereby producing a non-human embryo lacking functional endogenous germ cells; and contacting endogenous germ cells expressing the Herpes simplex virus thymidine kinase with ganciclovir, acyclovir or fialuridine to ablate the endogenous germ cells.

Methods of producing a non-human host embryo incapable of developing endogenous gametes are provided according to embodiments of the present invention which include introducing a transgene encoding diphtheria toxin A fragment, attenuated DTA, tox-176, or a cytotoxic homologue, fragment or variant thereof, operably linked to vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, or Tiar promoter, into the embryo; and expressing the transgene in endogenous germ cells of the embryo, thereby producing a non-human embryo lacking functional endogenous germ cells.

Non-human host embryos incapable of developing endogenous gametes are provided according to embodiments of the present invention, the non-human host embryos including a transgene encoding a recombinase operably linked to a developmentally regulated promoter active in germ cells and a transgene encoding diphtheria toxin operably linked to a ubiquitous promoter, wherein the transgene encoding diphtheria toxin operably linked to a ubiquitous promoter having a loxP-flanked stop cassette and operably linked to at least two recombinase recognition sites.

Non-human host embryos incapable of developing endogenous gametes are provided according to embodiments of the present invention, the non-human host embryos including a first transgene encoding a recombinase operably linked to a developmentally regulated promoter active in germ cells selected from vasa promoter, Dnd1 promoter, Fkbp6 promoter, Fragilis promoter, Fragilis-2 promoter, GDF-3 promoter, Mov1011 promoter, Nanos2 promoter, Nanos3 promoter, Prdm1 promoter, Tex13 promoter, and Tiar promoter; and a second transgene encoding: a loxP-flanked stop cassette operably linked to a nucleic acid sequence encoding diphtheria toxin A fragment, attenuated DTA, tox-176, or a cytotoxic homologue, fragment or variant thereof. The nucleic acid sequence encoding diphtheria toxin A fragment, attenuated DTA, tox-176, or a cytotoxic homologue, fragment or variant thereof is operably linked to a ubiquitous promoter. The loxP-flanked stop cassette is operably linked to at least two recombinase recognition sites such that expression of the recombinase is effective to excise the stop cassette such that the diphtheria toxin A fragment, attenuated DTA, tox-176, or a cytotoxic homologue, fragment or variant thereof operably linked to a ubiquitous promoter is expressed in the germ cells, thereby ablating the germ cells.

Non-human host embryos incapable of developing endogenous gametes are provided according to embodiments of the present invention, the non-human host embryos including a transgene encoding a recombinase operably linked to a vasa promoter and a transgene encoding diphtheria toxin operably linked to a ubiquitous promoter, wherein the transgene encoding diphtheria toxin is operably linked to a ubiquitous promoter having a loxP-flanked stop cassette and operably linked to at least two recombinase recognition sites.

Non-human host embryos incapable of developing endogenous gametes are provided according to embodiments of the present invention, the non-human host embryos including a first transgene encoding a recombinase operably linked to a vasa promoter; and a second transgene encoding: a loxP-flanked stop cassette operably linked to a nucleic acid sequence encoding diphtheria toxin A fragment, attenuated DTA, tox-176, or a cytotoxic homologue, fragment or variant thereof. The nucleic acid sequence encoding diphtheria toxin A fragment, attenuated DTA, tox-176, or a cytotoxic homologue, fragment or variant thereof is operably linked to a ubiquitous promoter. The loxP-flanked stop cassette is operably linked to at least two recombinase recognition sites such that expression of the recombinase is effective to excise the stop cassette such that the diphtheria toxin A fragment, attenuated DTA, tox-176, or a cytotoxic homologue, fragment or variant thereof operably linked to a ubiquitous promoter is expressed in the germ cells, thereby ablating the germ cells.

Methods of producing a non-human host embryo incapable of developing endogenous gametes are provided according to embodiments of the present invention which include breeding a first animal of a first rodent strain comprising a transgene encoding a recombinase operably linked to a developmentally regulated promoter and a second animal of a second rodent strain carrying a transgene with recombinase recognition sites operably linked to a nucleic acid sequence encoding a cytotoxic protein or inhibitory RNA operably linked to a ubiquitous or developmentally regulated promoter.

Methods of producing a non-human host embryo incapable of developing endogenous gametes are provided according to embodiments of the present invention which include breeding a first mouse strain comprising a transgene encoding Cre recombinase operably linked with a vasa promoter and a second mouse strain comprising a loxP-flanked stop cassette operatively linked with a transgene encoding diphtheria toxin, such as diphtheria toxin A fragment, attenuated DTA, tox-176, or a cytotoxic homologue, fragment or variant thereof, operably linked with a ubiquitous or developmentally regulated promoter.

DETAILED DESCRIPTION OF THE INVENTION

Figure 1:
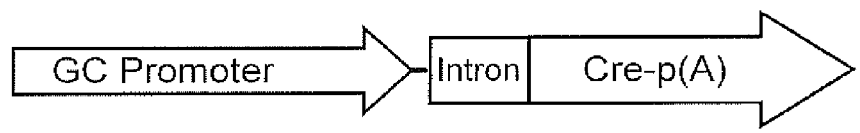
FIG. 1 is a schematic representation of a DNA expression construct containing a site specific recombinase gene to create an activator mouse strain; sequence lengths are not drawn to scale.

Compositions and methods are provided according to the present invention relating to non-human animals modified to promote production of selected germ cells and gametes from exogenous stem cells.

Modified non-human host embryos and methods for producing the modified non-human host embryos are provided by the present invention. Germ cells originating in the non-human host embryos are manipulated such that they are not capable of proliferation and/or differentiation into gametes. Modified non-human host embryos are used to "host" introduced donor stem cells which populate the germ cell layer, resulting in chimeric non-human animals in which the germ cells and gametes are all or substantially all from donor stem cells.

Methods and compositions are provided according to embodiments of the present invention for generation of chimeric non-human animals in which the germ cells and/or gametes are all or substantially all from donor stem cells. Thus, methods and compositions are provided for generation of chimeric non-human animals in which the germ cells and/or gametes are 80% or greater derived from donor stem cells.

Methods of generating a chimeric non-human embryo or animal in which the germ cells and/or gametes are all or substantially all derived from donor stem cells include generating a non-human host embryo lacking functional germ cells. Such methods further include introduction of donor stem cells into the non-human host embryo before ablation of the germ cells endogenous to the non-human host embryo. The non-human host embryo lacking functional endogenous germ cells and including introduced donor stem cells is gestated under conditions suitable for development of the embryo, thereby generating a chimeric non-human animal having substantially all germ cells and/or gametes derived from the donor stem cells. The germ cells and gametes can then be used to make a non-human embryo or animal derived from the donor stem cells.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, Pa., 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer (Eds) 2002, Manipulating the Mouse Embryo: A Laboratory Manual, 3$^{rd}$ edition, Cold Spring Harbor Laboratory Press, ISBN-10: 0879695919; K. Turksen (Ed.), Embryonic stem cells: methods and protocols in Methods Mol. Biol. 2002; 185, Humana Press; Current Protocols in Stem Cell Biology, ISBN: 9780470151808.

The singular terms "a," "an," and "the" are not intended to be limiting and include plural referents unless explicitly state or the context clearly indicates otherwise.

The terms "germ cell" and "germ cells" are used interchangeably and refer to cells that give rise to gametes. The term "germ cells" includes primordial germ cells, cells positive for alkaline phosphatase, primary oocytes, oogonia, spermatogonial stem cells, spermatogonia and primary spermatocytes.

The terms "gamete" and "gametes" are used interchangeably and refer to secondary germ cells, including oocytes, ova, spermatozoa and sperm.

The term "breeding" as used herein, means the union of male and female gametes so that fertilization occurs. Such a union may be brought about by mating (copulation) or by in vitro or in vivo artificial methods. Such artificial methods include, but are not limited to, artificial insemination, surgical assisted artificial insemination, in vitro fertilization, intracytoplasmic sperm injection, zona drilling, in vitro culture of fertilized oocytes, ovary transfer and ovary splitting.

The term "transgenic" as used herein refers to a genetically modified non-human animal containing a transgene. The term "transgene" as used herein refers to a nucleic acid artificially inserted into the genome of a non-human animal, transiently, or more preferably, permanently introducing a genetic change in the non-human animal.

The term "genetically modified" as used herein refers to the introduction of DNA technology into a cell or organism.

Compositions and methods of the present invention are not limited to particular amino acid and nucleic sequences identified by SEQ ID NO herein and homologues and variants of a reference nucleic acid or protein may be used.

Homologues and variants of a nucleic acid or protein described herein are characterized by conserved functional properties compared to the corresponding nucleic acid or protein.

Percent identity is determined by comparison of amino acid or nucleic acid sequences, including a reference amino acid or nucleic acid sequence and a putative homologue amino acid or nucleic acid sequence. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). The two sequences compared are generally the same length or nearly the same length.

The determination of percent identity between two sequences can also be accomplished using a mathematical algorithm. Algorithms used for determination of percent identity illustratively include the algorithms of S. Karlin and S. Altshul, PNAS, 90:5873-5877, 1993; T. Smith and M. Waterman, Adv. Appl. Math. 2:482-489, 1981, S, Needleman and C. Wunsch, J. Mol. Biol., 48:443-453, 1970, W. Pearson and D. Lipman, PNAS, 85:2444-2448, 1988 and others incorporated into computerized implementations such as, but not limited to, GAP, BESTFIT, FASTA, TFASTA; and BLAST, for example incorporated in the Wisconsin Genetics Software Package, Genetics Computer Group, 575 Science Drive, Madison, Wis.) and publicly available from the National Center for Biotechnology Information.

A non-limiting example of a mathematical algorithm utilized for the comparison of two sequences is the algorithm of Karlin and Altschul, 1990, PNAS 87:2264-2268, modified as in Karlin and Altschul, 1993, PNAS. 90:5873-5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, word length=12 to obtain nucleotide sequences homologous to a nucleic acid molecules of the present invention. BLAST protein searches are performed with the XBLAST program parameters set, e.g., to score 50, word length=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389-3402. Alternatively, PSI BLAST is used to perform an iterated search which detects distant relationships between molecules. When utilizing BLAST, Gapped BLAST, and PSI Blast programs, the default parameters of the respective programs (e.g., of XBLAST and NBLAST) are used. Another preferred, non limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

One of skill in the art will recognize that one or more nucleic acid or amino acid mutations can be introduced without altering the functional properties of a given nucleic acid or protein, respectively. Mutations can be introduced using standard molecular biology techniques, such as site-directed mutagenesis and PCR-mediated mutagenesis, to produce variants. For example, one or more amino acid substitutions, additions, or deletions can be made without altering the functional properties of a reference protein. Similarly, one or more nucleic acid substitutions, additions, or deletions can be made without altering the functional properties of a reference promoter sequence.

When comparing a reference protein to a putative homologue, amino acid similarity may be considered in addition to identity of amino acids at corresponding positions in an amino acid sequence. "Amino acid similarity" refers to amino acid identity and conservative amino acid substitutions in a putative homologue compared to the corresponding amino acid positions in a reference protein.

Conservative amino acid substitutions can be made in reference proteins to produce variants.

Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

A variant can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

With regard to nucleic acids, it will be appreciated by those of skill in the art that due to the degenerate nature of the genetic code, multiple nucleic acid sequences can encode a particular protein, and that such alternate nucleic acids may be used in compositions and methods of the present invention.

The term "expression construct" is used herein to refer to a double-stranded recombinant DNA molecule containing a nucleic acid sequence desired to be expressed and containing appropriate regulatory elements necessary or desirable for the transcription of the operably linked nucleic acid sequence in vitro or in vivo. The term "recombinant" is used to indicate a nucleic acid construct in which two or more nucleic acids are linked and which are not found linked in nature. The term "nucleic acid" as used herein refers to RNA or DNA molecules having more than one nucleotide in any form including single-stranded, double-stranded, oligonucleotide or polynucleotide. The term "nucleotide sequence" is used to refer to the ordering of nucleotides in an oligonucleotide or polynucleotide in a single-stranded form of nucleic acid. The term "expressed" refers to transcription of a nucleic acid sequence to produce a corresponding mRNA and/or translation of the mRNA to produce the corresponding protein. Expression constructs can be generated recombinantly or synthetically or by DNA synthesis using well-known methodology.

An expression construct is introduced into a cell using well-known methodology, such as, but not limited to, by introduction of a vector containing the expression construct into the cell. A "vector" is a nucleic acid molecule that transfers an inserted nucleic acid molecule into and/or between host cells becoming self-replicating. The term includes vectors that function primarily for insertion of a nucleic acid molecule into a cell, replication of vectors that function primarily for the replication of nucleic acid, and expression vectors that function for transcription and/or translation of the DNA or RNA. Also included are vectors that provide more than one of the above functions.

Vectors include plasmids, viruses, BACs, YACs, and the like. Particular viral vectors illustratively include those derived from adenovirus, adeno-associated virus and lentivirus.

Any of various methods can be used to introduce a transgene into a non-human animal to produce a transgenic animal. Such techniques are well-known in the art and include, but are not limited to, pronuclear microinjection, viral infection and transformation of embryonic stem cells and iPS cells. Methods for generating transgenic animals that can be used include, but are not limited to, those described in J. P. Sundberg and T. Ichiki, Eds., Genetically Engineered Mice Handbook, CRC Press; 2006; M. H. Hofker and I. van Deursen, Eds., Transgenic Mouse Methods and Protocols, Humana Press, 2002; A. L. Joyner, Gene Targeting: A Practical Approach, Oxford University Press, 2000; Manipulating the Mouse Embryo: A Laboratory Manual, 3rd edition, Cold Spring Harbor Laboratory Press; 2002, ISBN-10: 0879695919; K. Turksen (Ed.), Embryonic stem cells: methods and protocols in Methods Mol. Biol. 2002; 185, Humana Press; Current Protocols in Stem Cell Biology, ISBN: 978047015180; Meyer et al. PNAS USA, vol. 107 (34), 15022-15026.

The term "regulatory element" as used herein refers to a nucleotide sequence which controls some aspect of the expression of an operably linked nucleic acid sequence. Exemplary regulatory elements illustratively include an enhancer, an internal ribosome entry site (IRES), an intron; an origin of replication, a polyadenylation signal (pA), a promoter, a transcription termination sequence, and an upstream regulatory domain, which contribute to the replication, transcription, post-transcriptional processing of a nucleic acid sequence. Those of ordinary skill in the art are capable of selecting and using these and other regulatory elements in an expression construct with no more than routine experimentation.

The term "operably linked" as used herein refers to a nucleic acid in functional relationship with a second nucleic acid. The term "operably linked" encompasses functional connection of two or more nucleic acid molecules, such as an oligonucleotide or polynucleotide to be transcribed and a regulatory element such as a promoter or an enhancer element, which allows transcription of the oligonucleotide or polynucleotide to be transcribed.

The term "promoter" as used herein refers to a DNA sequence operably linked to a nucleic acid sequence to be transcribed such as a nucleic acid sequence encoding a desired molecule. A promoter is generally positioned upstream of a nucleic acid sequence to be transcribed and provides a site for specific binding by RNA polymerase and other transcription factors. In specific embodiments, a promoter is generally positioned upstream of the nucleic acid sequence transcribed to produce the desired molecule, and provides a site for specific binding by RNA polymerase and other transcription factors.

In addition to a promoter, one or more enhancer sequences may be included such as, but not limited to, cytomegalovirus (CMV) early enhancer element and an SV40 enhancer element. Additional included sequences are an intron sequence such as the beta globin intron or a generic intron, a transcription termination sequence, and an mRNA polyadenylation (pA) sequence such as, but not limited to SV40-pA, beta-globin-pA, the human growth hormone (hGH) pA and SCF-pA. The term "polyA" or "p(A)" or "pA" refers to nucleic acid sequences that signal for transcription termination and mRNA polyadenylation. The polyA sequence is characterized by the hexanucleotide motif AAUAAA. Commonly used polyadenylation signals are the SV40 pA, the human growth hormone (hGH) pA, the beta-actin pA, and beta-globin pA. The sequences can range in length from 32 to 450 bp. Multiple pA signals may be used.

Optionally, a reporter gene is included in the transgene construct. The term "reporter gene" as used herein refers to gene that is easily detectable when expressed, for example via chemiluminescence, fluorescence, colorimetric reactions, antibody binding, inducible markers, ligand binding assays, and the like. Exemplary reporter genes include but are not limited to green fluorescent protein (GFP; see Mistili and Spector, Nature Biotechnology 15:961-964 (1997), eGFP, YFP, eYFP, CFP, eCFP, BFP, eBFP, MmGFP, a modified GFP, dsRed (red fluorescent protein, RFP), luciferase and beta-galactosidase (lacZ).

As will be recognized by the skilled artisan, the 5' non-coding region of a gene can be isolated and used in its entirety as a promoter in a transgene to drive expression of an operably linked nucleic acid. Alternatively, a portion of the 5' non-coding region can be isolated and inserted in a transgene to drive expression of an operably linked nucleic acid. In general, about 500-6000 bp of the 5' non-coding region of a developmentally regulated gene is included in a transgene to confer developmentally regulated expression of the operably linked nucleic acid encoding a cytotoxic protein, inhibitory RNA or recombinase for germ cell ablation and ablate germ cells. Optionally, a portion of the 5' non-coding region of a developmentally regulated gene containing a minimal amount of the 5' non-coding region needed to confer developmentally regulated expression of the operably linked nucleic acid encoding a cytotoxic protein, inhibitory RNA or recombinase for germ cell ablation. Assays described herein can be used to determine the ability of a designated portion of the 5' non-coding region of a developmentally regulated gene to confer developmentally regulated expression of the operably linked nucleic acid encoding a cytotoxic protein, inhibitory RNA or recombinase for germ cell ablation.

The term "developmentally regulated promoter" as used herein refers to a promoter that is active during at least a portion of embryonic development, in the case of mouse that is any embryonic day from day 6 to embryonic day 14 (E6, E6.5, E7, E7.5 E8, E8.5, E9, E9.5, E10, E10.5, E11, E11.5, E12, E12.5, E13, E13.5 and E14), also conventionally described as Theiler stages TS8, TS9, TS10, TS11, TS12, TS13, TS14, TS15, TS16, TS17, TS18, TS19, TS20, TS21, and TS22 and active in primordial germ cells and/or during germ cell development and/or germ cell differentiation. The developmentally regulated promoter is active during at least a portion of embryonic day 7.0 to embryonic day 10.5 (E7 to E10.5), also conventionally described as Theiler stages TS10 to TS17 in mouse. For rat the developmentally regulated promoter is active during at least a portion from embryonic day 7 to embryonic day 15.5 (E7, E7.5 E8, E8.5, E9, E9.5, E10, E10.5, E11, E11.5, E12, E12.5, E13, E13.5, E14, E14.5, E15, E15.5 and E16), also conventionally described as Witschi stages 10 to 33. For other species, the developmentally regulated promoter is active in a developmental stage corresponding to those described above for mouse.

Promoters described herein are known to be active in primordial germ cells and/or during germ cell development and/or germ cell differentiation. Additional promoters useful in methods and compositions of the present invention may be determined to be active in primordial germ cells and/or during germ cell development and/or germ cell differentiation using conventional techniques, such as analysis of expression of RNA or protein produced from a nucleic acid construct in which the promoter is operably linked to a nucleic acid encoding the RNA or protein in primordial germ cells and/or during germ cell development and/or germ cell differentiation.

Developmentally regulated promoters are known in the art, as exemplified herein.

Promoters active in the early stages of germ cell development are preferred in order to create a niche in the host embryo to reduce the competition of the donor stein cells with host cells.

Developmentally regulated promoters include, but are not limited to vasa such as mouse vasa (mouse vasa homologue, Mvh, Ddx4, DDX4) promoter as described in Toyooka Y, et al., 2000, Mech Dev. 93(1-2):139-49 and EP1,911,842; human VASA promoter as described in Kee et al. 2009, Nature 462, 222-225 and EP1,911,842; SEQ ID NO:1 and Table 3 for a listing of relevant sequence recognition sites for transcription factor binding including SEQ ID NO:3, SEQ ID NO:4, SEQ ID NO:5, and SEQ ID NO:6; c-kit promoter as described in Yasuda H et al, Biochem Biophys Res Commun 1993; 191:893-901 and see SEQ ID NO 2; Dppa3 (also known as stella or Pgc7) promoter as described in Hirota T et al 2011, Biol Reproduction 85 (2), 367-377; daz1 (also known as dazh or DAZH) promoter as described in Reijo R et al 1996 Genomics 35, 346-352; Linhera K et al 2009, Differentiation 77 (4), 335-349, for example a 1.7 kb promoter fragment upstream of the translational start site of Daz1 promoter is sufficient for tissue-specific expression (Nicholas et al 2009, Genesis 47, 74-84); Dnd1 (Dead end homolog 1) promoter as described in Youngren et al. 2005, Nature 435, 360-364 and Table 4 for a listing of relevant sequence recognition sites for transcription factor binding and SEQ ID NO:7 to SEQ ID NO:15; Fkbp6 (FK506 binding protein 6 or Fkbp36) as described in Meng et al 1998, Genomics 52, 130-137 and Patterson et al 2002, Genomics 79, 881-889 and Table 5 for a listing of relevant sequence recognition sites for transcription factor binding and SEQ ID NO:16 to SEQ ID NO:24; Fragilis (mil-1, Ifitm3, interferon-induced transmembrane protein 3) promoter as described in Tanaka S S et al 2002, Mech Dev 1195, S261-S267; Tanaka S S et al 2004 Dev Dyn, 230:651-659 and Lange et al., 2003, BMC Dev Biol 3: 1; Fragilis-2 (mil-2, Ifitm1, interferon-induced transmembrane protein 1) promoter as described in Tanaka et al 2002, Mech Dev 119S, 5261-S267 and Lange et al 2003, BMC Dev Biol 3:1; GDF-3 promoter as described in Clark A T, Stem Cells, 2004; 22(2): 169-79; Mov1011 (Mov10 like-1, a putative RNA helicase) as described in Wang et al. 2001, Nat Genet. 27, 422-426 and Table 6 for a listing of relevant sequence recognition sites for transcription factor binding and SEQ ID NO:25 to SEQ ID NO:31; Nanog promoter as described in Wu and Yao, 2005, Cell Res, 15(5):317-24; Nanos2 promoter as described in Suzuki et al., 2007, Development 134, 77-83; Nanos3 promoter as described in Suzuki et al 2008, Dev Biol 318, 133-142 and Suzuki et al., 2010, PLoS One, 5(2):e9300; oct3/4 (also known as oct-4 or) promoter as described in Yeom et al 1991, Mech Develop 35 (3), 171-179, Sylvester et al 1994, Nucleic Acids Res 22:901-911 and Nordhoff et al 2001, Mammalian Genome 12 (4), 309-317 and SEQ ID NO:39; Prdm1 (Blimp-1) as described in Turner et al., 1994, Cell 77, 297-306 and Ohinata Y et al 2005, Nature 436:207-213; Prdm14 promoter (a PR domain-containing transcriptional regulator) as described in Yamaji M et al. 2008, Nature Genet. 40, 1016-1022; Tex13 (testis-expressed gene 13) as described in Wang et al. 2001, Nat Genet. 27, 422-426 and GenBank no. AF285576.1 and Table 7 for a listing of relevant sequence recognition sites for transcription factor binding, and SEQ ID NO:32 to SEQ ID NO:34; Tiar (also known as TIAL1) promoter as described in Tominaga et al., 2010, Genes to Cells, 15, Issue 6, 595-606; and TNAP (also known as Alp1, alkaline phosphatase liver, bone, kidney) promoter as described in MacGregor G R et al (1995) Development, 121 (5), 1487-1496 and Lomeli H et al 2000, Genesis 26:116-117. Table 1 lists developmentally regulated promoters, and Table 2 lists a set of more tightly developmentally regulated promoters.

A developmentally regulated promoter included in a transgene and operably linked nucleic acid encoding a cytotoxic protein, inhibitory RNA or recombinase for germ cell ablation can be the 5' non-coding region or a portion of the 5' coding region which confers developmentally regulated expression of an operably linked nucleic acid encoding a cytotoxic protein, inhibitory RNA or recombinase for germ cell ablation of any developmentally regulated gene, including, but not limited to, Vasa, c-kit, Dppa3, daz1, Dnd1, Fkbp6, Fragilis, Fragilis-2, GDF-3, Mov1011, Nanog, Nanos2, Nanos3, oct3/4, Prdm1, Prdm14, Tex13, Tiar and TNAP, as described herein.

Homologues and variants of developmentally regulated promoters may be used according to the present invention.

Promoter homologues and promoter variants can be included in a transgene for germ cell ablation according to the present invention. The terms "promoter homologue" and "promoter variant" refer to a promoter which has substantially similar functional properties to confer the desired type of expression, such as developmentally regulated or ubiquitous expression, on an operably linked nucleic acid compared to those disclosed herein. For example, a promoter homologue or variant has substantially similar functional properties to confer developmentally regulated expression on an operably linked nucleic acid compared to Vasa, c-kit, Dppa3, daz1, Dnd1, Fkbp6, Fragilis, Fragilis-2, GDF-3, Mov1011, Nanog, Nanos2, Nanos3, oct3/4, Prdm1, Prdm14, Tex13, Tiar and/or TNAP promoters.

One of skill in the art will recognize that one or more nucleic acid mutations can be introduced without altering the functional properties of a given promoter. Mutations can be introduced using standard molecular biology techniques, such as site-directed mutagenesis and PCR-mediated mutagenesis, to produce promoter variants. As used herein, the term "promoter variant" refers to either a naturally occurring or a recombinantly prepared variation of a reference promoter, such as Vasa, c-kit, Dppa3, daz1, Dnd1, Fkbp6, Fragilis, Fragilis-2, GDF-3, Mov1011, Nanog, Nanos2, Nanos3, oct3/4, Prdm1, Prdm14, Tex13, Tiar and/or TNAP promoters.

Structurally, homologues and variants of developmentally regulated and/or ubiquitous promoters have at least 80%, 81%, 82%, 83%, 84%, 85%, 86%, 87%, 88%, 89, 90%, 91%, 92%, 93%, 94%, 95%, 96%, 97%, 98%, 99%, or greater, nucleic acid sequence identity to the reference developmentally regulated and/or ubiquitous promoter and include a site for binding of RNA polymerase and, optionally, one or more binding sites for transcription factors.

Homologues and variants of the mouse vasa promoter of SEQ ID NO:1 are characterized by at least 80%, 81%, 82%, 83%, 84%, 85%, 86%, 87%, 88%, 89, 90%, 91%, 92%, 93%, 94%, 95%, 96%, 97%, 98%, 99%, or greater, nucleic acid sequence identity to SEQ ID NO:1. Further homologues and variants of the mouse vasa promoter of SEQ ID NO:1 and include transcription factor binding sites having sequences of SEQ ID NO:3, SEQ ID NO:4, SEQ ID NO:5, and SEQ ID NO:6 and are characterized by at least 80%, 81%, 82%, 83%, 84%, 85%, 86%, 87%, 88%, 89, 90%, 91%, 92%, 93%, 94%, 95%, 96%, 97%, 98%, 99%, or greater, nucleic acid sequence identity to SEQ ID NO:1.

Homologues and variants of the c-kit promoter of SEQ ID NO:2 are characterized by at least 80%, 81%, 82%, 83%, 84%, 85%, 86%, 87%, 88%, 89, 90%, 91%, 92%, 93%, 94%, 95%, 96%, 97%, 98%, 99%, or greater, nucleic acid sequence identity to SEQ ID NO:2.

Homologues and variants of the oct3/4 promoter of SEQ ID NO:39 are characterized by at least 80%, 81%, 82%, 83%, 84%, 85%, 86%, 87%, 88%, 89, 90%, 91%, 92%, 93%, 94%, 95%, 96%, 97%, 98%, 99%, or greater, nucleic acid sequence identity to SEQ ID NO:39.

It is known in the art that promoters from other species are functional, e.g. the human VASA promoter is functional in the mouse. Homologues and homologous promoters from other species can be identified using bioinformatics tools known in the art such as the Mammalian promoter database, and the CSHL Rat Promoter Database (RnPD) (Xuan et al., 2005, Genome Biol 6:R72 and Zhao et al., 2005, Nucl Acid Res 33:D103-107). Bioinformatic tools to identify promoter regions are known in the art, for example PromoSer (Halees et al. 2003, Nucl. Acids. Res. 2003 31: 3554-3559).

These and other developmentally regulated promoters are obtained and used according to well-known methodology. For example, to obtain the promoter for inclusion in a transgene, a Bacterial Artificial Chromosome (BAC) DNA clone for the desired gene can be isolated from a BAC library or obtained for example from the BACPAC Resources Center (BPRC) at the Children's Hospital Oakland Research Institute in Oakland, Calif., USA. Methods for recombineering (recombination-mediated genetic engineering) are known in the art, such as the lambda red recombination technique described in Oginuma M et al. 2008, Mech Dev, 125(5-6): 432-440; Datsenko and Wanner, 2000, PNAS USA, 97(12): 6640-6645 and Zhang Y, et al 2000, Nature Biotechnology 18, 1314-1317. Fragments of full-length promoters can also be used as long as they have the required developmentally regulated activity.

TABLE 1

List of developmentally regulated promoters

| Promoter | Alternative Names |
|---|---|
| vasa | mouse vasa homologue; Mvh, Ddx4, DDX4 |
| c-kit | Kit, CD117, SCFR |
| dazl | Dazh, DAZH |
| Dnd1 | Dead end homolog 1 |
| Dppa3 | Stella, Pgc7 |
| Fkbp6 | FK506 binding protein 6, Fkbp36 |
| Fragilis | mil-1, Ifitm3, interferon-induced transmembrane protein 3 |
| Fragilis-2 | mil-2, Ifitm1, interferon-induced transmembrane protein 1 |
| GDF-3 | Growth differentiation factor 3 |
| Mov10l1 | Mov10 like-1, a putative RNA helicase |
| Nanog | |
| Nanos2 | nanos homolog 2 (*Drosophila*) |
| Nanos3 | nanos homolog 3 (*Drosophila*) |
| oct3/4 | oct-4 |
| Prdm1 | Blimp-1 |
| Prdm14 | PR domain-containing protein 14, PFM11 |
| Tex13 | testis-expressed gene 13 |
| Tiar | TIAL1 |
| TNAP | Alp1, alkaline phosphatase liver, bone, kidney |

TABLE 2

List of more tightly developmentally regulated promoters

| Promoter | Alternative Names |
|---|---|
| vasa | mouse vasa homologue; Mvh, Ddx4, DDX4 |
| Dnd1 | Dead end homolog 1 |
| Fkbp6 | FK506 binding protein 6, Fkbp36 |
| Fragilis | mil-1, Ifitm3, interferon-induced transmembrane protein 3 |
| Fragilis-2 | mil-2, Ifitm1, interferon-induced transmembrane protein 1 |
| GDF-3 | Growth differentiation factor 3 |
| Mov10l1 | Mov10 like-1, a putative RNA helicase |
| Nanos2 | nanos homolog 2 (*Drosophila*) |
| Nanos3 | nanos homolog 3 (*Drosophila*) |
| Prdm1 | Blimp-1 |
| Tex13 | testis-expressed gene 13 |
| Tiar | TIAL1 |

TABLE 3

List of binding sequences for the vasa mouse promoter

| Binding site for Transcription Factor | Binding Position on mouse chromosome | Strand | Binding Sequence | |
|---|---|---|---|---|
| Arnt | chr13: 113450683-113450698 | + | GTTCTCACGTGGCCTG | SEQ ID NO: 3 |

TABLE 3-continued

List of binding sequences for the vasa mouse promoter

| Binding site for Transcription Factor | Binding Position on mouse chromosome | Strand | Binding Sequence | |
|---|---|---|---|---|
| USF-1:USF-2 | chr13: 113450686-113450695 | + | CTCACGTGGC | SEQ ID NO: 4 |
| USF I | chr13: 113442541-113442548 | + | GCACGTGC | |
| Evi-1 | chr13: 113454164-113454179 | − | AGGCAAGGCAACATAA | SEQ ID NO: 5 |
| c-Myc | chr13: 113450681-113450700 | + | TTGTTCTCACGTGGCCTGTG | SEQ ID NO: 6 |

TABLE 4

List of binding sequences for the Dnd1 promoter

| Binding site for Transcription Factor | Binding Position on mouse chromosome | Strand | Binding Sequence | |
|---|---|---|---|---|
| Cdc5 | chr18: 36945231-36945245 | + | GTGTTAACGTCTGAA | SEQ ID NO: 7 |
| GCNF-2 | chr18: 36930976-36930993 | − | TTCCTGGTCAAGGTCAGA | SEQ ID NO: 8 |
| AP-4 | chr18: 36942377-36942386 | − | CACAGCTGGG | SEQ ID NO: 9 |
| MEF-2A | chr18: 36941570-36941585 | − | CTATAAACAGACCTCT | SEQ ID NO: 10 |
| CUTLI | chr18: 36933222-36933236 | + | GTCATAGATAAGCTT | SEQ ID NO: 11 |
| CUTLI | chr18: 36945773-36945787 | + | CACCGAGAAGTATGA | SEQ ID NO: 12 |
| PPAR-alpha | chr18: 36929910-36929929 | + | CAGCACTGCCTCATAGATGA | SEQ ID NO: 13 |
| YY1 | chr18: 36935914-36935933 | + | GGACCGCCATCTGCCGGGGA | SEQ ID NO: 14 |
| YY1 | chr18: 36942745-36942764 | + | GATCTGCCATCCTGCCTGCC | SEQ ID NO: 15 |

TABLE 5

List of binding sequences for the Fkbp6 promoter

| Binding site for Transcription Factor | Binding Position on mouse chromosome | Strand | Binding Sequence | |
|---|---|---|---|---|
| STAT5A | chr5: 135827748-135827756 | − | TTCCCGGCA | |
| STAT5A | chr5: 135839634-135839648 | − | CAATTCCTGGAACTC | SEQ ID NO: 16 |
| STAT5A | chr5: 135839637-135839660 | + | TTCCAGGAATTGCACCACCTGGTG | SEQ ID NO: 17 |
| STAT5A | chr5: 135842246-135842254 | − | TTCCTAGAA | |
| STAT5A | chr5: 135843102-135843125 | − | TTCCCAGTAGTGGCGACCCCAAGA | SEQ ID NO: 18 |
| FOXO4 | chr5: 135834794-135834807 | − | CTGTTGTTCACCAG | SEQ ID NO: 19 |
| HOXA9B | chr5: 135829441-135829454 | − | TGAGAGGGTTTCGG | SEQ ID NO: 20 |
| RORalpha2 | chr5: 135827701-135827713 | − | GGAAGTGGGTCAC | SEQ ID NO: 21 |
| Meis-1a | chr5: 135829441-135829454 | − | TGAGAGGGTTTCGG | SEQ ID NO: 22 |
| E47 | chr5: 135829296-135829311 | − | GAGTCCAGGTGTTGGG | SEQ ID NO: 23 |
| E47 | chr5: 135839647-135839662 | − | TCCACCAGGTGGTGCA | SEQ ID NO: 24 |

TABLE 6

List of binding sequences for the MOV10L1 promoter

| Binding site for Transcription Factor | Binding Position on mouse chromosome | Strand | Binding Sequence | |
|---|---|---|---|---|
| PPAR-gamma-1 | chr15: 88810711-88810727 | + | GACTGGGCAAAAGTTCA | SEQ ID NO: 25 |
| FOXD3 | chr15: 88804989-88805000 | − | TATTGTTTGTTT | SEQ ID NO: 26 |
| E47 | chr15: 88810828-88810843 | + | CAAGGCCTCTGGCGTT | SEQ ID NO: 27 |
| Pbx1a | chr15: 88816001-88816015 | − | GTCGTCAATCATGCC | SEQ ID NO: 28 |

TABLE 6-continued

List of binding sequences for the MOV10L1 promoter

| Binding site for Transcription Factor | Binding Position on mouse chromosome | Strand | Binding Sequence | |
|---|---|---|---|---|
| Nkx5-1 | chr15: 88824333-88824342 | + | CAAGCGTGTG | SEQ ID NO: 29 |
| Arntl | chr15: 88806970-88806985 | - | TGGGGAACGTGTTCCC | SEQ ID NO: 30 |
| Arnt1 | chr15: 88813173-88813188 | - | GTTAGCACGTGAAGGA | SEQ ID NO: 31 |

TABLE 7

List of binding sequences for the Tex13 promoter

| Binding site for Transcription Factor | Binding Position on mouse chromosome | Strand | Binding Sequence | |
|---|---|---|---|---|
| Bach-1 | chrX: 137344530-137344540 | - | GGTGAGTCAGC | SEQ ID NO: 32 |
| NF-E2 | chrX: 137344529-137344539 | + | AGCTGACTCAC | SEQ ID NO: 33 |
| Oct-B1 | chrX: 137346298-137346310 | - | CTCATTTACATAC | SEQ ID NO: 34 |

Host non-human embryos lacking functional endogenous germ cells are provided wherein the germ cells have been ablated by genetic engineering, chemical ablation methods or physical ablation methods. In these non-human host embryos, donor stem cells are able to populate, expand and differentiate towards the germline, germ cells and gametes preferentially, such that the resulting live non-human animals have gametes completely or substantially derived from the donor non-human stem cells.

The term "ablate" and grammatical equivalents encompasses inhibition, inactivation, killing, induction of apoptosis, inhibition of differentiation, inhibition of function and/or inhibition of proliferation of endogenous germ cells, thereby rendering the germ cells incapable of generating gametes.

A host non-human embryo can be an embryo of any of various animals, including non-human mammals, such as non-human primates and rodents. According to embodiments of the present invention, the host non-human embryo is a rodent embryo, particularly a mouse or rat embryo.

Host non-human embryos lacking functional germ cells are provided according to embodiments of the present invention which include a "deleter" transgene encoding a cytotoxic protein.

The term "deleter transgene" or "deleter gene" refers to a transgene encoding a cytotoxic protein configured to express the cytotoxic protein in endogenous germ cells thereby rendering the germ cells incapable of generating gametes or to a transgene encoding an inhibitory RNA configured to express the inhibitory RNA in germ cells thereby rendering the germ cells incapable of generating gametes. The term "deleter transgene" or "deleter gene" further refers to a transgene encoding a protein which can interact with an exogenously added compound rendering it cytotoxic.

The term "cytotoxic protein" refers to a protein which ablates endogenous germ cells, that is, causes inhibition, inactivation, killing, induction of apoptosis, inhibition of differentiation, inhibition of function and/or inhibition of proliferation of endogenous germ cells, thereby rendering the germ cells incapable of generating gametes.

Non-limiting examples of cytotoxic proteins include diphtheria toxin A fragment (DTA, SEQ ID NO:35), attenuated DTA, tox-176, diphtheria toxin receptor, truncated, nonbinding derivative of Pseudomonas exotoxin A (PE-40), Pseudomonas exotoxin PE-38, herpes simplex virus 1 thymidine kinase (HSV-tk), truncated HSV-tk, delta-thymidine kinase (Δ-TK), ricin, Shiga toxin, a gene capable of inducing apoptosis or cell death, such as caspase-7 (Casp7) and caspase-9 (Casp9).

As used herein, the term "cytotoxic protein variant" refers to either a naturally occurring or a recombinantly prepared variation of a reference cytotoxic protein.

Homologues and variants of cytotoxic proteins described herein are characterized by conserved functional properties compared to the corresponding cytotoxic protein.

Thus, for example, homologues and variants of cytotoxic proteins retain the ability to promote cytotoxicity when expressed in a mammalian host cell. Functional characteristics of the putative homologue or variant can be assayed, for example, transient transformation of germ cells in vitro to detect cell death and/or induction of apoptosis. Assays for cytotoxic activity include, but are not limited to, transformation of a host cell with an expression cassette encoding a putative cytotoxic protein homologue or variant, followed by measurement of cell death and/or inhibition of expression of germ cell and or gamete cell markers in the host cell, where increased cell death or decreased expression of germ cell and or gamete cell markers in the host cell, compared to control host cells is indicative of conserved cytotoxic protein functional properties of an homologue or variant. Assays for measurement of cell viability and analysis of expression of germ cell and gamete markers in the host cell are well-known in the art.

The terms "diphtheria toxin A fragment" and "(DTA)" are used interchangeably herein to refer to the catalytic domain (C) of diphtheria toxin. As is well-known, diphtheria toxin is comprised of two polypeptide fragments, A and B (Zdanovskaia, M. V. et al., Research in Microbiology, 2000, 151, 557-562; Bennet, M. J. et al., Protein Science, 1994, 3, 1444-1463). Fragment A (DTA) consists of the catalytic domain (C), whereas fragment B is made up of the receptor domain, (R), and the transmembrane domain, (T). The R domain contains a receptor portion which binds to the BE-EGF receptor on the cell surface (Raab, G. et al., Biochim. Biophys. Acta (BBA)/Reviews on Cancer 1997, 1333, F179-F199). The bound toxin then enters the cytoplasm by endocytosis. The C-terminus hydrophobic series of $\alpha$-sheets, known as the T domain, then embeds itself into the membrane, causing the N-terminus C domain to be cleaved and translocated into the cytoplasm. Once cleaved, the C domain becomes an active enzyme, catalyzing the creation of ADF-ribose-EF-2 from the protein synthesis translocation peptide EF-2 and NAD+ (Hudson T H et al, J Biol. Chem. 1985 Mar. 10; 260(5):2675-80). Cytotoxic activity of diphtheria toxin, including DTA, homologues, fragments and variants thereof is characterized by inhibition of protein synthesis of a cell containing the diphtheria toxin, including DTA, a homologue, a fragment and/or a variant thereof.

Diphtheria toxin A fragment is set forth herein as SEQ ID NO:47 and a nucleic acid sequence encoding Diphtheria toxin A fragment is set forth herein as SEQ ID NO:35.

Methods and compositions are not limited to DTA having the amino acid sequence of SEQ ID NO:47. Variants and fragments of DTA having substantially similar cytotoxic activity may be used.

The term "diphtheria toxin A fragment" encompasses homologue and variant cytotoxic DTA proteins encoded by: 1) a nucleic acid sequence that has at least 60%, 65%, 70%, 72%, 74%, 76%, 78%, 80%, 82%, 84%, 86%, 88%, 90%, 91%, 92%, 93%, 94%, 95%, 96%, 97%, 98%, 99% or greater identity to the nucleic acid sequence set forth in SEQ ID NO:35 or a fragment thereof; 2) the complement of a nucleic sequence that hybridizes under high stringency hybridization conditions to the nucleic acid set forth in SEQ ID NO:35, or a fragment thereof; an amino acid sequence that has at least 60%, 65%, 70%, 72%, 74%, 76%, 78%, 80%, 82%, 84%, 86%, 88%, 90%, 91%, 92%, 93%, 94%, 95%, 96%, 97%, 98%, 99% or greater identity to the amino acid sequence set forth in SEQ ID NO:48 or a cytotoxic fragment thereof.

As will be appreciated by one of skill in the art, due to the degeneracy of the genetic code, more than one nucleic acid will encode an identical protein. Thus, nucleic acids encoding DTA of SEQ ID NO:47 are not limited to SEQ ID NO:35.

A fragment of DTA protein useful in the present invention is any fragment of a DTA protein that is operable in the described methods utilizing DTA.

A Diphtheria toxin A mutant, tox-176, is set forth herein as SEQ ID NO:48.

Methods and compositions are not limited to tox-176 protein having the amino acid sequence of SEQ ID NO:48. Variants and fragments of tox-176 protein having substantially similar cytotoxic activity may be used.

The term "tox-176" encompasses homologue and variant cytotoxic tox-176 proteins having an amino acid sequence that has at least 60%, 65%, 70%, 72%, 74%, 76%, 78%, 80%, 82%, 84%, 86%, 88%, 90%, 91%, 92%, 93%, 94%, 95%, 96%, 97%, 98%, 99% or greater identity to the amino acid sequence set forth in SEQ ID NO:48 or a cytotoxic fragment thereof.

A cytotoxic fragment of tox-176 protein useful in the present invention is any fragment of a tox-176 protein that is operable in the described methods utilizing tox-176.

Herpes simplex virus thymidine kinase is set forth herein as SEQ ID NO:50 and a nucleic acid sequence encoding Herpes simplex virus thymidine kinase is set forth herein as SEQ ID NO:49.

Methods and compositions are not limited to Herpes simplex virus thymidine kinase having the amino acid sequence of SEQ ID NO:50. Variants, homologues, mutants and fragments of Herpes simplex virus thymidine kinase having similar cytotoxic activity may be used. One example for a functional variant which retains thymidine kinase activity and can phosphorylate nucleoside analogs, such as ganciclovir, is Δ-TK (Salomon et al 1995 Mol Cell Bio, 15(10), 5322-5328).

The term "Herpes simplex virus thymidine kinase" encompasses homologue and variant Herpes simplex virus thymidine kinase proteins cytotoxic in combination with a thymidine analog and encoded by: 1) a nucleic acid sequence that has at least 60%, 65%, 70%, 72%, 74%, 76%, 78%, 80%, 82%, 84%, 86%, 88%, 90%, 91%, 92%, 93%, 94%, 95%, 96%, 97%, 98%, 99% or greater identity to the nucleic acid sequence set forth in SEQ ID NO:49 or a fragment thereof; 2) the complement of a nucleic sequence that hybridizes under high stringency hybridization conditions to the nucleic acid set forth in SEQ ID NO:49, or a fragment thereof; an amino acid sequence that has at least 60%, 65%, 70%, 72%, 74%, 76%, 78%, 80%, 82%, 84%, 86%, 88%, 90%, 91%, 92%, 93%, 94%, 95%, 96%, 97%, 98%, 99% or greater identity to the amino acid sequence set forth in SEQ ID NO:50 or a fragment thereof cytotoxic in combination with a thymidine analog.

As will be appreciated by one of skill in the art, due to the degeneracy of the genetic code, more than one nucleic acid will encode an identical protein. Thus, nucleic acids encoding Herpes simplex virus thymidine kinase of SEQ ID NO:50 are not limited to SEQ ID NO:49.

A fragment of Herpes simplex virus thymidine kinase protein useful in the present invention is any fragment of a Herpes simplex virus thymidine kinase protein that is operable in the described methods utilizing Herpes simplex virus thymidine kinase such as a truncated HSV-tk which retains thymidine kinase activity and can phosphorylate nucleoside analogs, such as ganciclovir.

The term "cytotoxic protein" also encompasses proteins which, in combination with an administered agent or compound cause inhibition, inactivation, killing, induction of apoptosis, inhibition of differentiation, inhibition of function and/or inhibition of proliferation of endogenous germ cells, thereby rendering the germ cells incapable of generating gametes. For example, thymidine kinase is a cytotoxic protein in the presence of an administered agent which is a thymidine analog, such as ganciclovir (GCV) or a ganciclovir derivative, such as acyclovir or fialuridine.

The term "cytotoxic protein" encompasses homologues of cytotoxic proteins and variants thereof. The term "cytotoxic protein" further encompasses functionally active cytotoxic protein fragments.

According to embodiments of the present invention, expression of the deleter transgene encoding a cytotoxic protein is developmentally regulated, inducibly regulated or regulated by action of a site-specific recombinase.

In particular embodiments the deleter transgene encoding a cytotoxic protein is configured to express the cytotoxic protein in germ cells of the embryo using a developmentally regulated promoter operably linked to a nucleic acid encoding the cytotoxic protein. The developmentally regulated promoter may confer germ cell-specific expression of the cytotoxic protein or may be active to express the cytotoxic protein in non-germ cells as well as in germ cells.

According to embodiments of the present invention, a transgenic host embryo contains: a transgene encoding HSV-tk, a truncated HSV-tk or Δ-TK operably linked to a developmentally regulated promoter enabling expressing in germ cells. Administration of a thymidine analog, such as ganciclovir (GCV) or a ganciclovir derivative, such as acyclovir or Fialuridine (1-(2-deoxy-2-fluoro-1-D-arabinofuranosyl)-5-iodouracil, FIAU), induces depletion of cells expressing HSV-tk or a truncated HSV-tk or Δ-TK, thereby ablating germ cells. The administration of the thymidine analog can be done orally or by subcutaneous (s.c.), i.p. or intravenously (i.v.) injection and is performed at least one time or repeatedly. An example of a HSV-tk system is described in Zhang, Y. et al. 2005 FEBS T 272, 2207-15; Braun et al. 2000, Nature Medicine 6, 320-326; Borrelli E., et al 1988, PNAS USA, 85 (20), 7572-7576; Chen et al. 2004, Nucl Acids Res 32 (20), e161, Salomon et al 1995 Mol Cell Bio, 15(10), 5322-5328; Cohen et al 1998, Transgenic Res 7, 321-330.

Thus, according to embodiments, the pregnant female is treated with a thymidine analog, such as GCV or FIAU to ablate germ cells expressing HSV-tk, a truncated HSV-tk or Δ-TK in the embryos at any embryo stage from the embryological stages E6 to E13, or a corresponding stage in a non-mouse species. According to embodiments, the pregnant female is treated with a thymidine analog, to ablate germ cells expressing HSV-tk, a truncated HSV-tk or Δ-TK in the embryos at an embryo stage from embryological stage E6.5 to E12.5 or a corresponding stage in a non-mouse species. The thymidine analog will be administered, once, or several times daily over several consecutive days, e.g. on days E6.5, E7.5, E.8.5, E9.5, E10.5, E11.5 and E12.5; or intermittently, e.g. E6.5, E8.5, E10.5 or other intervals. For FIAU an amount from 10 to 50 mg/kg/day will be administered. For GCV any amount from 20-100 mg/kg/day may be administered.

Host non-human embryos lacking endogenous functional germ cells are provided according to embodiments of the present invention which include a deleter transgene encoding a cytotoxic protein, the deleter transgene configured to inducibly express the cytotoxic protein to ablate germ cells in response to administration of an exogenous inducing agent to the embryo, thereby rendering the germ cells incapable of generating gametes.

Inducible promoter systems include, but are not limited to, the tet-off system, tet-on system, the Cre-ERT (Cre recombinase fused to a mutated ligand binding domain of the human estrogen receptor) or Cre-ERT2 (Cre recombinase fused to a G400V/M543A/L544A triple mutation of the human estrogen receptor ligand binding domain also known as Cre recombinase-estrogen receptor T2) system (Metzger and Chambon 2001, Methods 24 (1), 71-80; Yamaguchi et al. 2009, Development 136, 4011-4020; Monvoisin, et al., 2006, Dev Dyn 235, 3413-3422) and the Herpes simplex virus thymidine kinase (HSV-tk) system (Borrelli et al 1988 PNAS USA, 85 (20), 7572-7576; Cohen et al 1998 Transgenic Res 7, 321-330).

According to embodiments of the present invention, a transgenic host embryo contains: a first transgene encoding a cytotoxic protein operably linked to a Tet Operator sequence (TO) and a ubiquitous promoter or a developmentally regulated promoter; and a second transgene encoding a Tet Repressor protein (TetR) operably linked to a second promoter which is a ubiquitous promoter or a developmentally regulated promoter. Administration of a tetracycline or a tetracycline derivative, such as doxycycline, induces expression of the cytotoxic protein, thereby ablating germ cells. The Tet system is well known in the art, and described in for example Wang J. et al. 2007 PNAS 104 (52): 20850-20855; Sheng et al. 2010, BMC Dev Biol, 10:17; Zhang et al., 2007, RNA 13(8), 1375-1383.

According to embodiments of the present invention, a developmentally regulated promoter operably linked to a nucleic acid encoding a cytotoxic protein is further operably linked with an inducible promoter system.

Host embryos lacking functional germ cells according to embodiments, are created by breeding one animal strain each carrying one of two transgenes A and B with the following characteristics. Transgene A expresses a Tet Repressor Protein (TetR) driven by a ubiquitous promoter or a promoter active in germ cells and/or germ cells and/or germ cell derivatives and transgene B a Tet Operator sequence (TO) under the control of a ubiquitous promoter or a promoter active in germ cells and/or germ cell derivatives and operably linked to a nucleic acid encoding a cytotoxic protein and administering tetracycline or a tetracycline derivative, such as doxycycline to induce expression of the cytotoxic protein.

Host mouse embryos lacking functional germ cells according to embodiments, are created by breeding one mouse strain each carrying one of two transgenes A and B with the following characteristics. Transgene A expresses a Tet Repressor Protein (TetR) driven by a ubiquitous promoter or a promoter active in germ cells and/or germ cells and/or germ cell derivatives and transgene B a Tet Operator sequence (TO) under the control of a ubiquitous promoter or a promoter active in germ cells and/or germ cell derivatives and operably linked to a nucleic acid encoding a cytotoxic protein and administering tetracycline or a tetracycline derivative, such as doxycycline to induce expression of the cytotoxic protein.

Advantageously, the administration of the tetracycline or a tetracycline derivative can be performed following transfer of embryos to a pseudopregnant female tetracycline or a tetracycline derivative can be administered in various ways, e.g. via the drinking water, in food pellets, intraperitoneal injection (i.p.) or subcutaneous implantation of slow-release pellets (PNAS USA, Vol. 91, 9302-9306). Typically, donor stem cells are introduced into the embryo prior to administration of the tetracycline or a tetracycline derivative.

Thus, according to embodiments, the pregnant female is treated with tetracycline or a tetracycline derivative to induce expression of the cytotoxic protein or RNA interference molecule in the embryos at any embryo stage from embryological stages E6 to E14, or a corresponding stage in a non-mouse species. According to embodiments, the pregnant female is treated with tetracycline or a tetracycline derivative to induce expression of the cytotoxic protein in the embryos at any embryo stage from embryological stages E6.5 to E10.5 or a corresponding stage in a non-mouse species.

According to embodiments of the present invention, a transgenic non-human host embryo contains: a first transgene (the "deleter transgene") encoding a cytotoxic protein operably linked to a first promoter and containing a cytotoxic protein inhibitory sequence operably linked to recombinase recognition sites called "acceptor sequences;" and a second transgene (the "activator transgene") encoding a site-specific recombinase operably linked to a second promoter.

The "acceptor sequences" included in the deleter transgene allow precise deletion of a nucleic acid positioned between the acceptor sequences by action of the site-specific recombinase. Site-specific recombinases are well-known in the art, exemplified by, but not limited to Cre, a modified Cre, Flp, Dre, Flpe, Flpo and phiC31. The acceptor sequences are recombinase specific and are called loxP or variants thereof for Cre; frt or variants thereof for Flp, Flpe and Flpo; rox or variants thereof for Dre; attP/B or variants thereof for phiC31.

Animals, such as mice or rats, expressing a site-specific recombinase, such as Cre recombinase, from a transgene under control of a developmentally regulated promoter as listed in Table 1 are generated using well-known methodology. Examples of existing mouse strains expressing a site-specific recombinase, such as Cre recombinase, from a transgene under control of a developmentally regulated promoter used in methods and compositions according to embodiments of the present invention are listed in Table 8.

Figure 2:
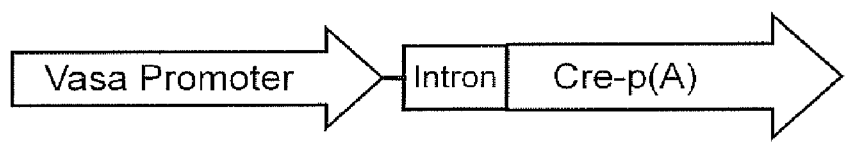
FIG. 2 is a schematic representation of a DNA expression construct containing a site specific recombinase gene to create an activator mouse strain; sequence lengths are not drawn to scale.

In FIG. 1 a schematic representation of a DNA construct containing a site specific recombinase gene to create an activator mouse strain is shown. GC Promoter refers to a tissue-specific or developmentally regulated promoter suitable for developmentally regulated gene expression in germ cells. Intron refers to an intron necessary for expression, e.g. beta globin intron. Cre-p(A) refers to the gene encoding Cre recombinase with a N-terminal nuclear localization signal and 3' p(A) signal. Sequence length are not drawn to scale. FIG. 2 shows a schematic representation of a DNA construct containing a site specific recombinase gene to create an activator mouse strain using the vasa promoter. Vasa Promoter refers to the promoter region of vasa, e.g. a 5.6 kb genomic fragment as described in Gallardo et al 2007, Genesis 45, 413-417 and at least 80% identical to SEQ ID NO:1, suitable for developmentally regulated Rene expression in germ cells. Intron refers to an intron necessary for expression, e.g. beta globin intron. Cre-p(A) refers to the gene encoding Cre recombinase with a N-terminal nuclear localization signal and 3' p(A) signal. Sequence length are not drawn to scale.

TABLE 8

| Cre expressing mouse strains | | |
|---|---|---|
| Mouse Strain Name | Promoter | Reference |
| FVB-Tg(Ddx4-cre)1Dcas/J | Vasa (Ddx4, mvh) | Gallardo, et al., 2007, Genesis 45, 413-417 |
| B6.FVB-Tg(Ddx4-cre)1DCas/J | Vasa (Ddx4, mvh) | Gallardo, et al., 2007, Genesis 45, 413-417. FVB-Tg(Ddx4-cre)1Dcas/J mice were backcrossed to the C57Bl/6J. |
| Nanos3tm2.1(cre)Ysa | Nanos-3 | Suzuki et al. 2007, Development 134, 77-83 |
| Tg(Kit-cre)143Hmb | c-kit | Bergqvist et al., FEBS Lett 438: 76 ± 80. |
| 129-Alpl<tm1(cre)Nagy>/J | Alp1 (TNAP) | Lomeli H et al 2000, Genesis 26: 116-117; The Jackson Laboratory stock no. 008569 |
| Prdm1-Cre | Prdm1 (Blimp1) | Ohinata Y et al 2005, Nature 436: 207-213 |
| Dppa3-MCM | Dppa3 | Hirota T et al 2011, Biol Reproduction 85 (2), 367-377 |

The first promoter, present in the deleter transgene and driving expression of the cytotoxic protein, can be a ubiquitous promoter or a developmentally regulated promoter (such as a germ cell-specific promoter) and the second promoter, present in the activator transgene and driving expression of the site-specific recombinase, is a ubiquitous promoter or a developmentally regulated promoter (such as a germ cell-specific promoter), wherein at least one of the promoters is developmentally regulated.

Figure 3:
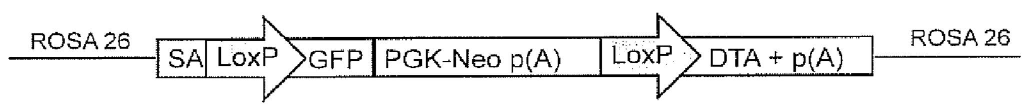
FIG. 3 is a schematic representation of a DNA expression construct used to create a deleter mouse strain; sequence lengths are not drawn to scale.

An example is illustrated in FIG. 3 with a schematic representation of a DNA construct containing a toxic gene to create a deleter mouse strain. Homology arms ("ROSA 26") to the mouse Gt(ROSA)26Sor locus are shown flanking the construct. The construct includes a splice acceptor site (SA), the reporter gene green fluorescent protein (GFP), a neomycin phosphotransferase coding sequence (Neo) with the PGK promoter and transcription termination and mRNA polyadenylation (pA) signal, and both flanked by loxP sites (LoxP), followed by a sequence that encodes for a diphtheria toxin fragment (DTA) followed by a transcription termination and mRNA polyadenylation (pA) signal (also see Ivanova et al 2005, Genesis 43 (3), 129-135). Sequence lengths are not drawn to scale.

The deleter transgene inhibitory sequence is 1) one or more cytotoxic protein-binding sequences which inhibit the activity of the cytotoxic protein and/or 2) one or more stop codons which inhibit the expression of the deleter transgene. A non-limiting example of a cytotoxic protein inhibitory sequence is a loxP reporter gene transcription termination signal loxP (floxed reporter stop).

In one embodiment, transgenic host non-human embryos are created by crossing of two animal strains: 1) a first animal strain carrying an activator transgene ("activator strain") and 2) a second animal strain carrying a deleter transgene ("deleter strain") generating transgenic host non-human embryos where germ cells are ablated and develops a receptive, empty germ cell niche.

In one embodiment, transgenic host non-human embryos are created by crossing of two rat strains: 1) a first rat strain carrying an activator transgene ("activator strain") and 2) a second rat strain carrying a deleter transgene ("deleter strain") generating transgenic host rat embryos where germ cells are ablated and develops a receptive, empty germ cell niche.

In one embodiment, transgenic host non-human embryos are created by crossing of two mouse strains: 1) a mouse strain carrying an activator transgene ("activator mouse strain") and 2) a mouse strain carrying a deleter transgene ("deleter mouse strain") generating transgenic host mouse embryos where germ cells are ablated, developing a receptive, empty germ cell niche.

An activator animal strain contains (a) a site-specific recombinase gene operably linked to a germ cell specific or developmentally regulated promoter causing the expression of a site-specific recombinase gene in germ cells.

According to embodiments of the present invention, the site-specific recombinase is selected from the group consisting of Cre, a modified Cre, Hp, Dre, Flpe, Flpo and phiC31. Optionally, the nucleic acid encoding the site-specific recombinase is operably linked to a nuclear localization sequence and/or intron sequences to enhance expression.

A deleter animal strain contains a deleter transgene encoding a cytotoxic protein, and a cytotoxic protein inhibitory sequence disposed between a pair of acceptor sequences. The cytotoxic protein inhibitory sequence inhibits expression and/or cytotoxic effect of the cytotoxic protein. For example, a cytotoxic inhibitory sequence prevents transcription of the deleter transgene such that the cytotoxic protein is not expressed, such as one or more stop codons which inhibit the expression of the deleter transgene. In a further example, a deleter transgene inhibitory sequence is one or more inhibitory RNA-binding sequences which inhibit the activity of the inhibitory RNA. A non-limiting example of an inhibitory sequence is a loxP reporter gene transcription termination signal loxP (floxed reporter stop).

Removal of the cytotoxic protein inhibitory sequence by the action of the site specific recombinase on the acceptor sites permits expression and/or activity of the cytotoxic protein on the germ cells and their ablation.

Acceptor sequences corresponding to the site specific recombinase are included such as loxP, Frt, rax and attP/B.

Optionally, the deleter animal strain further encodes a reporter gene that allows detection or identification of cells expressing the reporter gene.

According to embodiments of the present invention the site-specific recombinase encoded by the activator transgene of the activator animal strain is Cre and the acceptor sequences included in the deleter transgene of the deleter animal strain are loxP sequences.

According to embodiments of the present invention the site-specific recombinase encoded by the transgene of the activator mouse is Cre, the acceptor sequences included in the transgene of the deleter mouse are loxP sequences the cytotoxic protein encoded by the transgene of the deleter mouse is DTA, the first promoter is a Rosa26 promoter, and a nucleotide sequence containing a DTA inhibitor disposed between the Rosa26 promoter and the DTA gene is operably linked to at least two loxP sites. In the presence of Cre the foxed nucleotide sequence is removed and the Rosa26 promoter then drives the transcription of the DTA gene, ablating the germ cells.

In another embodiment, the deleter animal strain contains two acceptor sequences in an inverted orientation on one chromosome. In one embodiment the acceptor sequences are loxP and the chromosome is mouse chromosome number 2, when Cre is expressed an aberrant recombination event will occur. The resulting genomic rearrangements lead to cell death.

In one embodiment both the loxP sites are in the HoxD complex of mouse chromosome number 2.

In one embodiment host preimplantation embryos are generated by crossing homozygous ROSA26-DTA176 female mice (Wu et al. 2006, Development 133:581-90) with a mouse strain homozygous expressing the Cre recombinase under a developmentally controlled promoter as listed in Table 2. The F1 offspring will have a foxed DTA gene resulting in all F1 embryos eliminating their own germ cells during development and fail to develop sperm.

In a further embodiment host preimplantation embryos are generated by crossing homozygous ROSA26-DTA176 female mice with homozygous B6.FVB-Tg(Ddx4-cre) 1DCas/J (derived from by Gallardo et al Genesis 45(6), 413-7 t C57BL/6J) male mice. After crossing all derived F1 embryos carry both the Cre recombinase under a Vasa promoter control and the foxed DTA gene. This results in all F1 embryos eliminating their own germ cells during development. Preimplantation embryos are isolated and stem cells are introduced by methods known in the art. The resulting chimeras are used in breeding to generate stem-cell derived offspring.

Host non-human embryos lacking endogenous functional germ cells are provided according to embodiments of the present invention which include a "deleter" transgene encoding an inhibitory RNA capable of silencing or disrupting gene expression of one or more genes required for normal development of endogenous germ cells in a non-human animal.

The term "inhibitory RNA" refers to RNA molecules active to specifically decrease levels or function of a target RNA in endogenous germ cells thereby rendering the germ cells incapable of generating gametes. Inhibitory RNA includes antisense RNA, RNAi, shRNA, shRNA and micro RNA (miRNA).

RNA interference is a target sequence-specific method of inhibiting a selected gene. RNA interference has been characterized in numerous organisms and is known to be mediated by a double-stranded RNA, also termed herein a double-stranded RNA compound. Briefly described, RNA interference involves a mechanism triggered by the presence of small interfering RNA, siRNA, resulting in degradation of a target complementary mRNA. siRNA is double-stranded RNA which includes a nucleic acid sequence complementary to a target sequence in the gene to be silenced. The double-stranded RNA may be provided as a long double-stranded RNA compound, in which case it is subject to cleavage by the endogenous endonuclease Dicer in a cell. Cleavage by Dicer results in siRNA duplexes having about 21-23 complementary nucleotides in each of the sense strand and the antisense strand, and optionally 1-2 nucleotide 3' overhangs on each of the two strands.

Alternatively, siRNA is provided as a duplex nucleic acid having a sense strand and an antisense strand, wherein the sense and antisense strands are substantially complementary and each of the sense and antisense strands have about 16-30 nucleotides. The complementary sense and antisense strands and optionally include 1-2 nucleotide 3' overhangs on one or both of the two strands. In one embodiment, a siRNA is preferred which has sense and antisense strands, wherein each of the two strands has 21-23 nucleotides, wherein 2 nucleotides on the 3' end of each strand are overhanging and the remaining 19-21 nucleotides are 100% complementary. As noted above, further details of siRNA compounds are described in Engelke, D. R., RNA Interference (RNAi): Nuts and Bolts of RNAi Technology, DNA Press LLC, Eagleville, Pa., 2003. Additional description of siRNA length and composition is found in Elbashir, S. M. et al., Gene Dev 15:188-200, 2001; and O'Toole, A. S. et al., RNA, 11:512-516, 2005.

siRNA provided as a duplex nucleic acid having a sense strand and an antisense strand may be configured such that the sense strand and antisense strand form a duplex in hybridization conditions but are otherwise unconnected. A double-stranded siRNA compound may be assembled from separate antisense and sense strands. Thus, for example, complementary sense and antisense strands are chemically synthesized and subsequently annealed by hybridization to produce a synthetic double-stranded siRNA compound.

Further, the sense and antisense strands for inclusion in siRNA may be produced from one or more expression cassettes encoding the sense and antisense strands. Where the sense and antisense strands are encoded by a single expression cassette, they may be excised from a produced transcript to produce separated sense and antisense strands and then hybridized to form a duplex siRNA. See, for example, Engelke, D. R., RNA Interference (RNAi): Nuts and Bolts of RNAi Technology, particularly chapters 5 and 6, DNA Press LLC, Eagleville, Pa., 2003 for further details of synthetic and recombinant methods of producing siRNA.

In a further alternative, a double-stranded "short hairpin" RNA compound, termed "shRNA" or "hairpin siRNA" includes an antisense strand and a sense strand connected by a linker. shRNA may be chemically synthesized or formed by transcription of a single-stranded RNA from an expression cassette in a recombinant nucleic acid construct. The shRNA has complementary regions which form a duplex under hybridization conditions, forming a "hairpin" conformation wherein the complementary sense and antisense strands are linked, such as by a nucleotide sequence of about 1-20 nucleotides. In general, each of the complementary sense and antisense strands have about 16-30 nucleotides.

As noted, siRNA and shRNA may be expressed from a DNA template encoding the desired transcript or transcripts. A DNA template encoding the desired transcript or transcripts is inserted in a vector, such as a plasmid or viral vector, and operably linked to a promoter for expression in vitro or in vivo.

As will be recognized by one of skill in the art, particular siRNAs may be of different size and still be effective to inhibit a target gene. Routine assay may be performed to determine effective size and composition of particular compounds. Without wishing to be bound by theory, it is believed that at least the antisense strand is incorporated into an endonuclease complex which cleaves the target mRNA complementary to the antisense strand of the siRNA.

Administration of long RNA duplexes processed to siRNA, as well as administration of siRNA or shRNA, and/or expression constructs encoding siRNA or shRNA, results in degradation of the target mRNA and inhibition of expression of the protein encoded by the target mRNA, thereby inhibiting activity of the encoded protein in the cell.

Further details of RNA interference mechanisms as well as descriptions of target identification, synthetic siRNA and shRNA production, siRNA and shRNA expression construct production, and protocols for purification and delivery of expression constructs and synthetic siRNA and shRNA in vitro and in vivo are described in Engelke, D. R., RNA Interference (RNAi): Nuts and Bolts of RNAi Technology, DNA Press LLC, Eagleville, Pa., 2003.

Inhibitory RNA used in the present invention is capable of silencing or disrupting gene expression of one or more genes required for normal development of germ cells in a non-human animal.

Examples of such genes include, but are not limited to, those listed in Table 9.

TABLE 9

| Gene | Reference for cDNA |
|---|---|
| vasa (Mvh, Ddx4) | Fujiwara et al., 1994, Proc. Natl. Acad. Sci. USA 91, 12258-12262 and GenBank no. G65195 |
| c-kit | Geissler et al., 1988, Cell, 55, 185-192 Qiu et al., 1988, EMBO J. 7(4): 1003-1011. GenBank Y00864.1 |
| dazl (also known as dazh or DAZH) | Reijo et al., 1996, Genomics 35: 346-352 and GenBank no. NM_010021 |
| Dnd1 (dead end homolog 1) | Youngren et al. 2005, Nature 435, 360-364; Bhattacharya C et al. Biochem Biophys Res Commun. 2007, 355(1): 194-9. |
| Dppa3 (also known as stella or Pgc7) stella (PGC7, Dppa3) | Saitou et al., 2002, Nature 418, 293-300 |
| Fkbp6 (FK506 binding protein 6 or Fkbp36)Fkbp6 | Crackower et al., 2003, Science 300, 1291-1295 |
| Mov10l1 (Mov10-like-1) | Wang et al., 2001, Nat Genet 27: 422-426 and GenBank no. AF285587 |
| nanog | Wang et al., 2003, Gene Expr. Patterns 3 (1), 99-103 and GenBank no. AF507043 |
| nanos2 | Tsuda M et al., 2003, Science 301, 1239-1241 |
| nanos3 | Tsuda M et al., 2003, Science 301, 1239-1241 |

TABLE 9-continued

| Gene | Reference for cDNA |
|---|---|
| oct3/4 (also known as oct-4, Pou5f1 or POU domain, class 5, transcription factor 1) | Okazawa et al 1991, EMBO J. 10 (10), 2997-3005; Mizuno and Kosaka 2008, J. Biol. Chem. 283 (45), 30997-31004 and GenBank no. S58422 |
| Prdm1 (Blimp-1) | Turner et al., 1994, Cell 77, 297-306. |
| Prdm14 (PR domain-containing protein 14, also known as PFM11) | Yamaji M et al. 2008, Nature Genetics 40, 1016-1022 |
| sox2 | Collignon et al., 1996, Development 122 (2), 509-520 and GenBank no. X94127 |
| tex13 (Testis expressed gene 13) | Wang et al., 2001, Nat Genet 27: 422-426 and GenBank no. AF285576; |
| Tiar (Tial1) | Beck et al., 1996, Nucleic Acids Res. 24, 3829-3835 |
| TNAP (Alpl, alkaline phophatase liver, bone, kidney) | MacGregor G R et al (1995) Development, 121 (5), 1487-1496. |

Inhibitory RNAs directed to specific genes are commercially available from many suppliers such as OriGene, Life Technologies (Invitrogen), Santa Cruz Biotechnology, Sigma-Aldrich and others. Bioinformatic tools known in the art can be used to design the RNA interference molecule for a specific target gene, such as Gene Link, the RNAi designer from Clontech etc.

Figure 4:
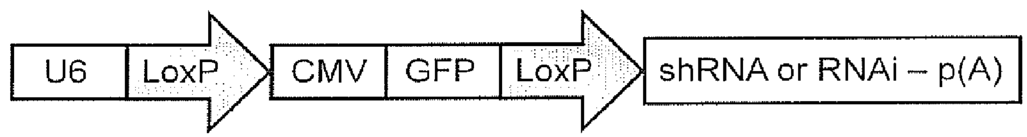
FIG. 4 is a schematic representation of a shRNA or RNAi expression construct; sequence lengths are not drawn to scale.

FIG. 4 shows a schematic representation of a DNA construct containing a U6 promoter (U6) followed by a loxP (LoxP) site, followed by the widely expressed CMV promoter, the reporter gene green fluorescent protein (GFP) and the second loxP site, then followed by the shRNA or RNAi specific for a developmentally regulated gene such as oct3/4 and a transcription termination and mRNA polyadenylation (pA) signal. After the Cre mediated recombination GFP is flipped out and the shRNA expression is driven by the U6 promoter. Sequence lengths are not drawn to scale.

Examples of target RNA for shRNA are vasa, Prdm14 for example as described in Chia et al., 2010, Nature 468, 316-32; Nanos2, Nanos3, oct3/4 (also known as Pou5f1 or POU domain, class 5, transcription factor 1) for example as described in Ivanova N et al., 2006, Nature 442, 533-538, Blimp-1 (also known as Prdm1), as described in Turner et al., 1994, Cell 77, 297-306; stella (also known as PGC7 or Dppa3), c-kit, for example as described in Sikarwar and Reddy, Oligonucleotides 2008, 18(2):145-60, dazl for example as described in Yu et al., 2009, J Mol Cell Biol, 1 (2): 93-103 and Ivanova N et al., 2006, Nature 442, 533-538; Tiar, as described in Izquierdo, 2006 Biochem Biophys Res Commun 348, 2, 703-711, Dnd1; Fkbp6, Mov1011, nanog, for example as described in Yamaguchi et al., Development 136, 4011-4020 (2009) and Ivanova N et al., 2006, Nature 442, 533-538; sox2, for example as described in Ivanova N et al., 2006, Nature 442, 533-538, and tex13.

In particular embodiments the deleter transgene encoding an inhibitory RNA is configured to express the inhibitory RNA in germ cells of the embryo using a developmentally regulated promoter operably linked to a nucleic acid encoding the inhibitory RNA. The developmentally regulated promoter may confer germ cell-specific expression of the inhibitory RNA or may be active to express the inhibitory RNA in non-germ cells as well as in germ cells. A list of such promoters is provided in Table 1.

According to embodiments, developmentally regulated promoters are active in primordial germ cells and/or during germ cell development and/or differentiation. Promoters active in the early stages of germ cell development are preferred in order to create a niche in the host embryo to reduce the competition of the donor stem cells with host cells.

Host non-human embryos lacking endogenous germ cells are provided according to embodiments of the present invention which include a transgene encoding an inhibitory RNA, the transgene configured to inducibly express the inhibitory RNA to ablate endogenous germ cells in response to administration of an exogenous inducing agent to the embryo, thereby rendering the germ cells incapable of generating gametes.

Inducible promoter systems include, but are not limited to, the tet-off system, tet-on system, the Cre-ERT (Cre recombinase fused to a mutated ligand binding domain of the human estrogen receptor) or Cre-ERT2 (Cre recombinase fused to a G400V/M543A/L544A triple mutation of the human estrogen receptor ligand binding domain also known as Cre recombinase-estrogen receptor T2) system.

Figure 5:
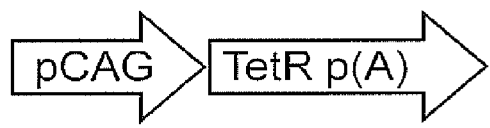
FIG. 5 is a schematic representation of an inducible DNA expression construct; sequence lengths are not drawn to scale.
Figure 6:
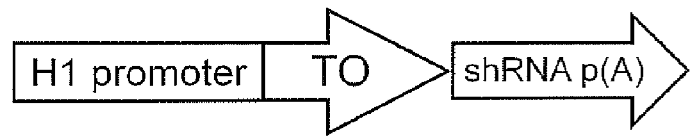
FIG. 6 is a schematic representation of a shRNA or RNAi expression construct; sequence lengths are not drawn to scale.

According to embodiments of the present invention, a transgenic host embryo contains: a first transgene encoding an inhibitory RNA operably linked to a Tet Operator sequence (TO) and a ubiquitous promoter or a developmentally regulated promoter as listed in Table 1; and a second transgene encoding a Tet Repressor protein (TetR) operably linked to a second promoter which is a ubiquitous promoter or a developmentally regulated promoter. Administration of a tetracycline or a tetracycline derivative, such as doxycycline, induces expression of the inhibitory RNA, thereby ablating germ cells. This is illustrated in FIGS. 5 and 6. FIG. 5 is a schematic representation of a DNA construct containing the CAG promoter, which is a combination of the cytomegalovirus (CMV) early enhancer element and modified chicken beta-actin promoter and intron 1 followed by sequences encoding for the TetR protein and a transcription termination and mRNA polyadenylation (pA) signal. Sequence length are not drawn to scale. FIG. 6 is a schematic representation of a DNA construct containing a human RNAse P RNA H1 promoter (H1 promoter), a tet operator (TO) followed by the short hairpin RNA or RNAi sequence and a transcription termination and mRNA polyadenylation (pA) signal. Sequence lengths are not drawn to scale.

According to embodiments of the present invention, a developmentally regulated promoter operably linked to a nucleic acid encoding an inhibitory RNA is further operably linked with an inducible promoter system.

Host mouse embryos lacking functional germ cells according to embodiments, are created by breeding one mouse strain each carrying one of two transgenes A and B with the following characteristics. Transgene A expresses a Tet Repressor Protein (TetR) driven by a ubiquitous promoter or a promoter active in germ cells and/or germ cells and/or germ cell derivatives and transgene B a Tet Operator sequence (TO) under the control of a ubiquitous promoter or a promoter active in germ cells and/or germ cell derivatives and operably linked to a nucleic acid encoding an inhibitory RNA and administering tetracycline or a tetracycline derivative, such as doxycycline to induce expression of the inhibitory RNA.

Advantageously, the administration of the tetracycline or a tetracycline derivative can be performed following transfer of embryos to a pseudopregnant female mouse. Typically, donor stem cells are introduced into the embryo prior to administration of the tetracycline or a tetracycline derivative.

Thus, according to embodiments, the pregnant female is treated with tetracycline or a tetracycline derivative to induce expression of the inhibitory RNA in the embryos at an embryo stage from any of the embryological stages E6, E6.5, E7, E7.5 E8, E8.5, E9, E9.5, E10, E10.5, E11, E11.5, E12, E12.5, E13, E13.5 and E14, or corresponding stages in a non-mouse species. According to embodiments, the pregnant female is treated with tetracycline or a tetracycline derivative inducing expression of the inhibitory RNA in the embryos at an embryo stage from any embryological stage in the range of E6.5 to E10.5, inclusive, or a corresponding stage in a non-mouse species.

According to embodiments of the present invention, a transgenic non-human host embryo contains: a first transgene (the "deleter transgene") encoding an inhibitory RNA operably linked to a first promoter and containing an inhibitory sequence operably linked to recombinase recognition sites called "acceptor sequences;" and a second transgene (the "activator transgene") encoding a site-specific recombinase operably linked to a second promoter.

The "acceptor sequences" included in the deleter transgene allow precise deletion of a nucleic acid positioned between the acceptor sequences by action of the site-specific recombinase. Site-specific recombinases are well-known in the art, exemplified by, but not limited to, Cre, a modified Cre, Flp, Dre, Flpe, Flpo and phiC31. The acceptor sequences are recombinase specific and are called loxP or variants thereof for Cre; frt or variants thereof for Flp, Flpe and Flpo; rox or variants thereof for Dre; attP/B or variants thereof for phiC31. See Table 7 for examples of Cre-expressing mouse strains.

The first promoter, present in the deleter transgene and driving expression of the inhibitory RNA, can be a ubiquitous promoter or a developmentally regulated promoter (such as a germ cell-specific promoter) and the second promoter, present in the activator transgene and driving expression of the site-specific recombinase, is a ubiquitous promoter or a developmentally regulated promoter (such as a germ cell-specific promoter), wherein at least one of the promoters is developmentally regulated. A list of suitable developmentally regulated promoters is provided in Table 1.

The deleter transgene inhibitory sequence is 1) one or more inhibitory RNA-binding sequences which inhibit the activity of the inhibitory RNA and/or 2) one or more stop codons which inhibit the expression of the deleter transgene. A non-limiting example of an inhibitory sequence is a loxP reporter gene transcription termination signal loxP (floxed reporter stop).

In one embodiment, transgenic host non-human embryos are created by crossing of two different animal strains: 1) a first animal strain carrying an activator transgene ("activator strain") and 2) a second animal strain carrying a deleter transgene ("deleter strain") generating transgenic host non-human embryos which develop a receptive, open germ cell niche.

In one embodiment, transgenic host non-human embryos are created by crossing of two different rat strains: 1) a first rat strain carrying an activator transgene ("activator strain") and 2) a second rat strain carrying a deleter transgene ("deleter strain") generating transgenic host rat embryos which develop a receptive, open germ cell niche.

In one embodiment, transgenic host non-human embryos are created by crossing of two different mouse strains: 1) a mouse strain carrying an activator transgene ("activator mouse strain") and 2) a mouse strain carrying a deleter transgene ("deleter mouse strain") generating transgenic host mouse embryos which develop a receptive, open germ cell niche.

An activator animal strain contains (a) a site-specific recombinase gene operably linked to a germ cell specific or developmentally regulated promoter causing the expression of a site-specific recombinase gene in germ cells.

According to embodiments of the present invention, the site-specific recombinase is selected from the group consisting of Cre, a modified Cre, Flp, Dre, Flpe, Flpo and phiC31.

Optionally, the nucleic acid encoding the site-specific recombinase is operably linked to a nuclear localization sequence and/or intron sequences to enhance expression.

A deleter animal strain contains a deleter transgene encoding a cytotoxic protein, and a cytotoxic protein inhibitory sequence disposed between a pair of acceptor sequences. The cytotoxic protein inhibitory sequence inhibits expression and/or cytotoxic effect of the cytotoxic protein. Removal of the cytotoxic protein inhibitory sequence by the action of the site specific recombinase on the acceptor sites permits expression and/or activity of the cytotoxic protein in the germ cells.

Acceptor sequences corresponding to the site specific recombinase are included such as loxP, Frt, rox and attP/B.

Optionally, the deleter animal strain further encodes a reporter gene that allows detection or identification of cells expressing the reporter gene.

According to embodiments of the present invention the site-specific recombinase encoded by the activator transgene of the activator animal strain is Cre and the acceptor sequences included in the deleter transgene of the deleter animal strain are loxP sequences.

According to embodiments of the present invention, a transgenic host embryo contains: a first transgene encoding a oct3/4 RNA interference molecule operably linked to a H1-RNA Polymerase-III (pol III) promoter or the U6 promoter and containing a RNA interference molecule inhibitory sequence flanked on both sides by loxP sites and a second transgene encoding Cre operably linked to a second promoter. In the presence of Cre, the floxed deleter gene inhibitory sequence is removed allowing the H1-RNA Polymerase-H1 or U6 promoter to drive the transcription of the oct3/4 RNA interference molecule, resulting in inhibition of oct3/4 translation and arrested development of germ cells in the transgenic host embryo. A suitable oct3/4 target sequence is: GGATGTGGTTCGAGTATGGT (SEQ ID NO:36).

According to embodiments of the present invention, the reporter gene is operably linked with a ubiquitous promoter (e.g. CMV or CAG or ROSA26) and operably linked to acceptor sequences (e.g. loxP or frt), 5' of the first loxP is a promoter suitable for expression of shRNAs or siRNAs such as the H1-RNA Polymerase-III or U6 promoter and 3' of the second loxP is the shRNA. The reporter gene is ubiquitously expressed in all cells carrying this construct. After the site-specific recombination event, the GFP and its promoter are removed and the shRNA or siRNA is expressed and can inhibit expression of its target gene. In FIG. 4 a schematic representation of a DNA construct is shown. The construct contains a U6 promoter (U6) followed by a loxP (LoxP) site, followed by the widely expressed CMV promoter, the reporter gene green fluorescent protein (GFP) and the second loxP site, then followed by the shRNA or RNAi specific for a developmentally regulated gene such as oct3/4 and a transcription termination and mRNA polyadenylation (pA) signal. After the Cre mediated recombination GFP is flipped out and the shRNA expression will be driven by the U6 promoter. Sequence lengths are not drawn to scale.

In another embodiment, the deleter mouse strain contains two acceptor sequences in an inverted orientation on one chromosome. In a specific embodiment the acceptor sequences are loxP and the chromosome is mouse chromosome number 2. In the presence of Cre recombinase cells containing the inverted loxP will undergo genomic rearrangements resulting in cell death. An example for the inverted loxP mouse strain is described in Kmita et al., 2000, Nat Genet. 26:451-454.

Figures 10, 11:
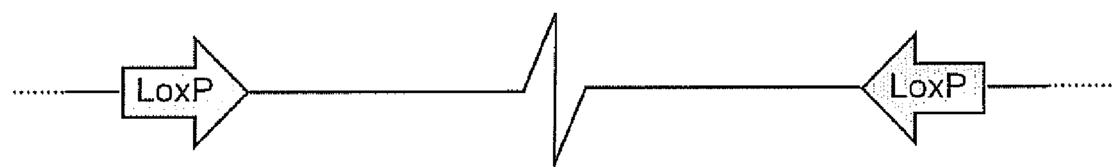
FIG. 10 is an image of a photomicrograph of testes from wild type control and F1 animals from Vasa-Cre× HoxD<tm1Kmta> mice.
FIG. 11 is a schematic representation of a DNA construct used to create a deleter mouse strain by integrating two loxP sites in inverse orientation; sequence lengths are not drawn to scale.

An example of an inverted loxP construct is shown in FIG. 11. FIG. 10 shows that F1 animals derived from breeding mice carrying an inverted loxP with a Vasa-Cre mouse have significantly smaller testes (right) when compared to wild type mice (left). Further these males are infertile and the testes do not contain any sperm.

Ubiquitous promoters include, but are not limited to, CAG (cytomegalovirus early enhancer element and chicken beta-actin promoter and intron 1), CMV (cytomegalovirus), ROSA26, PGK-1 (3-phosphoglycerate kinase), beta-actin, heat shock protein 70 (Hsp70), EF-1 alpha gene encoding elongation factor 1 alpha (EF1α), eukaryotic initiation factor 4A (eIF-4A1), H1-RNA Polymerase-III, and U6 promoter.

The host non-human embryos of the present invention are generated by various methods such as by genetic engineering, chemical modification or physical modification of an embryo.

Expression constructs are provided according to embodiments of the present invention for generation of transgenic host non-human embryos.

Generation of a transgenic non-human animal described herein can be achieved by methods such as DNA injection of an expression construct into a preimplantation embryo or by implantation of stem cells containing the expression construct, such as embryonic stem (ES) cells or induced pluripotent stem (iPS) cells.

The generation of transgenic rats is well-known in the art as exemplified in Mullins et al. 1990, Nature, 344:541-544, Tesson et al. 2005, Transgenic Res 14 (5), 531-546; Charreau et al., Transgenic Res 5 (4), 223-234; and Tenenhaus Dann 2007, Transgenic Res, 16 (5), 571-580. Generation of transgenic cells and organisms including mouse and rats is optionally accomplished using DNA injection, lentivirus injection, zinc finger nuclease or similar technologies (engineered zinc-finger nucleases) as described in Geurts et al, 2009, Science, 325 (5939), 433; Kawamata et al., 2010, PNAS USA 10, 14223-14228; Meyer et al. 2010, PNAS USA 24, 15022-15026 or by TALEN or TAL effector nuclease technology as described in Bogdanove and Voytas, Science 2011, 333, 1843-1846 and Scholze and Boch, Current Opinion in Microbiology 2011, 14:47-53.

According to embodiments of the present invention, expression constructs are provided which include a nucleic acid sequence encoding a deleter gene operably linked to a germ cell-specific or developmental stage-specific promoter.

In one embodiment, transgenic host non-human embryos are created by crossing of two different rodent strains: 1) a rodent strain carrying an activator ("activator rodent strain") and 2) a rodent strain carrying a deleter transgene ("deleter rodent strain") generating transgenic host non-human embryos which develop a receptive germ cell niche.

According to embodiments of the present invention, methods for making a chimeric rodent are provided which include introducing at least one rodent donor stem cell into a rodent host embryo, wherein the host embryo includes (i) a transgene encoding a site-specific recombinase gene operably linked to a developmentally-regulated promoter wherein the site-specific recombinase gene is expressed in germ cells during an embryo stage, and (ii) a transgene encoding a deleter gene whose expression results in ablation of germ cells, wherein expression of the transgene encoding the cytotoxic protein or RNA interference molecule is induced by the enzymatic action of the site-specific recombinase. The transgenic host embryo including at least one donor stem cell is introduced into a pseudopregnant female rodent where it is gestated to produce live-born chimeric rodents wherein germ cells and gametes produced by the chimeric rodent are derived from donor stem cells introduced into the transgenic host embryo.

According to embodiments of the present invention the rodent is a mouse.

According to embodiments of the present invention the rodent is a rat.

Non-human host embryos lacking germ cells can be cryopreserved for storage and later use. For example, non-human host embryos lacking, or destined to lack germ cells can be cryopreserved in a media comprising a cryoprotectant. In a further example, non-human host embryos lacking germ cells can be cryopreserved in a container at subzero temperatures.

Non-human host embryos lacking germ cells of the present invention have utility to generate chimeric animals. One or more stem cells is introduced into the non-human host embryo destined to lack functional germ cells, the embryo with the introduced stem cells is then gestated under suitable conditions, such as by introduction into a pseudopregnant female animal, producing a chimeric animal having all or substantially all germ cells and gametes derived from the stem cells.

The terms "stem cell" and "stem cells" are used interchangeably and refer to pluripotent stem cells capable of differentiating into germ cells, such as embryonic stem (ES) cells, epiblast stem cells (EpiSCs or epi stem cell), embryonic germ (E6) cells and induced pluripotent stem (iPS) cells. The term "stem cell" includes genetically modified stem cells.

Stem cells are cultured in conditions suitable for the particular stem cell line using methods known in the art, for example see Tremml et al., 2008, Current Protocols in Stem Cell Biology, Chapter 1:Unit 1C.4; Baehr M et al. 2003, Philosophical Transactions of the Royal Society B: Biological Sciences 358, 1397-140 and K. Turksen (Ed.) 2002.

A stem cell introduced into a transgenic host embryo can be a stem cell from any of various animals, including mammals, such as humans, non-human primates and rodents. According to embodiments of the present invention, the stem cell is a marmoset stem cell. According to embodiments of the present invention, the stem cell is a rodent stem cell. According to embodiments of the present invention, the stem cell is a mouse stem cell. According to embodiments of the present invention, the stem cell is a rat stem cell.

According to the embodiment of the present invention donor stem cells are from the same species as the host embryo.

According to the embodiment of the present invention donor stem cells are from a different mammalian species than the host embryo.

According to embodiments of the present invention, the stem cell is genetically modified.

According to embodiments of the present invention, the stem cell is a rat stem cell. Germline competent rat ES cells are well-known in the art as exemplified in Buehr et al., 2008, Biol. Reprod. 68: 222-229; Li et al., 2008, Cell 135: 1299-1310; Zhao et al., 2010, J. Genet. Genomics 37, 467-473) and rat iPS cells in 2009 (Li et al., 2009, Cell Stem Cell 4: 16-19; Liao et al., 2009, Cell Stern Cell 4:11-15. To generate chimeric rats, rat ES or iPS cells are injected into preimplantation embryos, such as blastocysts, using well-known methodology such as described in Zhao et al., 2010, J. Genet. Genomics 37, 467-473; Popova et al., 2005, Transgenic Res., 14(5):729-38).

According to embodiments of the present invention, the stem cell is a marmoset monkey (*Callithrix jacchus*) stem cell (e.g. Muller et al 2009, Hum. Reprod 24 (6): 1359-1372).

Methods according to embodiments of the present invention include introducing a donor stem cell into a non-human transgenic host embryo, growing the host embryo under suitable conditions to produce live chimeric animals wherein the gametes of the chimeric animals are substantially or wholly derived from the donor stem cells.

According to embodiments, methods are provided using any combination of the compositions and/or methods described herein to make a chimeric mouse including introducing one, two, three, four, five, six, seven, eight, nine, ten, eleven, twelve, thirteen, fourteen, fifteen or sixteen cells into a mouse host preimplantation embryo that is a 2-cell stage, a 4-cell stage, a 8-cell stage, a 16-cell stage, a 32-cell stage, a 64-cell stage embryo, a morula or a blastocyst; and introducing the preimplantation embryo including the stem cells into a mouse that is capable of gestating the embryo. In one embodiment the host preimplantation embryo is a blastocyst and the number of donor stem cells is six to twelve cells. In one embodiment, the host embryo is an 8-cell stage embryo and the number of donor stem cells is two to ten cells.

Methods of generating chimeric animals having germ cells and/or gametes substantially or wholly derived from donor stem cells are provided wherein the donor stem cells are introduced into a host preimplantation embryo of the present invention.

According to embodiments, stem cells are injected into a 2-cell, 4-cell, 8-cell, 2-cell stage, a 4-cell stage, an 8-cell stage, a 16-cell stage, a 32-cell stage, a 64-cell, a morula and a blastocyst stage host preimplantation embryo of the present invention. The host embryos are selected from a pre-morula stage, a morula stage, an uncompacted morula stage, a compacted morula stage and a blastocyst stage. In one embodiment the host embryos are selected from the embryological age stages E1, E1.5, E2, E2.5, E3 and E3.5 for mouse embryos. According to embodiments, stem cells are injected into a host embryo having a developmental stage selected from a Theiler Stage 2 (TS2), a TS3, a TS4, a TS5 and a TS6, with reference to the Theiler stages as described in Theiler (1989) The House Mouse: Atlas of Mouse Development, by Theiler Springer-Verlag, NY.

In one embodiment the host embryo is selected from the Theiler stages TS3, TS4 and TS5.

In a specific embodiment, the host embryo is a morula.

In a specific embodiment, the host embryo is a blastocyst.

Preimplantation embryos are isolated for introduction of stem cells.

For example, groups of single donor stem cells are selected using a finely drawn-out glass needle (20-25 micrometer inside diameter) and introduced through the embryo's zona pellucida for early embryos and into the blastocysts cavity (blastocoel) using an inverted microscope fitted with micromanipulators for blastocysts. Approximately 9-10 stem cells (ES or iPS or epi stem cells) are injected per blastocysts, or 8-cell stage embryo, 6-9 stem cells per 4-cell stage embryo, and about 6 stem cells per 2-cell stage embryo. Stem cell injection may be assisted with a laser or piezo pulses drilled opening the zona pellucida. (see Kraus et al. 2010, Genesis 48, 394-399). Alternatively, stem cells can be aggregated with morula or injected into early stage embryos (e.g. 2-cell, 4-cell, 8-cell, premorula or morula) with or without the zona pellucida.

Gestating the embryos under conditions suitable for development of the embryos is performed according to standard methodology. The non-human embryos including donor stem cells are implanted into pseudopregnant females as known in the art (see Manipulating the Mouse Embryo: A Laboratory Manual, 3rd edition (A. Nagy et al. 2002, CSHL Press, ISBN- 10: 0879695919; Nagy et al., 1990, Development 110, 815-821; U.S. Pat. No. 7,576,259, U.S. Pat. No. 7,659,442, U.S. Pat. No. 7,294,754, Kraus et al. 2010, Genesis 48, 394-399). Briefly, fertile female rodents between 6-8 weeks of age are mated with vasectomized or sterile rodent males to induce a hormonal state receptive to supporting artificially introduced rodent embryos. Such females are called pseudopregnant At 2.5 dpc (days post coitum) up to 15 of the stem cell containing blastocysts are introduced into the uterine horn. For early stage embryos and morula, such embryos are either cultured in vitro into blastocysts or implanted into 0.5 dpc or 1.5 dpc pseudopregnant females according to the embryo stage into the oviduct.

Chimeric pups developed from the non-human embryos including donor stem cells develop to term after the transfer, birth being dependent upon embryo age at implantation and species. The gametes of the live chimera non-human animals are substantially or wholly derived from the donor stem cells.

The live chimera non-human animals are bred to generate offspring, and all offspring are heterozygous regarding the donor stem cell genome. Alternatively, the gametes of the chimera are collected and used for in vitro fertilization (IVF) or artificial insemination (AI). The gametes isolated from the chimera can also be cryopreserved and stored using methods known in the art. Alternatively, the germ cells of the chimera are collected, matured in vitro or in vivo and used for in vitro fertilization or artificial insemination.

In vitro fertilization (IVF) methodology is well-established. See, for example, Nagy et al. 2002, Manipulating the Mouse Embryo: A Laboratory Manual, 3$^{rd}$ edition, CSHL Press. IVF generally comprises collecting oocytes and sperm from a female and a male respectively, fertilizing oocytes from the female with sperm from the male and maintaining the resulting fertilized oocytes under suitable conditions for development of the fertilized oocytes into embryos. Embryos may be harvested at different stages. The female may be superovulated before oocytes are collected for IVF. Fertilization may be achieved by IVF, intracytoplasmic sperm injection or zona drilling. See, for example, Nagy et al. 2002; Byers et al. 2006, Theriogenology 65, 1716-26; Ostermeier et al. 2008, 3 (7) e2792. IVF can be a useful tool to increase the numbers of embryos obtained from a single female.

Intracytoplasmic sperm injection (ICSI) may be used to improve fertilization rates or to achieve fertilization. The ICSI procedure involves removal of the cumulus cells surrounding oocytes and injection of the sperm or haploid spermatids into the oocytes, ordinarily through a glass pipette (see Kimura and Yanagimachi 1995, Biol Reprod. 53(4):855-62). Spermatids, spermatogonial stem cells and male germ cells can be differentiated in vitro and then used for ICSI (Marh J et al. 2003, Biol Reprod 69(1):169-76; Movahedin M et al. 2004, Andrologia 36(5):269-76; Ogura A et al. 1996. J Assist Reprod Genet. 13(5):4-31-4; Shinohara T et al. 2002 Hum Reprod 17(12):3039-45; Chuma S et al. 2005 Development 132(1):117-22).

As an alternative to collecting mature oocytes for IVF from a female, immature oocytes may be obtained and allowed to mature in vitro, a technique known as "in vitro maturation". As an alternative, follicles, e.g., primary follicle or germ cells, may be isolated from the female and cultured in vitro to obtain oocytes useful for fertilization. In mammals, only a small fraction of immature oocytes develop into mature oocytes; the rest degenerate and die. By isolating immature oocytes from animals and allowing them to mature in vitro, one can obtain many more oocytes suitable for IVF from a given female in a short time frame. Mammalian oocytes are known to undergo maturation in vitro. In the case of mice, cattle and other mammals, in vitro matured oocytes have been fertilized in vitro and given rise to normal healthy offspring when embryos were transferred to an appropriate uterus (Schroeder and Eppig 1984 Dev. Biol. 102:493; Sirard et al. 1988, Biol. Reprod. 39:546). In vitro maturation technique is well known in the art. See, for example, Chiu et al. 2003, Human Reprod. 18: 408-416 and O'Brien et al. 2003, Biol. Reprod. 68: 1682-1686.

Artificial insemination is a process of fertilizing, female animals by manual injection or application of sperm. In such a procedure, male animals are not required at the time of insemination; stored sperm obtained from the animals can be used (see Wolfe 1967 Lab Anim Care 1967, 17(4):426-32 and Sato and Kumura, 2002, J Assist Reprod Genet. 19(11):523-30).

Other methods that can be used to generate live offspring from the chimera including surgical oocyte retrieval, ovary transfer, ovary splitting, ovary fragment transfer, in vitro maturation of oocytes, follicles, spermatogonial stem cells, in vitro differentiation of germ cells, and in vitro differentiation of primordial cells.

Methods for making a chimeric non-human animal or chimeric non-human animal embryo from a non-human animal donor stem cell and a host non-human animal embryo are provided which include introducing a non-human animal donor stem cell into a non-human animal host embryo, wherein the non-human animal host embryo includes (1) a TetR gene operably linked to a ubiquitous promoter or a developmentally-regulated promoter that expresses the TetR gene in germ cells during an embryo stage, and (ii) a Tet Operator (TO) operably linked to a ubiquitous promoter or a developmentally-regulated promoter that expresses the TO gene in germ cells during an embryo stage and operably linked to a nucleic acid encoding a deleter gene. At least one non-human animal donor stem cell is introduced into the non-human animal host embryo, and the non-human animal host embryo including the at least one donor stem cell is introduced into a pseudopregnant female non-human animal to be gestated. During gestation tetracycline or a tetracycline derivative is administered to the female non-human animal to induce expression of the deleter gene in the non-human animal host embryo, resulting in ablation of non-human animal host embryo germ cells. The introduced donor cells differentiate into gametes in the non-human animal host embryo, resulting in live born chimeric non-human animals wherein the germ cells and/or gametes are solely or substantially derived from the donor stem cells.

Methods for making a chimeric mouse or mouse embryo from a mouse donor stem cell and a host mouse embryo are provided which include introducing a mouse donor stem cell into a mouse host embryo, wherein the mouse host embryo includes (i) a TetR gene operably linked to a ubiquitous promoter or a developmentally-regulated promoter that expresses the TetR gene in germ cells during an embryo stage, and (ii) a Tet Operator (TO) operably linked to a ubiquitous promoter or a developmentally-regulated promoter that expresses the TO gene in germ cells during an embryo stage and operably linked to a nucleic acid encoding a deleter gene.

At least one mouse donor stem cell is introduced into the mouse host embryo, and the mouse host embryo including at least one donor stem cell is introduced into a pseudopregnant female mouse to be gestated. During gestation tetracycline or a tetracycline derivative is administered to the female mouse to induce expression of the deleter gene in the mouse host embryo, resulting in ablation of mouse host embryo germ cells. The introduced donor cells differentiate into germ cells and gametes in the mouse host embryo, resulting in live born chimeric mice wherein the germ cells and gametes are solely or substantially derived from the donor stem cells.

Methods for making a chimeric non-human animal or non-human animal embryo from a non-human animal donor stem cell and a host non-human animal embryo are provided which include introducing a non-human animal donor stem cell into a non-human animal host embryo, wherein the non-human animal host embryo includes a nucleic acid encoding thymidine kinase operably linked to a developmentally-regulated promoter that expresses the thymidine kinase in germ cells during an embryo stage. At least one non-human animal donor stem cell is introduced into the non-human animal host embryo, and the non-human animal host embryo including the at least one donor stem cell is introduced into a pseudopregnant female non-human animal to be gestated. During gestation a thymidine analog, such as ganciclovir or a ganciclovir derivative, is administered to the female non-human animal to ablate germ cells expressing HSV-tk or a truncated HSV-tk or Δ-TK in the embryos at an embryo stage from embryological stage E6 to E13, or a corresponding stage in a non-mouse species. According to embodiments, the pregnant female is treated with a thymidine analog to ablate germ cells expressing HSV-tk or a truncated HSV-tk or Δ-TK in the embryos at any embryo stage from embryological stages E6.5 to E12.5 or a corresponding stage in a non-mouse species. The thymidine analog will be administered, once, or several times daily over several consecutive days, e.g. on days E6.5, E7.5, E.8.5, E9.5, E10.5, E11.5 and E12.5; or intermittently, e.g. E6.5, E8.5, E10.5 or other intervals. For FIAU an amount from 10 to 50 mg/kg/day will be administered. For GCV any amount from 20-100 mg/kg/day may be administered.

Methods for making a chimeric mouse or mouse embryo from a mouse donor stem cell and a host mouse embryo are provided which include introducing a mouse donor stem cell into a mouse host embryo, wherein the mouse host embryo includes a nucleic acid encoding thymidine kinase operably linked to a developmentally-regulated promoter that expresses the thymidine kinase in germ cells during an embryo stage. At least one mouse donor stem cell is introduced into the mouse host embryo, and the mouse host embryo including at least one donor stem cell is introduced into a pseudopregnant female mouse to be gestated. During gestation a thymidine analog, such as ganciclovir or a ganciclovir derivative, is administered to the female mouse to ablate germ cells expressing HSV-tk or a truncated HSV-tk or Δ-TK in the embryos at any embryo stage from embryological stages E6 to E13, or a corresponding stage in a non-mouse species. According to embodiments, the pregnant female is treated with a thymidine analog to ablate germ cells expressing HSV-tk or a truncated HSV-tic or Δ-TK in the embryos at an embryo stage from embryological stage E6.5 to E12.5 or a corresponding stage in a non-mouse species. The thymidine analog will be administered, once, or several times daily over several consecutive days, e.g. on days E6.5, E7.5, E.8.5, E9.5, E10.5, E11.5 and E12.5; or intermittently, e.g. E6.5, E8.5, E10.5 or other intervals. For FIAU an amount from 10 to 50 mg/kg/day will be administered. For GCV any amount from 20-100 mg/kg/day may be administered.

Figure 7A:
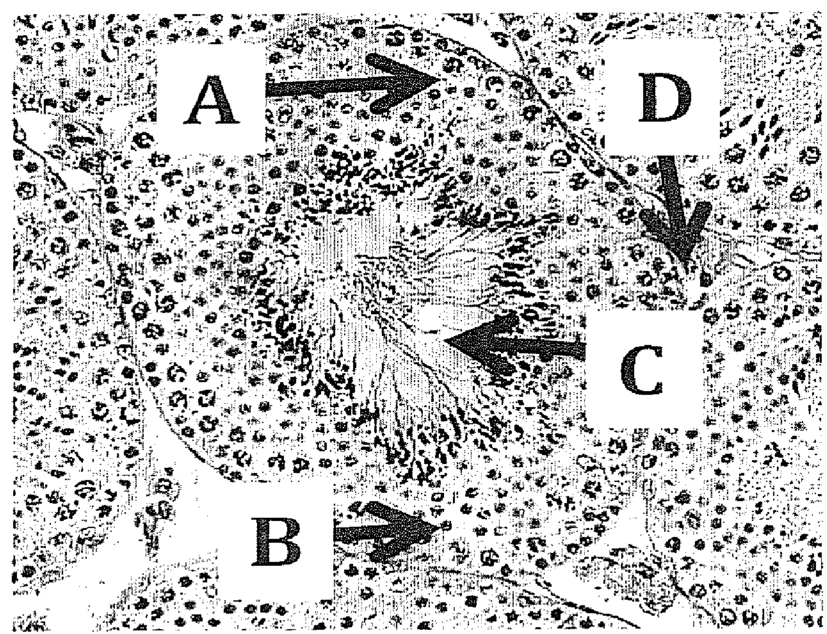
FIGS. 7A and 7B are images of photomicrographs of stained sections of testes derived from normal mice and F1 animals from Vasa-Cre×ROSA26-eGFP-DTA (deleter) crosses.
Figure 7B:
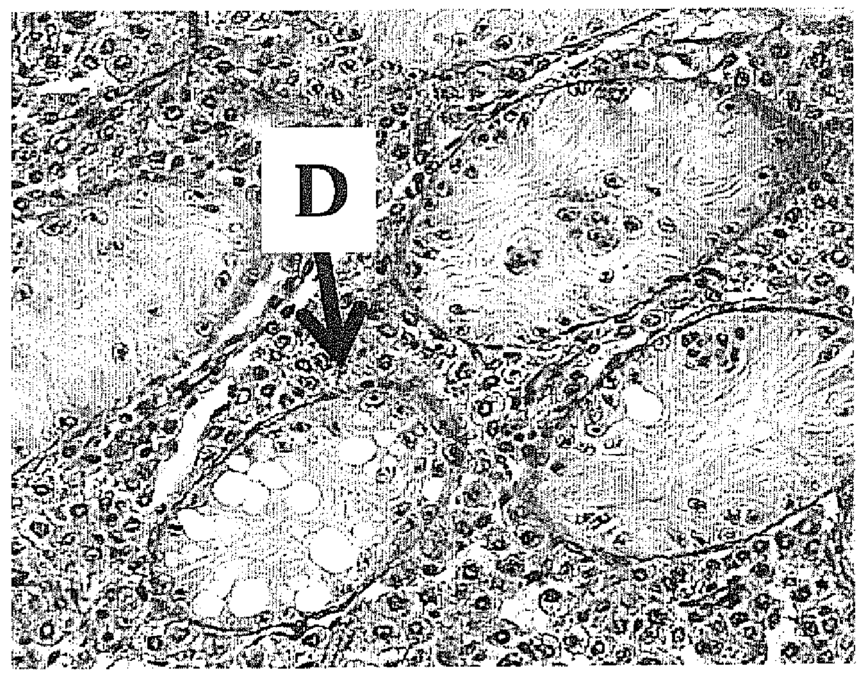

Methods for making a chimeric mouse or mouse embryo from a mouse donor stem cell and a host mouse embryo are provided which include introducing a mouse donor stem cell into a mouse host embryo, wherein the mouse host embryo is an F1 obtained by crossing a Deleter transgenic strain, containing a cytotoxic protein, such diphtheria gene, such as Gt(ROSA)26Sor<tm1(DTA)Jpmb> with the Activator mouse strain containing a site-specific recombinase under the control of a developmentally regulated promoter, such as FVB-Tg(Ddx4-cre)1Dcas. In all cells expressing the site-specific recombinase the cytotoxic protein will be active and ablate such cells. One example for such a promoter is vasa and for the cytotoxic protein the diphtheria toxin fragment a (DTA). When examining the F1 offspring of the intercross of Gt(ROSA)26Sor<tm1(DTA)Jpmb> with FVB-Tg(Ddx4-cre)1Dcas, the resulting adult males are sterile and no sperm is detected in the vas deferentia or the epididymides (see FIG. 7B). In FIG. 7A a testis section of a wild type male mouse is shown with clear presence of spermatogonia (A), spermatocytes and round spermatids (B), elongating, spermatids (C) and Sertoli cells (D). FIG. 7B shows a section of the testes from the F1 intercross of Gt(ROSA)26Sor<tm1(DTA)Jpmb> with FVB-Tg(Ddx4-cre)1Dcas where only Sertoli cells (D) can be identified. To generate embryos, homozygous females of one strain (e.g. FVB-Tg(Ddx4-cre)1Dcas) are superovulated and mated with homozygous males of the other strain (e.g. Gt(ROSA)26Sor<tm1(DTA)Jpmb>). Alternatively, heterozygous mice may be used for one or both of the breeders. Embryos are collected 1.5 days after mating in the morning to isolate 2-cell stage embryos, or 2.5 days after mating in the morning to isolate 4-cell, 8-cell and 16-cell stage embryos, or 3.5 days after mating to isolate blastocysts by flushing the oviducts and uteri horns with embryo culture media, e.g. M2 media. Until injection the embryos are cultured under appropriate conditions. For example early stage embryos can be cultured in vitro to develop into later stage embryos, such as morula and blastocysts. The embryos are injected with stem cells as described above.

Chimera offspring are genotyped in the case when heterozygous parents were used to create the host embryos to select only such mice which contain both DTA and Vasa promoter transgenes. These are used in conventional mating or as gamete donors for IVF. All sperm in males containing both DTA and Vasa promoter transgenes are derived from the introduced stem cells. All oocytes in females from host embryos carrying both, DTA and Vasa promoter transgenes, are derived from the stem cells. For example, R1 male ES cells derived from 129X1/SvJ and 129S1/SV-+p+Tyr-cKit1S1−J/+mice (Nagy et al. 1993, PNAS USA 90, 8424-8428), genetically engineered ES cells 129 S3/Svlmj+Tyr+c+Mfg ES cells (7AC5/EYFP; SCRC-1033 ATCC), ES cells derived from BALB/c and BTBR T+tf/J have been injected into a VASA/DTA host embryo. In all cases, the sperm of male chimera have been derived from the injected ES cells. Further mouse iPS cells (clone 9.48B) were injected, producing chimeric mice.

TABLE 12

Production of Chimeras using Cre-Vasa, DTA host embryos

| Donor Stem Cell | No. of Chimeras | No. of Fertile Chimeras | % Offspring Stem Cell Derived |
|---|---|---|---|
| R1 | 3 | 1 | 100% |
| 7AC5/EYFP | 2 | 1 | 100% |
| BALB/cJ | 3 | 1 | 100% |
| BTBR T+ tf/J | 6 | 4 | 100% |
| iPS 9.48B | 2 | Not tested | Not tested |

Standard analytical tools can be applied to test the identity of sperm or offspring. Methods include but are not limited to sequencing, SNP analysis, PCR technologies as well as protein markers, coat color markers, isozyme analysis (e.g. GPI, glucose phosphate isomerase iszoyme analysis) and detection of any reporter genes or transgenes present in the stem cells using standard methods well established in the art.

The donor stem cell may be a male stem cell (XY) or female stem cell (XX), or an XO stem cell. Male (XY), female (XX) and XO stem cells are introduced into preimplantation host embryos using any of the host systems described above. In the case of male stem cells, the resulting male chimera are advantageously used to produce offspring by breeding with a suitable animal, including by artificial methods. In one embodiment gametes of the male chimera are collected. In another embodiment germ cells or spermatogonial stem cells of the male chimera are collected. In a further embodiment gametes, germ cells or spermatogonial stem cells are cryopreserved. In one embodiment, the female chimera is used to produce offspring by breeding. In another embodiment gametes of the female chimera are isolated. In one embodiment ovaries of the female chimera are isolated. In another embodiment gametes or ovaries are cryopreserved.

In the case of XX and XO stem cells, the oocytes in the resulting female chimera are derived from the donor stem cells and offspring are produced by breeding. In one embodiment gametes are isolated. In another embodiment ovaries are isolated. In a further embodiment gametes and/or ovaries are cryopreserved. In another embodiment male chimera derived with XX or XO stem cells are used for breeding. In one embodiment germ cells are isolated from such male chimera and used for breeding. Germ cells may be matured by in vitro or in vivo techniques. In a further embodiment germ cells are cryopreserved.

Stem cells from one species of non-human mammal can be introduced to a host of a different species of non-human mammal to produce germ cells derived from the stem cells according to embodiments of the present invention. In one embodiment the stem cells are derived from rat, rabbit, marmoset, cattle, goat, sheep, pig, a rare and endangered mammal or an exotic mammal, such as zoological specimens. In one embodiment the stem cells are iPS cells.

An endangered mammal is a population of mammals which is at risk of becoming extinct because it is either few in numbers, or threatened by changing environmental or predation parameters, such as elephants, large cats and non-human primates, including gray wolf, banded hare wallaby, jaguar Asian elephant, saiga antelope and northern white rhinoceros (*Ceratotherium simum cottoni*). Rare or endangered species" include but are not limited to any animal listed by any organization as being threatened or endangered, or any animal whose population, or habitat is threatened, or any animal which is desirably breed in captivity. For example, lists of endangered species may be found at U.S. Fish and Wildlife Service, Endangered Species Program or listed in the Endangered Species Act (ESA).

Stem cells from one species of non-human mammal can be introduced to a rodent host to produce germ cells derived from the stem cells according to embodiments of the present invention. In one embodiment the stem cells are derived from rat, rabbit, marmoset, cattle, goat, sheep, pig, an endangered mammal or an exotic mammal.

In one embodiment rat stem cells are introduced into a mouse host. Optionally, the rat stem cells are genetically modified.

In another embodiment marmoset stem cells are introduced into mouse host. The marmoset stem cells (Müller et al. 2009, Hum. Reprod 24 (6): 1359-1372; Sasaki E et al 2005 Stem Cells 23:1304-1313) are optionally genetically modified.

In one embodiment the stem cells are iPS cells, optionally genetically modified iPS cells.

Chimeric animals are produced in which the germ cells are derived from the stem cells. In a further embodiment the germ cells of the chimera are isolated and matured in vitro or in vivo to generate gametes to produce offspring.

In one embodiment rat stem cells are introduced into a mouse host embryo, chimeras are generated and gametes are isolated from the chimeras and used for IVF or AI to produce offspring.

In another embodiment germ cells are isolated from a chimera and transplanted into a donor rat depleted of its endogenous spermatogonial stem cells to allow the germ cells mature into sperm.

Embodiments of inventive compositions and methods are illustrated in the following examples. These examples are provided for illustrative purposes and are not considered limitations on the scope of inventive compositions and methods.

EXAMPLES

Example 1

Stem Cell Chimera Production

Mouse ES or iPS cells are grown in media optimized for that particular line. Typically ES media contains 15% fetal bovine serum (FBS) or synthetic or semi-synthetic equivalents, 2 mM glutamine, 1 mM Na pyruvate, 0.1 mM non-essential amino acids, 50 U/ml penicillin and streptomycin, 0.1 mM 2-mercaptoethanol and 1000 U/ml LIF (plus, for some cell lines chemical inhibitors of differentiation) in Dulbecco's Modified Eagle Media (DMEM). A detailed description of media is found in Tremml et al., 2008, Current Protocols in Stem Cell Biology, Chapter 1:Unit 1C.4. For review of inhibitors of ES cell differentiation, see Buehr M., et al. 2003, Philosophical Transactions of the Royal Society B: Biological Sciences 358, 1397-1402.

For microinjection, ES or iPS cell are rendered to single cells using a mixture of trypsin and EDTA, followed by resuspension in ES media. Groups of single cells are selected using a finely drawn-out glass needle (20-25 micrometer inside diameter) and introduced through the embryo's zona pellucida and into the blastocysts cavity (blastocoel) using an inverted microscope fitted with micromanipulators. Alternatively to blastocyst injection, stem cells can be injected into early stage embryos (e.g. 2-cell, 4-cell, 8-cell, premorula or morula). Injection may be assisted with a laser or piezo pulses drilled opening of the zona pellucida. Approximately 9-10 ES cells (ES or iPS or epi stem cells) are injected per blastocysts, or 8-cell stage embryo, 6-9 ES cells per 4-cell stage embryo, and about 6 stem cells per 2-cell stage embryo. Following ES cell introduction, embryos are allowed to recover for a few hours at 37° C. in 5% $CO_2$, 5% $O_2$ in nitrogen or cultured overnight before transfer into pseudopregnant recipient females. Alternatively to ES cell injection, ES cells can be aggregated with morula stage embryos. Such methods are well established and can be used to produce stem cell chimeras. For a more detailed description see Manipulating the Mouse Embryo: A Laboratory Manual, $3^{rd}$ edition (A. Nagy et al. 2002, CSHL Press, ISBN-10: 0879695919, Nagy et al., 1990, Development 110, 815-821; U.S. Pat. No. 7,576,259, U.S. Pat. No. 7,659,442, U.S. Pat. No. 7,294,754, Kraus et al. 2010, Genesis 48, 394-399).

Pseudopregnant embryo recipients are prepared using methods known in the art. Briefly, fertile female mice between 6-8 weeks of age are mated with vasectomized or sterile males to induce a hormonal state conductive to supporting surgically introduced embryos. At 2.5 dpc (days post coitum) up to 15 of the ES cell containing blastocysts are surgically introduced into the uterine horn very near to the uterus-oviduct junction. For early stage embryos and morula, such embryos are either cultured in vitro into blastocysts or implanted into 0.5 dpc or 1.5 dpc pseudopregnant females according to the embryo stage into the oviduct. Chimeric pups from the implanted embryos are born 16-20 days after the transfer depending on the embryo age at implantation.

Example 2

In Vitro Fertilization (IVF) Method

IVF methodology is well-established. Briefly, to obtain oocytes suitable female oocyte donor mice are superovulated by injection of PMSG. After 44-48 hr the animals are injected with hCG. Animals are euthanized at 13 hrs post hCG injection. Cumulus enclosed oocytes within the oviduct ampulla are dissected out and collected using a beveled hypodermic needle, and transferred into Fert (K-RVFE-50) COOKS Mouse In Vitro Fert Fertilization medium (MVF).

A suitable sperm donor male (typically 7-12 weeks of age) is euthanized and the cauda epididymis with vas deferens is carefully removed avoiding contaminating the sperm with blood. The sperm is released into 1 ml MVF media by making several cuts through the epididymides and vas deferentia using a beveled hypodermic needle while holding the tissues with a pair of forceps and then allowing the sperm to flow out. Sperm count for a given mouse is variable but a total of $25\times10^6$ is average, of which $1\times10^4$ sperm/ml is adequate of IVF with 15-50 oocytes. For the IVF, sperm and oocytes are mixed in about 250 microliter of MVF medium.

After 4-6 hours incubation at 37° C. in 5% $CO_2$, 5% 0, in nitrogen the fertilized oocytes are collected and washed through two successive 150 microliter media drops to remove cumulus cells and sperm. The fertilized oocytes are cultured overnight at 37° C. in 5% $CO_2$, 5% 0, in nitrogen to develop into 2-cell stage embryos. Embryos may be cultured longer, up to development into the blastocyst stage. Pseudopregnant females at 0.5 dpc are used as the recipient for approximately 15 2-cell stage embryos/female. Pups from the introduced 2-cell stage embryos are expected 18-21 days after the transfer as described for example in Byers et al. 2006, Theriogenology 65, 1716-26 and Ostermeier et al. 2008, 3 (7) e2792.

Example 3

Administration of Tetracycline to Induce (Primordial) Germ Cell Ablation Allowing Preferential Stem Cell Colonization of the Germline Example uses a strain containing transgenes having four elements; i) a tissue specific promoter and enhancer promoter with a proximal enhancer and distal enhancer of mouse oct3/4, described in Ovitt and Schöler 1998 Mol Hum Reprod. 4, 1021-31; ii) rtTA (reverse tetracycline-controlled transactivator gene) a gene expressing protein which binds tetracycline or its analogues (e.g. doxycycline) with poly A signal; and iii) the response element Tet-On (tetO; also called tetracycline-responsive element (TRE) or tet-operator or TO) which upon binding of rtTA complexes tetracycline and drives, iv) the DTA gene leading to cell death. This strain of mouse is normally viable and fertile as the transgene is inactive in the absence of tetracyclines. Such inducible systems are well-established, for example as commercially available from Clontech and as described in Nishijima H et al. 2009 Biosci Trends (5):161-7.

To use this single strain as a host for stem cells providing preferential colonization of the germline heterozygotes or homozygotes embryos are isolated and used as recipients for stem cells. To obtain homozygote embryos the mouse strain is crossed using homozygote males and females. To obtain a mixture of homozygote and heterozygote embryos one parent is homozygous and the other parent is heterozygous. To obtain heterozygote embryos the mouse strain is crossed either with a wild type mouse strain or any other genetically modified mouse strain. The females are superovulated to obtain a maximum number of preimplantation embryos and such embryos are used as stem cell recipient as described in Example 1.

After the introduction of stem cells into the embryos (as outlined in Example 1) these are transferred into pseudopregnant females. The pseudopregnant females are treated with doxycycline from embryonic day E6.5 to E10.5 to induce the expression of DTA transgene in the embryos. Doxycycline is added in the drinking water at 5 mg/ml. Only in cells which are subject to doxycycline and are expressing oct3/4 (i.e. at ≥E6.5 only primordial germ cells) will the DTA gene be activated causing cell death. This allows preferential colonization of stem cells to the germline. After birth chimeric animals are analyzed regarding the stem cell contribution to the germline, which can be done by mating and genetic analysis of the offspring. Alternatively, for males the sperm can be analyzed. Instead of mating, in vitro fertilization as described in Example 2 or other artificial reproductive technologies can be used.

Example 4

Administration of Tetracycline to Induce (Primordial) Germ Cell Developmental Arrest Allowing Preferential Stem Cell Colonization of the Germline In this example a mouse strain mouse is used containing transgenes having three elements: i) TetR (reverse tetracycline-controlled transactivator gene with poly A signal) is constitutively expressed under the control of the CMV/chicken beta-actin (pCAG) promoter; ii) a Tc operator (TO) sequence placed between the H1 promoter and, iii) a shRNA sequence of the target gene. In the absence of tetracycline the transcription of shRNA from the H1 promoter is blocked by the binding of the TetR to the TO sequence. Upon providing tetracycline (doxycycline) the TetR binds with it and is unavailable to bind the TO sequences inhibiting its binding of the TetR. This releases the H1 promoter and the transcription of shRNA occurs causing a reduction of the cognate gene. In this example tetracycline drives short hairpin RNA interference (shRNA) targeted to oct3/4 leading to its suppression in cells expressing oct/3/4 and arrest and/or death, i.e. host germ cells. shRNA which cause knockdown of oct3/4 are described for example in Velkey and O'Shea, 2003, Genesis 37, 18-24; Zafarana et al. 2009, Stem Cells 27, 776-782 and by Clontech and Ambion, Life Technologies in RNA Resources.

Host embryos containing the transgenes TetR and oct3/4-shRNA can be used as a host for stem cells allowing preferential colonization of the germline. Preimplantation embryos are isolated for stem cell injection. After the introduction of stem cells in the preimplantation embryo (as described in Example 1) and their subsequent transfer into pseudopregnant females the transgene present in the host embryos is induced with doxycycline from embryonic day E6.5 to E10.5, e.g. by providing doxycycline in the drinking water 5 mg/ml to recipient females at ≥E6.5 for 4 days. Upon tetracycline induction, all host embryo derived cells will express the shRNA transgene, however only those expressing nominally oct3/4 (i.e. at ≥E6.5 primordial germ cells) will the interfering shRNA cause a cell disruptive event leading to developmental cession and/or cell death. The period of doxycycline induction needs to be at least 4 days to cause total depletion of the host embryos germ cell population, allowing preferential colonization of stem cell derived germ cells. Induction is obtained by providing doxycycline in the drinking water 5 mg/ml to recipient pregnant host females at the times when the implanted embryos are at the ≥E6.5 stage. The treatment is given for 4 days.

After birth, male chimera offspring are selected for either mating, and/or sperm collection. For example, sperm can be cryopreserved before further use. A sperm sample of the chimeric male mice can be genotyped to verify the stem cell contribution. Further, sperm can be used in in vitro fertilization or artificial insemination to create embryos and live offspring.

Example 5

Generation of Mouse Embryo Hosts by Site-Specific Recombination Using Vasa Activator Strain This approach uses two different mouse strains which when crossed produce F1 offspring where endogenous germ cells are ablated early in the development. Where ES or iPS cell have been introduced into the F1 embryos derived from this cross, preferential expansion of ES or iPS cell derived germ cells will occur followed by colonization of the germline.

The Deleter strain is Gt(ROSA)26Sor$^{tm1(DTA)Jpmb}$/J (The Jackson Laboratory, stock 006331, abbreviated JR#006331) and contains a DTA transgene with loxP sites, upon expression of Cre by driven by the Vasa promoter, a site specific recombination event occurs leading to the loss of EGFP expression, the expression of DTA and the death of any cell. The Deleter transgenic strain JR#006331 was crossed with the Activator mouse strain FVB-Tg(Ddx4-cre)1Dcas/J (The Jackson Laboratory, stock 006954, abbreviated JR#006954). The Activator strain JR#006954 contains a transgene construct with the Vasa promoter directing Cre expression in germ cells at least at embryonic stage E10.5. The Vasa promoter is described in Gallardo et al., 2007, Genesis 45, 413-417. Upon crossing homozygous JR#006954 with JR#006331 a recombination event occurs in all offspring in cells where Vasa has been expressed (i.e. germ cells, Tanaka et al. 2000, Gene Dev 14, 841-853) leading to the activation of DTA and the death of the germ cells in which it is expressed. Upon crossing heterozygous JR#006954 (Vasa promoter transgene)×JR#006331 (eGFP-DTA transgene) and examining male F1 offspring examining containing both the eGFP-DTA and Vasa promoter transgenes no sperm are found in the vas deferentia or the epididymides at >8 weeks of age. Frozen sections of the testis were prepared and examined, confirming the absence of any spermatids, sperm or related cell types (see FIG. 7).

Homozygous JR#006954 females are superovulated and mated with JR#006331 males. Embryos are collected 1.5 days after mating in the morning to isolate 2-cell stage embryos, or 2.5 days after mating in the morning to isolate 4-cell and 8-cell stage embryos, or 3.5 days after mating to isolate blastocysts by flushing the oviducts and uteri horns with M2 media (Millipore # MR-015-D or SIGMA #M7167). Until injection the embryos are stored at 37° C., 5% $CO_2$ in KSOM medium (Millipore # MR-023-D). The embryos are injected with stem cells (see Example 1).

Alternatively, homozygous JR#006331 females are superovulated and mated with JR#006954 males. Embryos are collected 1.5 days after mating in the morning to isolate 2-cell stage embryos, or 2.5 days after mating in the morning to isolate 4-cell and 8-cell stage embryos, or 3.5 days after mating to isolate blastocysts by flushing the oviducts and uteri horns with M2 media (Millipore # MR-015-D or SIGMA #M7167). Until injection the embryos are stored at 37° C., 5% $CO_2$ in KSOM medium (Millipore # MR-023-D). The embryos are injected with stem cells (see Example 1).

Alternatively, heterozygous mice may be used for one or both of the breeders. Male offspring are genotyped to select only such mice which contain both eGFP-DTA and Vasa promoter transgenes. These are used in conventional mating or as sperm donors for IVF. All sperm in males containing both eGFP-DTA and Vasa promoter transgenes are derived from the introduced stem cells.

Example 6

Generation of Mouse Embryo Hosts by Site-Specific Recombination Using Vasa Activator Strain Followed by Colonization of the Open Germ Cell Niche by introduced ES Cell F1 blastocysts from (JR#003328×JR#006331) mating were produced by mating heterozygous JR#003328 with heterozygous JR#006331. Thus only 25% of blastocysts are expected to carry the combination Vasa-Cre and DTA. The germ cells are eliminated only in blastocysts with both and DTA alleles.

ES cells were injected in all blastocysts isolated from the JR#003328×JR#006331intercross as described in Example 1. The mice WT, carrying only Vasa-Cre or only DTA were assayed as controls.

Approximately six 129 S3/Svlmj+Tyr+c+Mfg ES cells (7AC5/EYFP; SCRC-1033 ATCC) were injected each into 14 blastocysts (129 53/Svlmj+Tyr+c+Mfg is a genetically modified subclone of R1 ES cells derived from (129X1×129S1)F1 mouse embryos.

Nine pups were born and all offspring were genotyped for both, eGFP-DTA and Vasa promoter transgenes. Two offspring, one male and one female, were positive for both transgenes. Vasa induced expression of Cre would occur in germ cells at or before E10.5 days and onwards, leading to the activation of by recombination the DTA gene and germ cell death. A double transgenic chimeric male was bred with DBA/2J females and 10 litters were produced with a total of 87 offspring. All surviving offspring were genotyped using SNP (single-nucleotide polymorphism) as a genetic fingerprint to determine the genetic origins of the animals (Petkov, P. M. et al. (2004) Genomics, 83 (5), 902-911). An example for the SNP data is shown in Table 10 and SEQ ID NO:37 and SEQ ID NO:38. In the first two rows the sequence for both paternal strains is listed, i.e. the ES cell background129S1/SvImJ and for the females DBA/2J. The third row shows the data obtained from the offspring from mating the chimera with DBA/2J females. All offspring are heterozygous (het) where differences exist between the parental strains. This approach was used to genetically fingerprint 75 offspring from the chimera. All offspring were determined to be paternally derived from the introduced genetically modified ES cell line R1 and maternally from the DBA2J oocytes; i.e. 129 & DBA/2J F1, see Table 11.

TABLE 10

| SNP example. | | | | | | | | | | |
|---|---|---|---|---|---|---|---|---|---|---|
| Mouse Strain | Sequence Data | | | | | | | | | |
| 129S1/SvImJ | TCCCTG | G | A | GAA | T | TGACC | C | G | TATA T | GGCCACGT |
| DBA/2J | TCCCTG | T | G | GAA | C | TGACC | T | T | TATA C | GGCCACGT |
| Offspring | TCCCTG | **het** | **het** | GAA | het | TGACC | **het** | **het** | TATA **het** | GGCCACGT |

TABLE 11

| Genotype of offspring of Vasa-Cre, DTA double transgenic male chimera | | | | |
|---|---|---|---|---|
| # Born | Date of Birth | No. of tail samples collected | Date of sample collection | Confirmed ES cell derived genotype |
| 5 | Mar. 09, 2009 | 5 | Mar. 19, 2009 | 5 |
| 8 | Apr. 01, 2009 | 7 | Apr. 08, 2009 | 7 |
| 6 | Apr. 09, 2009 | 6 | Apr. 23, 2009 | 6 |
| 8 | Apr. 24, 2009 | 8 | May 11, 2009 | 8 |
| 7 | Jul. 01, 2009 | 7 | Jul. 24, 2009 | 7 |
| 10 | Jul. 03, 2009 | 10 | Jul. 24, 2009 | 10 |
| 11 | May 15 2009 | 11 | May 27, 2009 | 11 |
| 7 | Jun. 01, 2009 | 7 | Jul. 01, 2009 | 7 |
| 9 | Jun. 26, 2009 | 6 | Jul. 24, 2009 | 6 |
| 16 | May 07, 2009 | 16 | May 11, 2009 | 16 |

Example 7

Generation of Mouse Embryo Hosts by Site-Specific Recombination Using Vasa Activator Strain Crossed with an Inverted loxP Strain This approach uses two different fertile mouse strains which when intercrossed produce F1 offspring where host germ cells are caused to undergo apoptosis upon Cre expression ~E10.5 or before of embryonic development.

A deleter transgenic strain containing two loxP sites arranged in inverse orientation on chromosome 2; as described in Kmita et al., 2000, Nat Genet. 26:451-454 (The Jackson Laboratory, stock JR#012661, abbreviated JR#012661), is crossed with an activator mouse strain which contains a Vasa promoter region directing tissue specific appropriate expression of Cre in germ cells at E10.5 or before of embryonic development (Tanaka, et al. 2000, Gene Dev 14, 841-853), available from The Jackson Laboratory, stock 006954 (abbreviated JR#006954). In the F1 mice a recombination event occurs in all cells where Vasa has been expressed (i.e. germ cells) leading to a lethal chromosomal recombination and cell death.

Homozygous JR#012661 females are superovulated and mated with JR#006954 males. Embryos are collected 1.5 days after mating in the morning to isolate 2-cell stage embryos, or 2.5 days after mating in the morning to isolate 4-cell and 8-cell stage embryos, or 3.5 days after mating to isolate blastocysts by flushing the oviducts and uteri horns with M2 media (e.g. Millipore # MR-015-D or SIGMA #M7167). Until injection the embryos are stored at 37° C., 5% $CO_2$ in KSOM medium (Millipore # MR-023-D). The embryos are injected with stem cells which are prepared as described in Example 1. For example, blastocysts are injected with a minimum of 5 stem cells, up to 25 stem cells. After injection, the blastocysts are cultured at 37° C. in 5% $CO_2$, 5% $O_2$ in nitrogen until transplantation. About 10 blastocysts per pseudopregnant female are transferred into at 2.5 dpc the same day as the stem cell injections. Pups from the introduced blastocysts are expected about 18 days after the transfer. Male chimeras are bred and/or sperm are tested by PCR to ascertain its stem cell origin.

Example 8

Generation of Rat Embryo Hosts with a Vasa-Cre Activator and Diphtheria Toxin Deleter Strain Two transgenic rat strains are generated. One transgenic rat strain is injected with a Vasa-Cre construct. As promoter, either the rat, mouse or human vasa promoter region are recombineered to the Cre recombinase gene with a functional polyA. The construct is injected into rat zygotes, and the offspring screened for presence and expression of the transgene. Positive rats are tested for transmission of the functional transgene to the next generation and a homozygous rat strain is established. For the second transgene a vector is constructed such that the diphtheria toxin A fragment (DTA) gene is only active after the Cre recombinase has removed loxP flanked sequences. The loxP sites are located between the promoter and the DTA acne and prevent transcription of the DTA gene. The construct is injected into rat zygotes and the offspring is screened for presence of the transgene. Positive rats are tested for transmission of the transgene to the next generation and a homozygous rat strain is established.

To generate rat host embryos the two homozygous strains are intercrossed and preimplantation embryos are isolated. Such embryos are used to introduce rat stem cells and to generate rat chimeras.

Example 9

Figures 8, 9A:
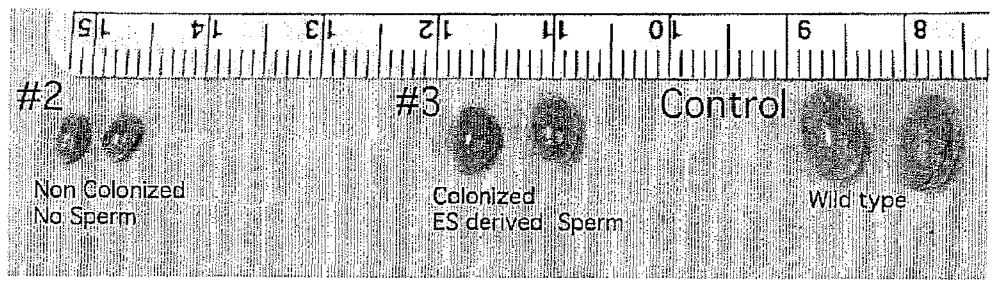
FIG. 8 is an image of a photomicrograph of testes from chimeras.
FIG. 9A is an image of a photomicrograph of stained sections of testes from infertile chimera #2.
Figure 9B:
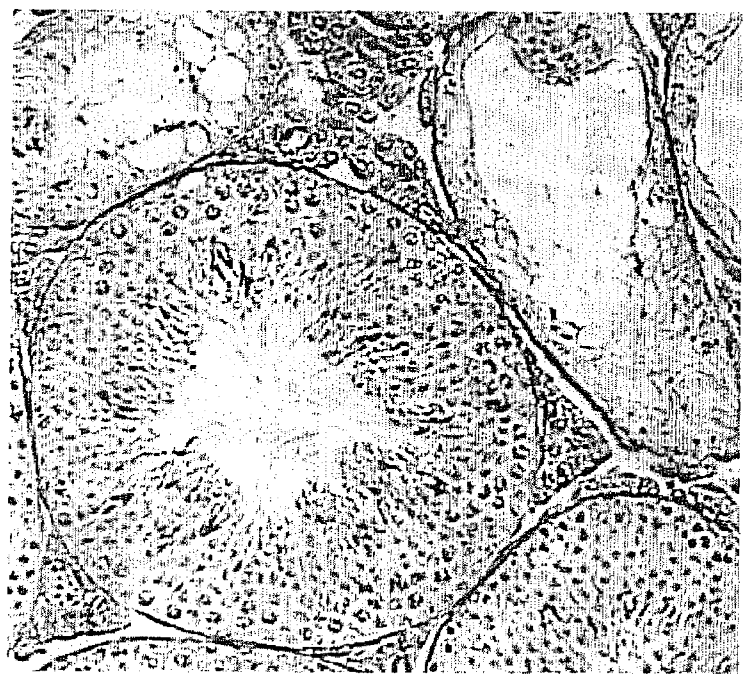
FIG. 9B is an image of a photomicrograph of stained sections of testes from fertile chimera #3.
Figure 9C:
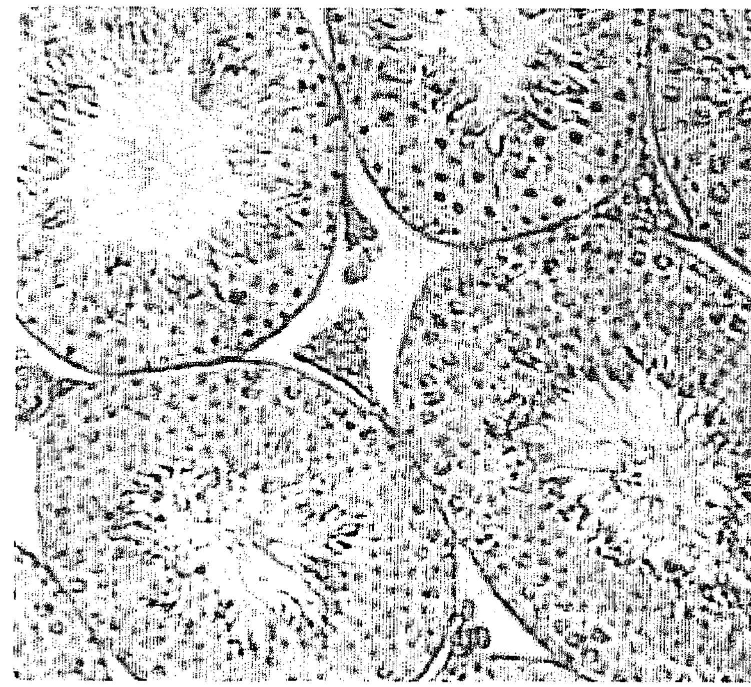
FIG. 9C is an image of a photomicrograph of stained sections of testes from wild type control testis.

Generation of Mouse Embryo Hosts by Site-Specific Recombination Using a Vasa Activator Strain Followed by Colonization of the Open Germ Cell Niche by Introduced R1 ES Cells F1 blastocysts were produced by mating homozygous ROSA26-DTA176 females (The Jackson Laboratory stock no. 010527; Wu et al. 2006, Development 133:581-90) with homozygous B6.FVB-Tg(Ddx4-cre)1DCas/J (The Jackson Laboratory stock no. 012585) male mice. After intercrossing all derived F1 embryos carry both, the Cre recombinase under a Vasa promoter control and the foxed DTA gene. This results in all F1 embryos eliminating their own germ cells early in development. About 20 F1 blastocysts were isolated from the JR#010527×JR#012585 and approximately six R1 stem cells (R1 ES cells, Nagy et al. 1993, PNAS USA 90, 8424-8428) were injected each F1 blastocyst. A total of 17 blastocysts were injected and transferred to pseudopregnant females. Five pups were born, three females and two males. On low level chimeric male #2 and one medium level chimeric male 3 were bred with 129S1/SvImJ (The Jackson Laboratory stock no. 002448) females. Chimera #2, which had very small testes produced no offspring (FIG. 8). After examining testes and epididymis, no sperm were detected as shown in FIG. 9 A-C. Paraffin sections of testes showing seminiferous tubules from infertile chimera #2 (FIG. 9A), compared with sperm productive and fertile chimera #3 (FIG. 9B), compared with control wild type testis (FIG. 9C). All seminiferous tubules from chimera #2 are empty and no sperm development is detectable. In chimera #3 empty and filled seminiferous tubules are detectable, while in wild type controls all seminiferous tubules are filled.

As shown in FIG. 8, chimera #3's testes were smaller than control, however this animal was fertile producing six offspring. Offspring were tested for paternal origin by both coat color (agouti) and SNP (single-nucleotide polymorphism) genotyping. All offspring were shown to be paternally derived from the R1 stem cells. To test more completely the origin of the sperm and to confirm that an IVF approach can be used to directly expand paternally derived offspring from chimeras, an IVF was performed using chimera #3 as a sperm donor.

40 DBA/2J (The Jackson Laboratory stock no. 000671) females were superovulated, yielding 986 oocytes. These were used in an IVF with sperm isolated from chimera #3.

Sperm was examined by Hamilton Thorn NOS computerized semen analyzer (Hamilton Thorn, Beverly, Mass.), an Integrated Visual Optical System for sperm analysis. For chimera #3 (date of birth Feb. 20, 2011) 15.8 million sperm were in the sample, 4.4 million were motile (moving), 0.9 million were progressively motile (travelling and not just moving). These data are consistent with that normally found in mice (see Mouse Phenome Database of The Jackson Laboratory).

The IVF using fresh sperm isolated from chimera #3 yielded 190 two cell embryos (19% of input oocytes), these were transferred into 15 pseudopregnant females. Subsequently 75 pups were weaned. Using SNP analysis (see Example 7 and Table 10) it was determined that all offspring are paternally derived from the introduced ES cell line R1 and maternally from the DBA2J oocytes; i.e. 129 & DBA/2J. F1.

Additionally, the testes of the chimeras #2 and #3 plus a control (JR#10527) animal were collected at 17 weeks of age and grossly compared. FIG. 8 shows an image of a photomicrograph of the testes. A striking size difference is apparent, with the sterile chimera #2 having considerable smaller testis than fertile chimera #3 or wild type control. For comparison a ruler in centimeter scale is included in FIG. 8.

The testis of the chimeras #2 and #3 plus a wild type control mouse were collected into Bouin's fixative, paraffin embedded, sectioned and stained with Periodic acid-Schiff (PAS) for histochemistry (see FIG. 9A-C). A striking difference between the 3 groups is apparent. In the testis of the sterile chimera #2 all seminiferous tubules are empty (FIG. 9A), i.e. no spermatogonial cells or sperm are present. In the testis of the fertile chimera #3 many seminiferous tubules are showing active sperm production, while also empty seminiferous tubules are present; i.e. partial colonization has occurred (FIG. 98). In contrast in the wild type control all seminiferous tubules are filled with developing sperm cells (FIG. 9C).

Example 10

HSV-tk System to Generate Host Embryos

A transgenic rodent strain is constructed to express HSV-tk, a truncated HSV-tk or Δ-TK under a developmentally regulated promoter, such as vasa promoter, c-kit promoter, Dnd1 promoter, Dppa3 promoter, Fkbp6 promoter, Fragilis promoter, Fragilis-2 promoter, GDF-3 promoter, Mov1011 promoter, Nanog promoter, Nanos2 promoter, Nanos3 promoter, oct3/4 promoter, Prdm1 promoter, Prdm14 promoter, Tex13 promoter, Tiar promoter or TNAP promoter (see Table 1), which permits expression of HSV-tk in germ cells, at least at some time during the embryonic stages from E6.5 to E12.5, but not in other essential cell populations within this time frame (expression prior and after this time is not relevant). Under normal conditions expression of the HSV-tk gene has no significant harmful effects. Preimplantation embryos will be isolated from HSV-tk transgenic females and will be microinjected with donor stem cells. To selectively ablate host germ cells in the developing embryo within the female the animals are treated with ganciclovir, FIAU or acyclovir, either orally or by injection (i.p. or i.v.), at a dose of 50 mg/kg/day within the gestation time from E6.5 to E12.5 in the case of mouse. The treatment time is at least for one day and may be continued for up to 7 days. The drug treatment will ablate cells expressing HSV-tk, a truncated HSV-tk or Δ-TK and not affect other cells, including the donor stem cells. The resulting chimera will have all germ cells derived by the donor stem cell.

Example 11

Generation of Mice from Female (XX) ES Cells Using the Vasa Host Embryos

Blastocysts generated as described in Example 9 were injected with approximately 16 female XX genetically modified ES cells, cell line cDK03 (Varlakhanova N V et al 2010, Differentiation, 80, 9-19). 68 injected blastocysts were transferred into pseudopregnant females to make chimeras as described in Example 10. Thirteen putative chimeras were born (7 males and 5 females). At three weeks of age the females will be superovulated and oocytes will be isolated and used in IVF. The resulting offspring will be analyzed for ES cell contribution. Alternatively, female and male chimera will be used in breeding to generate offspring.

Example 12

Generation of Mice from BTBR ES Cells Using the Vasa Host Embryos

Blastocysts generated as described in Example 9 were injected with approximately 16 male PB60.6 BTBR-derived stem cells. The ES cells were isolated from the strain BTBR T+tf/J (The Jackson Laboratory stock no. 002282), which is a model for autism Forty-one microinjected embryos were transferred to pseudopregnant females as described in Example 10. 12 pups were born (6 females and 5 males). These chimeras with varies degrees of chimerism, from high (over 80% by coat color) to low (~10% by coat color) were mated with BTBR mice. To date offspring from 3 chimeras were obtained. Thirty-nine pups have been obtained and all clearly identifiable by coat color that these are ES cell derived. The BTBR mice have a distinct coat color black and tan tufted, with a black back and tan belly. One of these fertile chimeras was a low percentage chimera as assessed by coat color (–10%).

Example 13

Introducing Rat ES Cells into a Mouse Host Embryo

Blastocysts generated as described in Example 9 are injected with approximately six to ten male rat ES cells, line DAc8 (Li et al 2008, Cell, 135 (7) 1299-1310) obtained from MMRRC (University of Missouri). Resulting chimeras will be phenotypically examined at the age from 3-10 weeks. Male chimeras will be sacrificed at the age of 7 weeks or older and testes and epididymis will be isolated and examined for the presence of germ cells and gametes. It is expected that rat germ cells and gametes are capable to develop in the mouse host environment. Female chimeras will be sacrificed at 3 weeks of age or older and ovaries will be isolated and examined for the presence of germ cells and gametes. Male chimeras will be sacrificed at 7-10 weeks of age and examined for sperm and colonization of the testis. Any present germ cells or gametes are expected to be derived from the rat ES cell. Germ cells and gametes can be used for breeding as described above.

Example 14

Introducing BALB/cByJ-PB150.18 ES Cells into the Vasa Host Embryos 21 blastocysts generated as described in Example 9 were injected with approximately six to ten male BALB/cByJ-PB150.18 ES cells. Ten pups were born. Three male chimeras were bred with BALB/cJ (JR#000651) females, but no offspring were produced. After examining the testes and epididymis, sperm were detected in one male. Sperm concentration and motility was comparable to controls. An IVF with BALB/cByJ donor females for oocytes using sperm from the male chimera yielded two cell embryos showing that BALB/cByJ-PB150.18 is capable to colonize the germ layer and produce germ cells and gametes.

Example 15

Detection of the Vasa-Cre Transgene

DNA is isolated, either from the chimera or host embryo, or alternatively a DNA lysates may be used. About 10-300 ng genomic DNA are applied to each PCR reaction. The Vasa-cre specific primers SEQ ED NO:40: CACGTGCAGCCGTTTAAGCCGCGT and SEQ ID NO:41 TTCCCATTCTAAACACCCTGAA and control primers as positive control to monitor that the PCR assay has worked with SEQ ID NO:42: CTAGGCCAAGAATTGAAAGATCT and SEQ ID NO:43 GTAGGTGGAAATTCTAGCATCATCC. The PCR is performed with an annealing temperature of 67° C. and for 35 cycles. The PCR reaction is made with standard PCR buffer, e.g. AB PCR buffer II, $MgCl_2$, dNTP, Taq DNA polymerase, 1 uM of the Vasa-Cre primers and 0.5 uM of the positive control primers and the DNA to be tested. The PCR cycle regime is for example, of one cycle 3 min at 94° C. followed by 35 cycles consisting of 30 s at 94° C., 1 min at 67° C. and 1 min at 72° C., finished by 2 min at 72° C. The resulting product is separated by gel electrophoresis on a 1.5% agarose gel. For Vasa-Cre, a 240 bp band is detectable and for the positive control a 324 bp band. Alternatively quantitative PCR or melt curve analysis or sequencing assays can be performed.

Example 16

Detection of the DTA Transgene

DNA is isolated, either from the chimera or host embryo, or alternatively a DNA lysates may be used. About 10-300 ng genomic DNA are applied to each PCR reaction. Three primers are used, two detecting wild type and one detecting Gt(ROSA)26Sor<tm1(DTA)> transgene. The primers are SEQ ID NO:44 GTTATCAGTAAGGGAGCTGCAGTGG; SEQ ID NO:45 GGCGGATCACAAGCAATAATAACC and for transgene detection SEQ ID NO:46 AAGACCGCGAAGAGTTTGTCCTC. The PCR is performed with an annealing temperature of 64° C. and for 35 cycles. The PCR reaction is prepared with KAPA PCR buffer, dNTP, KAPA Taq DNA polymerase (Kapa Biosystems Inc), 1 uM of each primer and the DNA to be tested. The PCR cycle regime is for example, of one cycle 3 min at 94° C. followed by 35 cycles consisting of 30 s at 94° C., 30 s at 64° C. and 30 s at 72° C., finished by 2 min at 72° C. The resulting product is separated by gel electrophoresis on a 1.5% agarose gel. For the transgene, a 302 bp band is detectable and for wild type a 415 bp band. For a heterozygous sample both bands, the 302 bp and 415 bp bands, are detectable. Alternatively quantitative PCR or melt curve analysis or sequencing assays can be performed.

Example 17

Development of Germ Cells or Gametes from Endangered Species

The example provided is pertinent to endangered mammals, including, but not limited to, gray wolf, banded hare wallaby, jaguar, Asian elephant, saiga antelope and white rhinoceros.

The basic approach requires the creation of Induced Pluripotent Stem cells (iPS) which are a type of pluripotent stem cell artificially derived from a non-pluripotent cell, typically an adult somatic cells, e.g. skin cells, by inducing “forced” expression of specific genes. The adult somatic cells here being derived from the endangered mammal and the iPS cells being made using techniques well known in the art.

iPS cells are very similar to embryonic stem (ES) cells and have the capacity to form viable chimeras, including the capability for germ cell and gamete development. Here, iPS cells would be derived from both male and female endangered mammals. Female derived iPS would be expected to colonize efficiently the female germline, whilst male animal derived iPS cells would efficiently colonize the male germline. The host embryo may also carry additional genes appropriate for the endangered mammal which improve the efficiently of germ cell and gamete development.

To achieve the development of germ cells and gametes from a endangered mammal, iPS cells will be introduced into the morula and blastocyst stage of F1 blastocysts produced by mating homozygous (JR#010527) females with homozygous (JR#012585) male mice, or other host embryos as described above. In one combination all F1 embryos carry both, the Cre recombinase operably linked to a Vasa promoter and the foxed DTA gene.

Approximately six to sixteen male iPS derived cells will be injected into F1 blastocysts isolated from the JR#010527×JR#012585 intercross. Injected blastocysts will be transferred into pseudopregnant females to make chimeras as described in Example 1.

At term, putative chimeras will be born. At ~7 weeks of age animals can be examined. Any germ cells or gametes in either the resulting male or female chimeras will be derived from the iPS cell and hence the endangered mammal. Upon maturation these germ cells or gametes will be used in IVF or ISCI, and the resulting embryos will be placed into a suitable host; i.e. one capable of carrying the resulting embryo to term.

Example 18

Introducing Mouse iPS Cells into the Vasa Host Embryos

Forty-eight blastocysts generated as described in Example 9 were injected with approximately six to sixteen genetically modified mouse iPS cells (Varlakhanova et al 2010, Differentiation, 80 (1), 949). Twenty-two pups were born. To date two chimeras were detected and experiments are ongoing to analyze germ cell contribution and fertility.

Sequences

SEQ ID NO: 1 Vasa Promoter - Mus musculus

TGTGCCACCATGCCTGGCCCAGTTTCTTGCTTTGTATTATAAACTTTATAGCTGGTAAGACTCTG

GACCCACACGTGTTTGATTTGTCTCTTCTCTCCTGAGACATTTTTTCCCAGTAACATTTCCTGAA

TTTTGTATTTTATTGTCTCTGCATCTGTGCTGAGACATAACATCTTCTGTTTCTTCTATTTGCCA

TGAACTGGGAGTTAAGTCTAAGAATTTGATTAAAGCTGAAGTTGAGTTTGAAATCAAACCTCTAC

ATGTAGCGTTTTGTATTTCCCACTGTGATACATCAACCAGCACATGGTTCTTGGAGGTCTTTGCT

TTGTGGTATAAAGTTGGCCCAGTGTGTTTAAATGTTGTCCTCTTTAAGGAGGTAGCTAGGTAAGA

TCACACGCCGGTTACCTACCTCCCTACTGATGCACTAACTGGTGTGTCTAGCCTAGCCTAAGGCC

CTAGGGTACCATGCATCCCATAATAGCTTATGTGAGGCCCAACACATTTGTAGATAACAGCATCA

GGTCATAGTGTCATAAGGTTGGACACCCCTGGCAGAGTTTCCTGTACCACACTATCTTCAAAAGA

GCTAAAGAAGTAAGGTGGAAAAAAACAAACATCATAGTGTTCTGATTTTACTGTAACAGGAAAAG

ACTCACTGAAAAGATGCCAAGGCCCAGATTTCCCCTCCCACAATTCCAAGCTTCATGGAGAATGA

TACCTCCACTTTGGGGATGGAGAAGGAATTAAATCCTGACCACAGACTTGAAGCAGTAAGAACTT

ATCACCGTGATGTCAGTTCTGGGTGGAACCCTATGCATCCCGTGGCCCTGTACCTGCAGATGCTG

CTGCTGGACCTGTGATAGATGGCCAGTACTACAGTTAGGAATCTTTCTGACAACTGCAGCTTTTA

GAATGGAAATCAAAACTCCACCTACTGGATGGCACAACATGAAAGCAAGGACTGTGCCTTGCAGC

TCAGGGCCAGCCTTAGTACTAGTCTCTGAGGGACCGTTGCTACCACCGGTTCCCAACCTGTAGCA

GCACAACTATCCTGGACCAGGGTTCACGGATGGAGCTCAAGACCTTGACATCTGTCACAGTTATG

CTCTGCACCATGAGGAAGTTGTCTCAGTTTGCCTTACTGCCACAGCACCGGCTGTGGGCTCAGCA

TTGTGACACTCAGAGCCACAGTTCTGGAGCAGGAACCAGGGCAGGTCCCTCTGGTGATTCTTTCT

ACAGTTCACGACCAGAGGCTGTTGGCTTTGGAAGGCACCTGGAGGTCTGTGCAAGCCCCGGACAG

AGGCTTGTGTAGATGAAGGACCCTTTATAAAAAGCTCCCTAATTGAGTCTTGAAAAACTCACCOG

CTGAGGATTTAGGAGAAACCTAAGCTTGGATCGCCTCCTAACACTGCCACAGGTAACCTGAATTT

TGGTGCCATATAGTGTTAGAAACTATAGGCTGAGAGAGAGAGAGAAAAAAAAAACATTCTTTTTT

CAATTTCTGAAAACAAACAAAACCAAAACAAGCCATATTATGAAGACCGGAATAAATACCTAATC

CTTTGTCCTCGAATGACATCACACATCAATAAGAACCAAGGATGTTTAAGGAACTATGACCTCAT

CTGACAGTATAAATATAAAATGCCAGAAACCGTCAAGATAGTAACCAGTGTGGGTGGATGCTCAT

ATGTGTACTGTATTAGTTACTTTTTCATTGTTGTGATAAAATACCACGACTAAAGCCTGACTTAT

AGGAGAAGGAATTTGTCCTGGCTTGTGTTTTCAGAGTGATATGACTCCATCATGACAGGGACGCA

TGGAAGCCAGCAACAGGTATGATGCTGGGGCAGCAAGCTGAGAGCTCACATCCGCCACTGAAGGC

ACAAAACAGCAAGTGTGAGCTGGAAGTGGTGTGAGGCTATATACTAGCAAAGGCTGCCCTACTGA

TACGCTGTCTCCAGGAGGACTGCATTCCCCAAGCTTCTCTGATCATCACAACCAACTGAGAACTA

AATGGTCAAATACCTGGGTCAGTGGGGATCATTTCTCATTCAAACTTCCACAGATAATTAAAAGC

AAATAAATGAACCAGGTTTAAGGAAACTTACTGAATTCCAATAGAAAATATAGAAATAAATCAAT

ACTTTAGTAGATATAATTGACTGAGACATGGGGGCAAATTTTAAAAAGTTGAAATTCTTGATAAT

GAAGGTATACTAAACAAAATAAAATTGCATTAGGGAAGCATTGATGTTAGAGTAAATCAAGCAGA

AGAGAGAATGAGTGAATTCCAACATAGGCCATTTGAAAATGCACAGAAGAGAAAAAGAATTAAGA

GGAAGAAATGTACTCATGGTAACCTTGGAGCAACAGTGAAAGGGTAAGTAGGTTAGTGGGGATAT

GGACGGGACTTGAGAACACCAAAAGAGTTAATCGATGCAACTACGTTATGATCAAACACAGTCAG

GTTCCAGGTTCTGCAGTAAACTGAATCTCCAGTTTTCACGTTATGTAGATCCATCTCCATGAATC

-continued

TGGCCTGGCCTTGTGAATTTCTGGTAACTGATTAGTTGAAAGTTGCAAATATAATTGTTTAACTT

CTTATGCTAGAATTCAAGAAGCCTTGCAACTATTACCCTGGTCCTTTGGAGCGATGTCCCTGACA

AGTGTGTCCAGTTGAAATGCAGCATCCTTACAGAGTCTGACTGAGATTGTCCAACAACCTTCAGA

GCCTAAGTCAGCCTCTTGGAAACTATTCAATTGTTCTGGCCATCCCAGCCACTAGATGCCAGAGT

AGAGAAGTCACCTTGGATGTTAAACAAACTGGTATTGGAGGTTGGGGATAAACTCAGTAGTACAG

AGCTTGCCTGGCACGCTCAAGTACCTAGGTTCAAACTCTGGCAATGCCAAAAAAGAAAAAAGTTG

ATAGCAAACTCTCAGATGATTCAAGTTCTAATTAGCATTTGAATGGAATTGTATGAGATGGTCTC

CTGAGCCCTCTCAATCCCTGAGAGAGAATTTTTTTGTAAGTCAATATATTATGCAATAGTTTGT

TATATAGTTGTACTGGCTAATTTGGGTCAAGCTGGAGTTATCACAGAGAAAGGAGCTTCAGTTGG

GGAAATGCCTCCATGAGATCCAACTGTAAGGCATTTTCTCAATTAGTGATCAAGGGGGAAAGGCC

CCTTGTGGGTAGGACCATCTCTGGGCTGGTAGTCTTGGTTCTATAAGAGAGCAGGCTGAGCAAGC

CAGTAAGGAACATCCCTCCATGGCCTCTGCATCAGCTCCTGCTCCTGACCTGCTTGAGTTCCAGT

CCTGACTTCCTTTGGTGATGAACAGCAATGTGGAAAGTGTAAGCTGAATAAACCCTTTCCTCCCC

AATTTGCTCAGTGGTCATGATGTTTTGTCCTGGAATAGAAACCTTGACTAAGACAATAGTTATAG

GTAACAAGAAGAGAGCTGTGAACTCGTCATGTAGTTAAGTGTTTGCTAGATTTCCTATTGCATAG

TTCCTATTTTCTCTTTATATTTGGAAAAAAATTGTGGTAACATACCTTAGACACTTATTGTTGTT

CTCCTCCCTGACCTGCACTCAATGAATTCTCAGCCAAACTCTAGTGATGTCCTCCCCATTCAAAA

GCTTCAACCTTCTAGTCTTTATTTTAAAAAATGTTATTATTACATTTATTTATTCTGTGGTGTGT

GTGTGTGAGAGAGAGGATGGGAGCAGGTGTGTGTGTGTGTGTCGGTGTGTTTGTTAAATCAGAAC

ATGAGTGTGTGTGTAAGACAGAGACGGGGTGAGTGTGTGTGTGTGTGTGTGTGTGTGTGTGTGTC

AGTGGATAAGTTGTAGAAGTCAGTTCTTTCCTTCCCTTACTCGGACCTCAGGGATCAAACTCAAG

TTCTCAGGTTGCCAGGTACATGTCACCTGTOTTTGCTTTATTATTATTTAGTTCTGGCTTTTGAG

CCTAAGTGTTATGTTACATAGGTTGACCTTGAATTAGCTATGCACTGAGGTCCTGATCCTCCTGC

CTTTATCTTCCAAGTAATGGTTACAGGAATGGGCCACTGGACCTAGCAAGTGAACCTACCTGGTC

ACTCCAAAAATGCACAGCAAAGAATATACGTTTAAAAATAGGTTCATTTTAGGAAGTTTGTCCAC

ATTTTAAATGACAGTTCTGTTAAAGTATACTGTGTTTTGTCCTTTGTTAAATGTGACTTTTAAAA

GCAATTCACCTTAATAGCCTGGGCGACTACAGTGCTCACTGTATAAATGCTAGTGTGTTTTTGGT

GCTGAAACAGAAAGGTGGCTCTAGAAAGCTGGAGTTCCTCATCTTTAAGTTCCAGACTGAGATAT

CTAGAACTTCTTCAAAAATCCAGGGAAAGGAAAGCGATGGAAGTGAAAATAAAAACAAGAACATG

CTTTACATATATTTGATTGTGATCCCTTTGGCGGGTACTAGGAAAACCACGGATGGAATTTTCCT

TCTTGAAAGAGGTGAGGAGCAGGCAGAATGTGAACATCTACTTAATGAGCTGAACTGGCCGGTGC

CCTCAGAATTGTAAACAGGTTCACCACAAATCCAGGCCTTGGCAAACAGACCAAGTOTTCCTCTC

TTCGGTTTTCTTTTTACAGACTGGCTTTCTTGACAACTTCAAGATGGAGTCTCATCCTTGCCCTT

TTTATGGAGAGGAGAAGCATTGCTTCTAGTTGGTTTTAGTAGAGGAGTGAAGTGCATTTCTCAGA

TACAAAGAGAGCACTTGAGACGTTCAGACTCAGAATGGCCAAGCCTGGCACTTTGGGAGGTCAAG

AGGAGGCTGGAACGGCTGGGAGAGAAAGCAATTAGATGTTCCACCCCTTTGGTTTTTCTCCAGAC

AGGGTTTCTCTGTGTAGCCCTGACTGTCCTGAAGTTTGCTCTGTAGACCAGGCTGGCCTCCACCC

AGGGATTTGCCTGCCTCTGCCTCCCCGAGCCCCAGATTTTTATTTTTATTTATTTATATATCTAT

TTTAACTTTTGAATGAACACAATGGAATTGATGAGCCCTTGGAGAGAGAAACGGGATGTCGTGCG

TGGCAGCCCCGGGGATCAGCTCACTCCCACAGGCCTCACAGGCCATGGAGCCAAGAGGCCTCCCT

GCCTCGGCCTCGGCCTCGGCCTCAACAAAGGTGGAGAACGCGCAGGCCGTCCGTCCATGGGGCGG

-continued

GAAGTCGCGCGCCGCGGCCGCTGATTGGCTGGCGGGCCCGGTCGCCTGATGCTATTTGTTGTCCC

CGCGCCAATGACGCAGTCGGCGTCCCGGCGTCCGCCCGCACGTGCAGCCGTTTAAGCCGCGTCGG

CCGGCCGCGAGGAGCCCGGGGAGCCTGGAGCGGAGA

SEQ ID NO: 2 c-kit Promoter - Mus musculus
AGGGAGAGTGCTAGGAGGAAGAGGATCCAGGGTGAAGGGCCTGTGGGGGCTCCTGGTCTTAGAGG

GCACAGCGCCCCCGGGATCAGCTTATTGCAGCCCGAGAGCCCCGGGCACTAGGCAGCGGGAGGGA

GTGCGACCCGGGCGGGAGAAGGGAGGGGCGTGGCCACGAGCTGGGAGGAGGGCTGGAGGAGGGGC

TGTCGCGCGCCGCTAGTGGCTCTGGGGGCTCGGCTTTGCCGCGCTCGGTGCACTTGGGCGAGAGC

TGTAGCAGAGAGAGGAGCTCAGAGTCTAGCGCAGCCACCGCGATGAGAGGCGCTCGCGGCGCCTG

GGATCTGCTCTGCGTCCTGTTGGTCCTGCTCCGTGGCCAGACAGGTGGGAAAGAGCGGCAGACAA

GAGGACTGCACCCTCTGTGGGCGCAGCCCGGGTCCGGG

SEQ ID NO: 3 Artificial sequence - Transcription factor binding sequence
GTTCTCACGTGGCCTG SEQ ID NO: 4 Artificial sequence - Transcription factor binding sequence
CTCACGTGGC SEQ ID NO: 5 Artificial sequence - Transcription factor binding sequence
AGGCAAGGCAACATAA SEQ ID NO: 6 Artificial sequence - Transcription factor binding sequence
TTGTTCTCACGTGGCCTGTG SEQ ID NO: 7 Artificial sequence - Transcription factor binding sequence
GTGTTAACGTCTGAA SEQ ID NO: 8 Artificial sequence - Transcription factor binding sequence
TTCCTGGTCAAGGTCAGA SEQ ID NO: 9 Artificial sequence - Transcription factor binding sequence
CACAGCTGGG SEQ ID NO: 10 Artificial sequence - Transcription factor binding sequence
CTATAAACAGACCTCT SEQ ID NO: 11 Artificial sequence - Transcription factor binding sequence
GTCATAGATAAGCTT SEQ ID NO: 12 Artificial sequence - Transcription factor binding sequence
CACCGAGAAGTATGA SEQ ID NO: 13 Artificial sequence - Transcription factor binding sequence
CAGCACTGCCTCATAGATGA SEQ ID NO: 14 Artificial sequence - Transcription factor binding sequence
GGACCGCCATCTGCCGGGGA SEQ ID NO: 15 Artificial sequence - Transcription factor binding sequence
GATCTGCCATCCTGCCTGCC SEQ ID NO: 16 Artificial sequence - Transcription factor binding sequence
CAATTCCTGGAACTC SEQ ID NO: 17 Artificial sequence - Transcription factor binding sequence
TTCCAGGAATTGCACCACCTGGTG SEQ ID NO: 18 Artificial sequence - Transcription factor binding sequence
TTCCCAGTAGTGGCGACCCCAAGA SEQ ID NO: 19 Artificial sequence - Transcription factor binding sequence
CTGTTGTTCACCAG SEQ ID NO: 20 Artificial sequence - Transcription factor binding sequence
TGAGAGGGTTTCGG SEQ ID NO: 21 Artificial sequence - Transcription factor binding sequence
GGAAGTGGGTCAC SEQ ID NO: 22 Artificial sequence - Transcription factor binding sequence
TGAGAGGGTTTCGG -continued SEQ ID NO: 23 Artificial sequence - Transcription factor binding sequence
GAGTCCAGGTGTTGGG SEQ ID NO: 24 Artificial sequence - Transcription factor binding sequence
TCCACCAGGTGGTGCA SEQ ID NO: 25 Artificial sequence - Transcription factor binding sequence
GACTGGGCAAAAGTTCA SEQ ID NO: 26 Artificial sequence - Transcription factor binding sequence
TATTGTTTGTTT SEQ ID NO: 27 Artificial sequence - Transcription factor binding sequence
CAAGGCCTCTGGCGTT SEQ ID NO: 28 Artificial sequence - Transcription factor binding sequence
GTCGTCAATCATGCC SEQ ID NO: 29 Artificial sequence - Transcription factor binding sequence
CAAGCGTGTG SEQ ID NO: 30 Artificial sequence - Transcription factor binding sequence
TGGGGAACGTGTTCCC SEQ ID NO: 31 Artificial sequence - Transcription factor binding sequence
GTTAGCACGTGAAGGA SEQ ID NO: 32 Artificial sequence - Transcription factor binding sequence
GGTGAGTCAGC SEQ ID NO: 33 Artificial sequence - Transcription factor binding sequence
AGCTGACTCAC SEQ ID NO: 34 Artificial sequence - Transcription factor binding sequence
CTCATTTACATAC SEQ ID NO: 35 Diphtheria toxin A fragment from Corynebacterium diphtheriae
CTGATGATGTTGTTGATTCTTCTAAATCTTTTGTGATGGAAAACTTTTCTTCGTACCACGGGACT

AAACCTGGTTATGTAGATTCCATTCAAAAAGGTATACAAAAGCCAAAATCTGGTACACAAGGAAA

TTATGACGATGATTGGAAAGGGTTTTATAGTACCGACAATAAATACGACGCTGCGGGATACTCTG

TAGATAATGAAAACCCGCTCTCTGGAAAAGCTGGAGGCGTGGTCAAAGTGACGTATCCAGGACTG

ACGAAGGTTCTCGCACTAAAAGTGGATAATGCCGAAACTATTAAGAAAGAGTTAGGTTTAAGTCT

CACTGAACCGTTGATGGAGCAAGTCGGAACGGAAGAGTTTATCAAAAGGTTCGGTGATGGTGCTT

CGCGTGTAGTGCTCAGCCTTCCCTTCGCTGAGGGGAGTTCTAGCGTTGAATATATTAATAACTGG

GAACAGGCGAAAGCGTTAAGCGTAGAACTTGAGATTAATTTTGAAACCCGTGGAAAACGTGGCCA

AGATGCGATGTATGAGTATATGGCTCAAGCCTGTGCAGGAAATCGTGTCAGGCGATC

SEQ ID NO: 36 Artificial sequence - RNAi/shRNA target sequence for mouse oct3/4
GGATGTGGTTCGAGTATGGT SEQ ID NO: 37 Artificial sequence - SNP sequence
TCCCTGGAGAATTGACCCGTATATGGCCACGT SEQ ID NO: 38 Artificial sequence SNP sequence
TCCCTGTGGAACTGACCTTTATACGGCCACGT SEQ ID NO: 39 Oct3/4 Promoter - Mus musculus
ACTGTGAGGGGATGGAGCCTGGGTGCAGGTCTTATGGGGGTTGGGGGGTGGTTAGTGTCTAATCT

ACCAACCTGGACAACACAAGATGGAATACTGTGCTCTGAAAACGCAGAGCCAGCACTTCTCTGGG

GTCTCTGGGGACATATCTGGTTGGGGCTCGGGGTCCCATGGTGTAGAGCCTCTAAACTCTGGAGG

ACTGGAGGTGCAATGGCTGTCTTGTCCTGGCCTTGGACATGGGCTGAAATACTGGGTTCACCCAT

ATCTAGGACTCTAGACGGGTGGGTAAGCAAGAACTGAGGAGTGGCCCCAGAAATAATTGGCACAC

GAACATTCAATGGATGTTTTAGGCTCTCCAGAGGATGGCTGAGTGGGCTGTAAGGACAGGCCGAG

AGGGTGCAGTGCCAACAGGCTTTGTGGTGCGATGGGGCATCCGAGCAACTGGTTTGTGAGGTGTC

CGGTGACCCAAGGCAGGGGTGAGAGGACCTTGAAGGTTGAAAATGAAGGCCTCCTGGGGTCCCGT

CCTAAGGGTTGTCCTGTCCAGACGTCCCCAACCTCCGTCTGGAAGACACAGGCAGATAGCGCTCG

CCTCAGTTTCTCCCACCCCCACAGCTCTGCTCCTCCACCCACCCAGGGGGCGGGGCCAGAGGTCA

AGGCTAGAGGGTGGGATTGGGGAGGGA

SEQ ID NO: 40 Artificial sequence - Primer sequence for genotyping
CACGTGCAGCCGTTTAAGCCGCGT
SEQ ID NO: 41 Artificial sequence - Primer sequence for genotyping
TTCCCATTCTAAACACCCTGAA
SEQ ID NO: 42 Artificial sequence -Primer sequence for genotyping
CTAGGCCACAGAATTGAAAGATCT
SEQ ID NO: 43 Artificial sequence - Primer sequence for genotyping
GTAGGTGGAAATTCTAGCATCATCC
SEQ ID NO: 44 Artificial sequence - Primer sequence for genotyping
GTTATCAGTAAGGGAGCTGCAGTGG
SEQ ID NO: 45 Artificial sequence - Primer sequence for genotyping
GGCGGATCACAAGCAATAATAACC
SEQ ID NO: 46 Artificial sequence -Primer sequence for genotyping
AAGACCGCGAAGAGTTTGTCCTC
SEQ ID NO: 47 Diphtheria toxin A fragment (DTA) protein from Corynebacterium diphtheriae
MDPDDVVDSSKSFVMENFSSYHGTKPGYVDSIQKGIQKPKSGTQGNYDDDWKGFYSTDNKYDAAG

YSVDNENPLSGKAGGVVKVTYPGLTKVLALKVDNAETIKKELGLSLTEPLMEQVGTEEFIKRFGD

GASRVVLSLPFAEGSSSVEYINNWEQAKALSVELEINFETRGKRGQDAMYEYMAQACAGNRVRRS

L

SEQ ID NO: 48 Diphtheria toxin A mutant, tox176 protein from Corynebacterium diphtheriae
EADDVVDSSKSFVMENFSSYHGTKPGYVDSIQKGIQKPKSGTQGNYDDDWKGFYSTDNKYDAAGY

SVDNENPLSGKAGGVVKVTYPGLTKVLALKVDNAETIKKELGLSLTEPLMEQVGTEEFIKRFDDG

ASRVVLSLPFAEGSSSVEYINNWEQAKALSVELEINFETRGKRGQDAMYEYMAQACAGNRVRR

SEQ ID NO: 49 Herpes simplex virus thymidine kinase from Human herpesvirus 1
ATGGCCAGCTACCCCTGTCACCAGCACGCCAGCGCCTTCGACCAGGCCGCTAGAAGCAGAGGCCA

CAGCAACAGAAGAACCGCCCTGAGACCCAGAAGACAGCAGGAGGCCACAGAGGTGAGACTGGAGC

AGAAGATGCCCACCCTGCTGAGAGTGTACATCGATGGACCCCACGGCATGGGCAAGACCACAACA

ACCCAGCTGCTGGTGGCCCTGGGCAGCAGAGACGACATCGTGTACGTGCCCGAGCCCATGACCTA

CTGGCAGGTGCTGGGAGCCAGCGAGACCATCGCCAACATCTACACCACACAGCACAGACTGGACC

AGGGCGAGATCAGCGCCGGCGACGCTGCCGTGGTGATGACCAGCGCCCAGATCACAATGGGCATG

CCCTACGCCGTGACCGATGCCGTGCTGGCTCCCCACGTGGGCGGAGAGGCCGGCAGCAGCCACGC

CCCTCCCCCTGCCCTGACCCTGATCTTCGACAGACACCCCATCGCCGCCCTGCTGTGCTACCCCG

CCGCTAGATACCTGATGGGCAGCATGACACCCCAGGCCGTGCTGGCCTTCGTGGCCCTGATCCCC

CCTACCCTGCCCGGCACCAACATCGTGCTGGGCGCCCTGCCCGAGGACAGACACATCATGGCTTC

GTACCCCTGCCATCAACACGCGTCTGCGTTCGACCAGGCTGCGCGTTCTCGCGGCCATAGCAACC

GACGTACGGCGTTGCGCCCTCGCCGGCAGCAAGAAGCCACGGAAGTCCGCCTGGAGCAGAAAATG

CCCACGCTACTGCGGGTTTATATAGACGGTCCTCACGGGATGGGGAAAACCACCACCACGCAACT

GCTGGTGGCCCTGGGTTCGCGCGACGATATCGTCTACGTACCCGAGCCGATGACTTACTGGCAGG

TGCTGGGGGCTTCCGAGACAATCGCGAACATCTACACCACACAACACCGCCTCGACCAGGGTGAG

ATATCGGCCGGGGACGCGGCGGTGGTAATGACAAGCGCCCAGATAACAATGGGCATGCCTTATGC

CGTGACCGACGCCGTTCTGGCTCCTCATATCGGGGGGGAGGCTGGGAGCTCACATGCCCCGCCCC

CGGCCCTCACCCTCATCTTCGACCGCCATCCCATCGCCGCCCTCCTGTGCTACCCGGCCGCGCGA

TACCTTATGGGCAGCATGACCCCCCAGGCCGTGCTGGCGTTCGTGGCCCTCATCCCGCCGACCTT

GCCCGGCACAAACATCGTGTTGGGGGCCCTTCCGGAGGACAGACACATCGACCGCCTGGCCAAAC

GCCAGCGCCCCGGCGAGCGGCTTGACCTGGCTATGCTGGCCGCGATTCGCCGCGTTTACGGGCTG

-continued

```
CTTGCCAATACGGTGCGGTATCTGCAGGGCGGCGGGTCGTGGCGGGAGGATTGGGGACAGCTTTC

GGGGACGGCCGTGCCGCCCCAGGGTGCCGAGCCCCAGAGCAACGCGGGCCCACGACCCCATATCG

GGGACACGTTATTTACCCTGTTTCGGGCCCCCGAGTTGCTGGCCCCCAACGGCGACCTGTACAAC

GTGTTTGCCTGGGCCTTGGACGTCTTGGCCAAACGCCTCCGTCCCATGCACGTCTTTATCCTGGA

TTACGACCAATCGCCCGCCGGCTGCCGGGACGCCCTGCTGCAACTTACCTCCGGGATGATCCAGA

CCCACGTCACCACCCCAGGCTCCATACCGACGATCTGCGACCTGGCGCGCACGTTTGCCCGGGAG

ATGGGGGAGGCTAACTAA
```

SEQ ID NO: 50 Herpes simplex virus thymidine kinase protein sequence from Human herpesvirus 1

```
MASYPGHQHASAFDQAARSRGHSNRRTALRPRRQQEATEVRPEQKMPTLLRVYIDGPHGMCKTTT

TQLLVALGSRDDIVYVPEPMTYWRVLGASETIANIYTTQHRLDQGEISAGDAAVVMTSAQITMGM

PYAVTDAVLAPHIGGEAGSSHAPPPALTLIFDRHPIAALLCYPAARYLMGSMTPQAVLAFVALIP

PTLPGTNIVLGALPEDRHIDRLAKRQRPGERLDLAMLAAIRRVYGLLANTVRYLQGGGSWREDWG

QLSGTAVPPQGAEPQSNAGPRPHIGDTLFTLFRAPELLAPNGDLYNVFAWALDVLAKRLRPMHVF

ILDYDQSPAGCRDALLQLTSGMIQTHVTTPGSIPTICDLARTFAREMGEAN
```

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A preimplantation mouse or rat host embryo incapable of developing endogenous gametes, the preimplantation mouse or rat host embryo capable of ablating germ cells during the period of embryonic day 6 to embryonic day 14 of the mouse embryo or during the period of embryonic day 7 to embryonic day 16 of the rat embryo, and developing a receptive, empty germ cell niche, the preimplantation mouse or rat host embryo comprising a transgene encoding a recombinase operably linked to a vasa promoter and a transgene encoding diphtheria toxin operably linked to a ubiquitous promoter, wherein the transgene encoding diphtheria toxin is operably linked to a ubiquitous promoter and the transgene has a loxP-flanked stop cassette operably linked to at least two recombinase recognition sites.

* * * * *

SEQUENCE LISTING

<160> NUMBER OF SEQ ID NOS: 50

<210> SEQ ID NO 1
<211> LENGTH: 5366
<212> TYPE: DNA
<213> ORGANISM: Mus musculus

<400> SEQUENCE: 1

```
tgtgccacca tgcctggccc agtttcttgc tttgtattat aaactttata gctggtaaga     60

ctctggaccc acacgtgttt gatttgtctc ttctctcctg agacattttt tcccagtaac    120

atttcctgaa ttttgtattt tattgtctct gcatctgtgc tgagacataa catcttctgt    180

ttcttctatt tgccatgaac tgggagttaa gtctaagaat ttgattaaag ctgaagttga    240

gtttgaaatc aaacctctac atgtagcgtt ttgtatttcc cactgtgata catcaaccag    300

cacatggttc ttggaggtct ttgctttgtg gtataaagtt ggcccagtgt gtttaaatgt    360

tgtcctcttt aaggaggtag ctaggtaaga tcacacgccg gttacctacc tccctactga    420

tgcactaact ggtgtgtcta gcctagccta aggccctagg gtaccatgca tcccataata    480

gcttatgtga ggcccaacac atttgtagat aacagcatca ggtcatagtg tcataaggtt    540

ggacacccct ggcagagttt cctgtaccac actatcttca aaagagctaa agaagtaagg    600

tggaaaaaaa caaacatcat agtgttctga ttttactgta acaggaaaag actcactgaa    660

aagatgccaa ggcccagatt tcccctccca caattccaag cttcatggag aatgatacct    720

ccactttggg gatggagaag gaattaaatc ctgaccacag acttgaagca gtaagaactt    780

atcaccgtga tgtcagttct gggtggaacc ctatgcatcc cgtggccctg tacctgcaga    840
```

-continued

```
tgctgctgct ggacctgtga tagatggcca gtactacagt taggaatctt tctgacaact    900
gcagctttta gaatggaaat caaaactcca cctactggat ggcacaacat gaaagcaagg    960
actgtgcctt gcagctcagg gccagcctta gtactagtct ctgagggacc gttgctacca   1020
ccggttccca acctgtagca gcacaactat cctggaccag ggttcacgga tggagctcaa   1080
gaccttgaca tctgtcacag ttatgctctg caccatgagg aagttgtctc agtttgcctt   1140
actgccacag caccggctgt gggctcagca ttgtgacact cagagccaca gttctggagc   1200
aggaaccagg gcaggtccct ctggtgattc tttctacagt tcacgaccag aggctgttgg   1260
ctttggaagg cacctggagg tctgtgcaag ccccggacag aggcttgtgt agatgaagga   1320
ccctttataa aaagctccct aattgagtct tgaaaaactc acccgctgag gatttaggag   1380
aaacctaagc ttggatcgcc tcctaacact gccacaggta acctgaattt tggtgccata   1440
tagtgttaga aactataggc tgagagagag agagaaaaaa aaaacattct tttttcaatt   1500
tctgaaaaca aacaaaacca aaacaagcca tattatgaag accggaataa atacctaatc   1560
ctttgtcctc gaatgacatc acacatcaat aagaaccaag gatgtttaag gaactatgac   1620
ctcatctgac agtataaata taaaatgcca gaaaccgtca agatagtaac cagtgtgggt   1680
ggatgctcat atgtgtactg tattagttac tttttcattg ttgtgataaa ataccacgac   1740
taaagcctga cttataggag aaggaatttg tcctggcttg tgttttcaga gtgatatgac   1800
tccatcatga cagggacgca tggaagccag caacaggtat gatgctgggg cagcaagctg   1860
agagctcaca tccgccactg aaggcacaaa acagcaagtg tgagctggaa gtggtgtgag   1920
gctatatact agcaaaggct gccctactga tacgctgtct ccaggaggac tgcattcccc   1980
aagcttctct gatcatcaca accaactgag aactaaatgg tcaaatacct gggtcagtgg   2040
ggatcatttc tcattcaaac ttccacagat aattaaaagc aaataaatga accaggttta   2100
aggaaactta ctgaattcca atagaaaata tagaaataaa tcaatacttt agtagatata   2160
attgactgag acatgggggc aaattttaaa aagttgaaat tcttgataat gaaggtatac   2220
taaacaaaat aaaattgcat tagggaagca ttgatgttag agtaaatcaa gcagaagaga   2280
gaatgagtga attccaacat aggccatttg aaaatgcaca gaagagaaaa agaattaaga   2340
ggaagaaatg tactcatggt aaccttggag caacagtgaa agggtaagta ggttagtggg   2400
gatatggacg ggacttgaga acaccaaaag agttaatcga tgcaactacg ttatgatcaa   2460
acacagtcag gttccaggtt ctgcagtaaa ctgaatctcc agttttcacg ttatgtagat   2520
ccatctccat gaatctggcc tggccttgtg aatttctggt aactgattag ttgaaagttg   2580
caaatataat tgtttaactt cttatgctag aattcaagaa gccttgcaac tattaccctg   2640
gtcctttgga gcgatgtccc tgacaagtgt gtccagttga aatgcagcat ccttacagag   2700
tctgactgag attgtccaac aaccttcaga gcctaagtca gcctcttgga aactattcaa   2760
ttgttctggc catcccagcc actagatgcc agagtagaga agtcaccttg gatgttaaac   2820
aaactggtat tggaggttgg ggataaactc agtagtacag agcttgcctg gcacgctcaa   2880
gtacctaggt tcaaactctg gcaatgccaa aaaagaaaaa agttgatagc aaactctcag   2940
atgattcaag ttctaattag catttgaatg gaattgtatg agatggtctc ctgagccctc   3000
tcaatccctg agagagaatt ttttttgtaa gtcaatatat tatgcaatag tttgttatat   3060
agttgtactg gctaatttgg gtcaagctgg agttatcaca gagaaaggag cttcagttgg   3120
ggaaatgcct ccatgagatc caactgtaag gcattttctc aattagtgat caagggggaa   3180
aggccccttg tgggtaggac catctctggg ctggtagtct tggttctata agagagcagg   3240
```

```
ctgagcaagc cagtaaggaa catccctcca tggcctctgc atcagctcct gctcctgacc   3300

tgcttgagtt ccagtcctga cttcctttgg tgatgaacag caatgtggaa agtgtaagct   3360

gaataaaccc tttcctcccc aatttgctca gtggtcatga tgttttgtcc tggaatagaa   3420

accttgacta agacaatagt tataggtaac aagaagagag ctgtgaactc gtcatgtagt   3480

taagtgtttg ctagatttcc tattgcatag ttcctatttt ctctttatat ttggaaaaaa   3540

attgtggtaa cataccttag acacttattg ttgttctcct ccctgacctg cactcaatga   3600

attctcagcc aaactctagt gatgtcctcc ccattcaaaa gcttcaacct tctagtcttt   3660

attttaaaaa atgttattat tacatttatt tattctgtgg tgtgtgtgtg tgagagagag   3720

gatgggagca ggtgtgtgtg tgtgtgtcgg tgtgtttgtt aaatcagaac atgagtgtgt   3780

gtgtaagaca gagacggggt gagtgtgtgt gtgtgtgtgt gtgtgtgtgt gtgtcagtgg   3840

ataagttgta gaagtcagtt ctttccttcc cttactcgga cctcagggat caaactcaag   3900

ttctcaggtt gccaggtaca tgtcacctgt ctttgcttta ttattattta gttctggctt   3960

ttgagcctaa gtgttatgtt acataggttg accttgaatt agctatgcac tgaggtcctg   4020

atcctcctgc ctttatcttc caagtaatgg ttacaggaat gggccactgg acctagcaag   4080

tgaacctacc tggtcactcc aaaaatgcac agcaaagaat atacgtttaa aaataggttc   4140

attttaggaa gtttgtccac attttaaatg acagttctgt taaagtatac tgtgttttgt   4200

cctttgttaa atgtgacttt taaaagcaat tcaccttaat agcctgggcg actacagtgc   4260

tcactgtata aatgctagtg tgtttttggt gctgaaacag aaaggtggct ctagaaagct   4320

ggagttcctc atctttaagt tccagactga gatatctaga acttcttcaa aaatccaggg   4380

aaaggaaagc gatggaagtg aaaataaaaa caagaacatg ctttacatat atttgattgt   4440

gatccctttg gcgggtacta ggaaaaccac ggatggaatt ttccttcttg aaagaggtga   4500

ggagcaggca gaatgtgaac atctacttaa tgagctgaac tggccggtgc cctcagaatt   4560

gtaaacaggt tcaccacaaa tccaggcctt ggcaaacaga ccaagtcttc ctctcttcgg   4620

ttttcttttt acagactggc tttcttgaca acttcaagat ggagtctcat ccttgccctt   4680

tttatggaga ggagaagcat tgcttctagt tggttttagt agaggagtga agtgcatttc   4740

tcagatacaa agagagcact tgagacgttc agactcagaa tggccaagcc tggcactttg   4800

ggaggtcaag aggaggctgg aacggctggg agagaaagca attagatgtt ccacccettt   4860

ggtttttctc cagacagggt ttctctgtgt agccctgact gtcctgaagt ttgctctgta   4920

gaccaggctg gcctccaccc agggatttgc ctgcctctgc ctccccgagc cccagatttt   4980

tatttttatt tatttatata tctattttaa cttttgaatg aacacaatgg aattgatgag   5040

cccttggaga gagaaacggg atgtcgtgcg tggcagcccc ggggatcagc tcactcccac   5100

aggcctcaca ggccatggag ccaagaggcc tccctgcctc ggcctcggcc tcggcctcaa   5160

caaaggtgga gaacgcgcag gccgtccgtc catggggcgg gaagtcgcgc gccgcggccg   5220

ctgattggct ggcgggcccg gtcgcctgat gctatttgtt gtccccgcgc caatgacgca   5280

gtcggcgtcc cggcgtccgc ccgcacgtgc agccgtttaa gccgcgtcgg ccggccgcga   5340

ggagcccggg gagcctggag cggaga                                         5366
```

<210> SEQ ID NO 2
<211> LENGTH: 428
<212> TYPE: DNA
<213> ORGANISM: Mus musculus

<400> SEQUENCE: 2

```
agggagagtg ctaggaggaa gaggatccag ggtgaagggc ctgtgggggc tcctggtctt     60

agagggcaca gcgcccccgg gatcagctta ttgcagcccg agagccccgg gcactaggca    120

gcgggaggga gtgcgacccg ggcgggagaa gggaggggcg tggccacgag ctgggaggag    180

ggctggagga ggggctgtcg cgcgccgcta gtggctctgg gggctcggct ttgccgcgct    240

cggtgcactt gggcgagagc tgtagcagag agaggagctc agagtctagc gcagccaccg    300

cgatgagagg cgctcgcggc gcctgggatc tgctctgcgt cctgttggtc ctgctccgtg    360

gccagacagg tgggaaagag cggcagacaa gaggactgca ccctctgtgg gcgcagcccg    420

ggtccggg                                                              428


<210> SEQ ID NO 3
<211> LENGTH: 16
<212> TYPE: DNA
<213> ORGANISM: artificial
<220> FEATURE:
<223> OTHER INFORMATION: Transcription factor binding sequence

<400> SEQUENCE: 3

gttctcacgt ggcctg                                                      16


<210> SEQ ID NO 4
<211> LENGTH: 10
<212> TYPE: DNA
<213> ORGANISM: artificial
<220> FEATURE:
<223> OTHER INFORMATION: Transcription factor binding sequence

<400> SEQUENCE: 4

ctcacgtggc                                                             10


<210> SEQ ID NO 5
<211> LENGTH: 16
<212> TYPE: DNA
<213> ORGANISM: artificial
<220> FEATURE:
<223> OTHER INFORMATION: Transcription factor binding sequence

<400> SEQUENCE: 5

aggcaaggca acataa                                                      16


<210> SEQ ID NO 6
<211> LENGTH: 20
<212> TYPE: DNA
<213> ORGANISM: artificial
<220> FEATURE:
<223> OTHER INFORMATION: Transcription factor binding sequence

<400> SEQUENCE: 6

ttgttctcac gtggcctgtg                                                  20


<210> SEQ ID NO 7
<211> LENGTH: 15
<212> TYPE: DNA
<213> ORGANISM: artificial
<220> FEATURE:
<223> OTHER INFORMATION: Transcription factor binding sequence

<400> SEQUENCE: 7

gtgttaacgt ctgaa                                                       15


<210> SEQ ID NO 8
<211> LENGTH: 18
<212> TYPE: DNA
```

<213> ORGANISM: artificial
<220> FEATURE:
<223> OTHER INFORMATION: Transcription factor binding sequence

<400> SEQUENCE: 8
ttcctggtca aggtcaga 18

<210> SEQ ID NO 9
<211> LENGTH: 10
<212> TYPE: DNA
<213> ORGANISM: artificial
<220> FEATURE:
<223> OTHER INFORMATION: Transcription factor binding sequence

<400> SEQUENCE: 9
cacagctggg 10

<210> SEQ ID NO 10
<211> LENGTH: 16
<212> TYPE: DNA
<213> ORGANISM: artificial
<220> FEATURE:
<223> OTHER INFORMATION: Transcription factor binding sequence

<400> SEQUENCE: 10
ctataaacag acctct 16

<210> SEQ ID NO 11
<211> LENGTH: 15
<212> TYPE: DNA
<213> ORGANISM: artificial
<220> FEATURE:
<223> OTHER INFORMATION: Transcription factor binding sequence

<400> SEQUENCE: 11
gtcatagata agctt 15

<210> SEQ ID NO 12
<211> LENGTH: 15
<212> TYPE: DNA
<213> ORGANISM: artificial
<220> FEATURE:
<223> OTHER INFORMATION: Transcription factor binding sequence

<400> SEQUENCE: 12
caccgagaag tatga 15

<210> SEQ ID NO 13
<211> LENGTH: 20
<212> TYPE: DNA
<213> ORGANISM: artificial
<220> FEATURE:
<223> OTHER INFORMATION: Transcription factor binding sequence

<400> SEQUENCE: 13
cagcactgcc tcatagatga 20

<210> SEQ ID NO 14
<211> LENGTH: 20
<212> TYPE: DNA
<213> ORGANISM: artificial
<220> FEATURE:
<223> OTHER INFORMATION: Transcription factor binding sequence

<400> SEQUENCE: 14
ggaccgccat ctgccgggga 20

<210> SEQ ID NO 15
<211> LENGTH: 20
<212> TYPE: DNA
<213> ORGANISM: artificial
<220> FEATURE:
<223> OTHER INFORMATION: Transcription factor binding sequence

<400> SEQUENCE: 15
gatctgccat cctgcctgcc 20

<210> SEQ ID NO 16
<211> LENGTH: 15
<212> TYPE: DNA
<213> ORGANISM: artificial
<220> FEATURE:
<223> OTHER INFORMATION: Transcription factor binding sequence

<400> SEQUENCE: 16
caattcctgg aactc 15

<210> SEQ ID NO 17
<211> LENGTH: 24
<212> TYPE: DNA
<213> ORGANISM: artificial
<220> FEATURE:
<223> OTHER INFORMATION: Transcription factor binding sequence

<400> SEQUENCE: 17
ttccaggaat tgcaccacct ggtg 24

<210> SEQ ID NO 18
<211> LENGTH: 24
<212> TYPE: DNA
<213> ORGANISM: artificial
<220> FEATURE:
<223> OTHER INFORMATION: Transcription factor binding sequence

<400> SEQUENCE: 18
ttcccagtag tggcgacccc aaga 24

<210> SEQ ID NO 19
<211> LENGTH: 14
<212> TYPE: DNA
<213> ORGANISM: artificial
<220> FEATURE:
<223> OTHER INFORMATION: Transcription factor binding sequence

<400> SEQUENCE: 19
ctgttgttca ccag 14

<210> SEQ ID NO 20
<211> LENGTH: 14
<212> TYPE: DNA
<213> ORGANISM: artificial
<220> FEATURE:
<223> OTHER INFORMATION: Transcription factor binding sequence

<400> SEQUENCE: 20
tgagagggtt tcgg 14

<210> SEQ ID NO 21
<211> LENGTH: 13
<212> TYPE: DNA
<213> ORGANISM: artificial
<220> FEATURE:
<223> OTHER INFORMATION: Transcription factor binding sequence

<400> SEQUENCE: 21
ggaagtgggt cac 13

<210> SEQ ID NO 22
<211> LENGTH: 14
<212> TYPE: DNA
<213> ORGANISM: artificial
<220> FEATURE:
<223> OTHER INFORMATION: Transcription factor binding sequence

<400> SEQUENCE: 22
tgagagggtt tcgg 14

<210> SEQ ID NO 23
<211> LENGTH: 16
<212> TYPE: DNA
<213> ORGANISM: artificial
<220> FEATURE:
<223> OTHER INFORMATION: Transcription factor binding sequence

<400> SEQUENCE: 23
gagtccaggt gttggg 16

<210> SEQ ID NO 24
<211> LENGTH: 16
<212> TYPE: DNA
<213> ORGANISM: artificial
<220> FEATURE:
<223> OTHER INFORMATION: Transcription factor binding sequence

<400> SEQUENCE: 24
tccaccaggt ggtgca 16

<210> SEQ ID NO 25
<211> LENGTH: 17
<212> TYPE: DNA
<213> ORGANISM: artificial
<220> FEATURE:
<223> OTHER INFORMATION: Transcription factor binding sequence

<400> SEQUENCE: 25
gactgggcaa aagttca 17

<210> SEQ ID NO 26
<211> LENGTH: 12
<212> TYPE: DNA
<213> ORGANISM: artificial
<220> FEATURE:
<223> OTHER INFORMATION: Transcription factor binding sequence

<400> SEQUENCE: 26
tattgtttgt tt 12

<210> SEQ ID NO 27
<211> LENGTH: 16
<212> TYPE: DNA
<213> ORGANISM: artificial
<220> FEATURE:
<223> OTHER INFORMATION: Transcription factor binding sequence

<400> SEQUENCE: 27
caaggcctct ggcgtt 16

<210> SEQ ID NO 28
<211> LENGTH: 15
<212> TYPE: DNA

<213> ORGANISM: artificial
<220> FEATURE:
<223> OTHER INFORMATION: Transcription factor binding sequence

<400> SEQUENCE: 28
gtcgtcaatc atgcc 15

<210> SEQ ID NO 29
<211> LENGTH: 10
<212> TYPE: DNA
<213> ORGANISM: artificial
<220> FEATURE:
<223> OTHER INFORMATION: Transcription factor binding sequence

<400> SEQUENCE: 29
caagcgtgtg 10

<210> SEQ ID NO 30
<211> LENGTH: 16
<212> TYPE: DNA
<213> ORGANISM: artificial
<220> FEATURE:
<223> OTHER INFORMATION: Transcription factor binding sequence

<400> SEQUENCE: 30
tggggaacgt gttccc 16

<210> SEQ ID NO 31
<211> LENGTH: 16
<212> TYPE: DNA
<213> ORGANISM: artificial
<220> FEATURE:
<223> OTHER INFORMATION: Transcription factor binding sequence

<400> SEQUENCE: 31
gttagcacgt gaagga 16

<210> SEQ ID NO 32
<211> LENGTH: 11
<212> TYPE: DNA
<213> ORGANISM: artificial
<220> FEATURE:
<223> OTHER INFORMATION: Transcription factor binding sequence

<400> SEQUENCE: 32
ggtgagtcag c 11

<210> SEQ ID NO 33
<211> LENGTH: 11
<212> TYPE: DNA
<213> ORGANISM: artificial
<220> FEATURE:
<223> OTHER INFORMATION: Transcription factor binding sequence

<400> SEQUENCE: 33
agctgactca c 11

<210> SEQ ID NO 34
<211> LENGTH: 13
<212> TYPE: DNA
<213> ORGANISM: artificial
<220> FEATURE:
<223> OTHER INFORMATION: Transcription factor binding sequence

<400> SEQUENCE: 34
ctcatttaca tac 13

<210> SEQ ID NO 35
<211> LENGTH: 577
<212> TYPE: DNA
<213> ORGANISM: Corynebacterium diphtheriae

<400> SEQUENCE: 35
ctgatgatgt tgttgattct tctaaatctt ttgtgatgga aaacttttct tcgtaccacg 60
ggactaaacc tggttatgta gattccattc aaaaaggtat acaaaagcca aaatctggta 120
cacaaggaaa ttatgacgat gattggaaag ggttttatag taccgacaat aaatacgacg 180
ctgcgggata ctctgtagat aatgaaaacc cgctctctgg aaaagctgga ggcgtggtca 240
aagtgacgta tccaggactg acgaaggttc tcgcactaaa agtggataat gccgaaacta 300
ttaagaaaga gttaggttta agtctcactg aaccgttgat ggagcaagtc ggaacggaag 360
agtttatcaa aaggttcggt gatggtgctt cgcgtgtagt gctcagcctt cccttcgctg 420
aggggagttc tagcgttgaa tatattaata actgggaaca ggcgaaagcg ttaagcgtag 480
aacttgagat taattttgaa acccgtggaa aacgtggcca agatgcgatg tatgagtata 540
tggctcaagc ctgtgcagga aatcgtgtca ggcgatc 577

<210> SEQ ID NO 36
<211> LENGTH: 20
<212> TYPE: DNA
<213> ORGANISM: artificial
<220> FEATURE:
<223> OTHER INFORMATION: RNAi/shRNA target sequence for mouse oct3/4

<400> SEQUENCE: 36
ggatgtggtt cgagtatggt 20

<210> SEQ ID NO 37
<211> LENGTH: 32
<212> TYPE: DNA
<213> ORGANISM: artificial
<220> FEATURE:
<223> OTHER INFORMATION: SNP sequence

<400> SEQUENCE: 37
tccctggaga attgacccgt atatggccac gt 32

<210> SEQ ID NO 38
<211> LENGTH: 32
<212> TYPE: DNA
<213> ORGANISM: artificial
<220> FEATURE:
<223> OTHER INFORMATION: SNP sequence

<400> SEQUENCE: 38
tccctgtgga actgaccttt atacggccac gt 32

<210> SEQ ID NO 39
<211> LENGTH: 677
<212> TYPE: DNA
<213> ORGANISM: Mus musculus

<400> SEQUENCE: 39
actgtgaggg gatggagcct gggtgcaggt cttatggggg ttgggggtg gttagtgtct 60 aatctaccaa cctggacaac acaagatgga atactgtgct ctgaaaacgc agagccagca 120
cttctctggg gtctctgggg acatatctgg ttggggctcg gggtcccatg gtgtagagcc 180
tctaaactct ggaggactgg aggtgcaatg gctgtcttgt cctggccttg gacatgggct 240

```
gaaatactgg gttcacccat atctaggact ctagacgggt gggtaagcaa gaactgagga    300

gtggccccag aaataattgg cacacgaaca ttcaatggat gttttaggct ctccagagga    360

tggctgagtg ggctgtaagg acaggccgag agggtgcagt gccaacaggc tttgtggtgc    420

gatggggcat ccgagcaact ggtttgtgag gtgtccggtg acccaaggca ggggtgagag    480

gaccttgaag gttgaaaatg aaggcctcct ggggtcccgt cctaagggtt gtcctgtcca    540

gacgtcccca acctccgtct ggaagacaca ggcagatagc gctcgcctca gtttctccca    600

cccccacagc tctgctcctc cacccaccca gggggcgggg ccagaggtca aggctagagg    660

gtgggattgg ggaggga                                                   677


<210> SEQ ID NO 40
<211> LENGTH: 24
<212> TYPE: DNA
<213> ORGANISM: artificial
<220> FEATURE:
<223> OTHER INFORMATION: Primer sequence for genotyping

<400> SEQUENCE: 40

cacgtgcagc cgtttaagcc gcgt                                            24


<210> SEQ ID NO 41
<211> LENGTH: 22
<212> TYPE: DNA
<213> ORGANISM: artificial
<220> FEATURE:
<223> OTHER INFORMATION: Primer sequence for genotyping

<400> SEQUENCE: 41

ttcccattct aaacaccctg aa                                              22


<210> SEQ ID NO 42
<211> LENGTH: 24
<212> TYPE: DNA
<213> ORGANISM: artificial
<220> FEATURE:
<223> OTHER INFORMATION: Primer sequence for genotyping

<400> SEQUENCE: 42

ctaggccaca gaattgaaag atct                                            24


<210> SEQ ID NO 43
<211> LENGTH: 25
<212> TYPE: DNA
<213> ORGANISM: artificial
<220> FEATURE:
<223> OTHER INFORMATION: Primer sequence for genotyping

<400> SEQUENCE: 43

gtaggtggaa attctagcat catcc                                           25


<210> SEQ ID NO 44
<211> LENGTH: 25
<212> TYPE: DNA
<213> ORGANISM: artificial
<220> FEATURE:
<223> OTHER INFORMATION: Primer sequence for genotyping

<400> SEQUENCE: 44

gttatcagta agggagctgc agtgg                                           25


<210> SEQ ID NO 45
<211> LENGTH: 24
<212> TYPE: DNA
```

```
<213> ORGANISM: artificial
<220> FEATURE:
<223> OTHER INFORMATION: Primer sequence for genotyping

<400> SEQUENCE: 45

ggcggatcac aagcaataat aacc                                          24


<210> SEQ ID NO 46
<211> LENGTH: 23
<212> TYPE: DNA
<213> ORGANISM: artificial
<220> FEATURE:
<223> OTHER INFORMATION: Primer sequence for genotyping

<400> SEQUENCE: 46

aagaccgcga agagtttgtc ctc                                           23


<210> SEQ ID NO 47
<211> LENGTH: 196
<212> TYPE: PRT
<213> ORGANISM: Corynebacterium diphtheriae

<400> SEQUENCE: 47

Met Asp Pro Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Leu
        195


<210> SEQ ID NO 48
<211> LENGTH: 193
<212> TYPE: PRT
<213> ORGANISM: Corynebacterium diphtheriae

<400> SEQUENCE: 48

Glu Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30
```

```
Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Asp
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg


<210> SEQ ID NO 49
<211> LENGTH: 1773
<212> TYPE: DNA
<213> ORGANISM: human herpesvirus 1

<400> SEQUENCE: 49

atggccagct accccctgtca ccagcacgcc agcgccttcg accaggccgc tagaagcaga      60

ggccacagca acagaagaac cgccctgaga cccagaagac agcaggaggc cacagaggtg     120

agactggagc agaagatgcc caccctgctg agagtgtaca tcgatggacc ccacggcatg     180

ggcaagacca caacaaccca gctgctggtg gccctgggca gcagagacga catcgtgtac     240

gtgcccgagc ccatgaccta ctggcaggtg ctgggagcca gcgagaccat cgccaacatc     300

tacaccacac agcacagact ggaccagggc gagatcagcg ccggcgacgc tgccgtggtg     360

atgaccagcg cccagatcac aatgggcatg ccctacgccg tgaccgatgc cgtgctggct     420

ccccacgtgg gcggagaggc cggcagcagc cacgcccctc cccctgccct gaccctgatc     480

ttcgacagac accccatcgc cgccctgctg tgctaccccg ccgctagata cctgatgggc     540

agcatgacac cccaggccgt gctggccttc gtggccctga tccccccctac cctgcccggc     600

accaacatcg tgctgggcgc cctgcccgag gacagacaca tcatggcttc gtacccctgc     660

catcaacacg cgtctgcgtt cgaccaggct gcgcgttctc gcggccatag caaccgacgt     720

acggcgttgc gccctcgccg gcagcaagaa gccacggaag tccgcctgga gcagaaaatg     780

cccacgctac tgcgggttta tatagacggt cctcacggga tggggaaaac caccaccacg     840

caactgctgg tggccctggg ttcgcgcgac gatatcgtct acgtacccga gccgatgact     900

tactggcagg tgctgggggc ttccgagaca atcgcgaaca tctacaccac acaacaccgc     960

ctcgaccagg gtgagatatc ggccggggac gcggcggtgg taatgacaag cgcccagata    1020

acaatgggca tgccttatgc cgtgaccgac gccgttctgg ctcctcatat cggggggggag    1080

gctgggagct cacatgcccc gcccccggcc ctcaccctca tcttcgaccg ccatcccatc    1140

gccgccctcc tgtgctaccc ggccgcgcga taccttatgg gcagcatgac cccccaggcc    1200
```

```
gtgctggcgt tcgtggccct catcccgccg accttgcccg gcacaaacat cgtgttgggg   1260

gcccttccgg aggacagaca catcgaccgc ctggccaaac gccagcgccc cggcgagcgg   1320

cttgacctgg ctatgctggc cgcgattcgc cgcgtttacg ggctgcttgc caatacggtg   1380

cggtatctgc agggcggcgg gtcgtggcgg gaggattggg gacagctttc ggggacggcc   1440

gtgccgcccc agggtgccga gccccagagc aacgcgggcc cacgacccca tatcggggac   1500

acgttattta ccctgtttcg ggcccccgag ttgctggccc ccaacggcga cctgtacaac   1560

gtgtttgcct gggccttgga cgtcttggcc aaacgcctcc gtcccatgca cgtctttatc   1620

ctggattacg accaatcgcc cgccggctgc cgggacgccc tgctgcaact tacctccggg   1680

atgatccaga cccacgtcac caccccaggc tccataccga cgatctgcga cctggcgcgc   1740

acgtttgccc gggagatggg ggaggctaac taa                                1773
```

<210> SEQ ID NO 50
<211> LENGTH: 376
<212> TYPE: PRT
<213> ORGANISM: human herpesvirus 1

<400> SEQUENCE: 50

```
Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Arg
                245                 250                 255

Glu Asp Trp Gly Gln Leu Ser Gly Thr Ala Val Pro Pro Gln Gly Ala
            260                 265                 270
```

-continued

```
Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Ile Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375
```